US012378584B2

(12) United States Patent
Wiltschi et al.

(10) Patent No.: US 12,378,584 B2
(45) Date of Patent: Aug. 5, 2025

(54) METHIONINE ANALOGUE SYNTHESIS

(71) Applicant: ENGENES BIOTECH GMBH, Vienna (AT)

(72) Inventors: Birgit Wiltschi, Graz (AT); Patrik Fladischer, Gerasdorf (AT); Lisa-Ramona Offner-Marko, Kraubath an der Mur (AT); Kathrin Heckenbichler, Linz (AT); Rolf Breinbauer, Graz (AT)

(73) Assignee: ENGENES BIOTECH GMBH, Vienna (AT)

( * ) Notice: Subject to any disclaimer, the term of this patent is extended or adjusted under 35 U.S.C. 154(b) by 140 days.

(21) Appl. No.: 17/251,742

(22) PCT Filed: Jun. 12, 2019

(86) PCT No.: PCT/EP2019/065290
§ 371 (c)(1),
(2) Date: Dec. 11, 2020

(87) PCT Pub. No.: WO2019/238725
PCT Pub. Date: Dec. 19, 2019

(65) Prior Publication Data
US 2021/0261990 A1    Aug. 26, 2021

(30) Foreign Application Priority Data

Jun. 13, 2018   (LU) ........................................ 100833

(51) Int. Cl.
*C12P 13/12*      (2006.01)
(52) U.S. Cl.
CPC .................................... *C12P 13/12* (2013.01)
(58) Field of Classification Search
CPC ...................................................... C12P 13/12
See application file for complete search history.

(56) References Cited

U.S. PATENT DOCUMENTS 7,381,549 B2 *   6/2008   Kroger ..................... C12P 13/04
                                                              435/195

FOREIGN PATENT DOCUMENTS

EP         2060584 A1      5/2009
WO      2017/025766 A1      2/2017

OTHER PUBLICATIONS

Taskent-Sezgin et al., Angew. Chem. Int. Ed. 49:7473-7475, 2010.*
Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Singh et al., Current Protein and Peptide Science 19(1):5-15, 2018.*
Sadowski et al., Current Opinion in Structural Biology 19:357-362, 2009.*
Turkewitz et al., Biochemistry and Biophysics Reports 26:101015, pp. 1-12, 2021.*
Panek et al., Acta Biochimica Polonica 60(2):163-166, 2013.*
Agard et al., "A Strain-Promoted [3+2] Azide-Alkyne Cycloaddition for Covalent Modification of Biomolecules in Living Systems," Journal of the American Chemical Society, vol. 126, No. 46, Nov. 2004, pp. 15046-15047 and Supporting Information 7 pp. and correction 1 pg.
Albermann et al., "A simple and reliable method to conduct and monitor expression cassette integration into the *Escherichia coli* chromosome," Biotechnology Journal, Special Issue: Biotech Methods and Advances, vol. 5, No. 1, Jan. 2010, pp. 32-38 and Supporting Information 2 pp.
Anderhuber et al., "High-level biosynthesis of norleucine in *E. coli* for the economic labeling of proteins," Journal of Biotechnology, vol. 235, Apr. 2016, pp. 100-111 and Supporting Information 15 pp.
Boll et al., "Access to Cyclic or Branched Peptides Using Bis(2-sulfanylethyl)amido Side-Chain Derivatives of Asp and Glu," Organic Letters, vol. 14, No. 9, Apr. 2012, pp. 2222-2225 and Supporting Information 115 pp.
Calos, M.P., "DNA sequence for a low-level promoter of the lac repressor gene and an 'up' promoter mutation," Nature, vol. 274, No. 5673, Aug. 1978, pp. 762-765.
Cantrell, S.A., "Chapter 28—Vectors for the Expression of Recombinant Proteins in *E. coli*," from Methods in Molecular Biology, vol. 235: *E. coli* Plasmid Vectors, Eds. Casall et al., Humana Press Inc., 2003, 19 pp.
Choi et al., "Novel, Versatile, and Tightly Regulated Expression System for *Escherichia coli* Strains," Applied and Environmental Microbiology, vol. 76, No. 15, Jun. 2010, pp. 5058-5066 and Supporting Information 10 pp.
Condreay et al., "Transient and stable gene expression in mammalian cells transduced with a recombinant baculovirus vector," Proceedings of the National Academy of Sciences of the United States of America (PNAS), vol. 96, No. 1, Jan. 1999, pp. 127-132.
Datsenko et al., "One-step inactivation of chromosomal genes in *Escherichia coli* K-12 using PCT products," Proceedings of the National Academy of Sciences of the United States of America (PNAS), vol. 97, No. 12, Jun. 2000, pp. 6640-6645.
Dumas et al., "Designing logical condon reassignment-Expanding the chemistry in biology," Chemical Science, vol. 6, No. 1, Jul. 2014, pp. 50-69.
Floyd et al., "Thiyl Glycosylation of Olefinic Proteins: S-Linked Glycoconjugate Synthesis," Angewandte Chemie International Edition, vol. 48, No. 42, Oct. 2009, pp. 7798-7802 and Supporting Information 72 pp.

(Continued)

*Primary Examiner* — Delia M Ramirez
(74) *Attorney, Agent, or Firm* — Mueting Raasch Group

(57) ABSTRACT

The present invention relates to a method for preparing a methionine analogue, comprising contacting a host cell with L-homoserine and one or more nucleophiles and cultivating said host cell and said one or more nucleophiles of (a) in a fermentation broth to produce said methionine analogue, wherein said host cell encodes and stably expresses a L-homoserine-O-acetyl-transferase (HSAT) and an O-acetyl-L-homoserine sulfhydrylase (OAHS). The present invention also relates to host cells encoding and expressing such HSAT and OAHS, as well as uses thereof for producing a methionine analogue.

Figure 1:
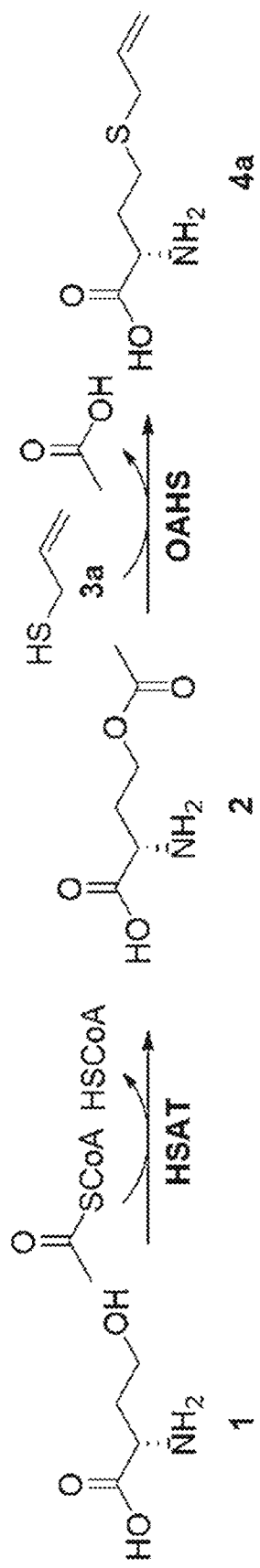

12 Claims, 30 Drawing Sheets
Specification includes a Sequence Listing.

(56) References Cited

OTHER PUBLICATIONS

Gamper et al., "The DNA strand of chimeric RNA/DNA oligonucleotides can direct gene repair/conversion activity in mammalian and plant cell-free extracts," Nucleic Acids Research, vol. 28, No. 21, Nov. 2000, pp. 4332-4339.
Garner, P.P., "Chapter 1—Diels-Alder reactions in aqueous media," from Organic Synthesis in Water, Ed. by Paul A. Grieco, Blackie Academic & Professional and Imprint of Chapman & Hall, 1998, pp. 1-46.
Gibson et al., "Enzymatic assembly of DNA molecules up to several hundred kilobases," Nature Methods, vol. 6, No. 5, Apr. 2009, pp. 343-345 and Supplemental Information 14 pp.
Gourinchas et al., "A synthetic biology approach for the transformation of L-α-amino acids to the corresponding enantiopure (R)- or (S)-α-hydroxy acids," Chemical Communications, vol. 51, No. 14, Jan. 2015, pp. 2828-2831 and Supplemental Information 38 pp.
Hohsaka et al., "Incorporation of non-natural amino acids into proteins," Current Opinion in Chemical Biology, vol. 6, No. 6, Oct. 2002, pp. 809-815.
Imai et al., "Neuroprotective effect of S-allyl-l-cysteine derivatives against endoplasmic reticulum stress-induced cytotoxicity is independent of calpain inhibition," Journal of Pharmacological Sciences, vol. 130, No. 3, Mar. 2016, pp. 185-188.
Jiang et al., "Multigene Editing in the *Escherichia coli* Genome via the CRISPR-Cas9 System," Applied and Environmental Microbiology, vol. 81, No. 7, Apr. 2015, pp. 2506-2514 and Erratum Information 6 pp.
Johnson et al., "Residue-specific incorporation of non-canonical amino acids into proteins: recent developments and applications," Current Opinion in Chemical Biology, vol. 14, No. 6, Dec. 2010, pp. 774-780.
Knall et al., "Inverse electron demand Diels-Alder (iEDDA)-initiated conjugation: a (high) potential click chemistry scheme," Chemical Society Reviews, vol. 42, No. 12, Apr. 2013, pp. 5131-5142.
Lampropoulou et al., "Effect of O-allyl-hydroxy Amino Acids on Protein Synthesis and Secretion by Cultured Fat Body and Salivary Glands in the Fruit Fly Ceratitis capitata," International Journal of Biochemistry, vol. 19, No. 1, 1987, pp. 89-92.
Lang et al., "Genetically encoded norbornene directs site-specific cellular protein labelling via a rapid bioorthogonal reaction," Nature Chemistry, vol. 4, No. 4, Feb. 2012, pp. 298-304 and Supplementary Information 35 pp.
Lang et al., "Bioorthogonal Reactions for Labeling Proteins," ACS Chemical Biology, vol. 9, No. 1, Jan. 2014, pp. 16-20.
Li et al., "Genetically encoded alkenyl-pyrrolysine analogues for thiol-ene reaction mediated site-specific protein labeling," Chemical Science, vol. 3, No. 9, Jun. 2012, pp. 2766-2770 and Supporting Information 14 pp.
Lin et al., "Olefin Metathesis for Site-Selective Protein Modification," ChemBioChem: a European Journal of Chemical Biology, vol. 10, No. 6, Apr. 2009, pp. 959-969.
Liu et al., "Adding New Chemistries to the Genetic Code," Annual Review of Biochemistry, vol. 79, Mar. 2010, pp. 413-444.
Ma et al., "Coupling Bioorthogonal Chemistries with Artificial Metabolism" Intracellular Biosynthesis of Azidohomoalanine and Its Incorporation into Recombinant Proteins, Molecules, vol. 19, No. 1, Jan. 2014, pp. 1004-1022.
Ma, Y., "Metabolic engineering of O-acetyl-L-homoserine sulfhydrylase and Mt-biosynthetic pathway in *Escherichia coli*, Residue-specific chemoselective conjugation on azide functionalized proteins" Technical University Berlin, Dissertation, Jul. 2016, pp. 98.
Maier, T. H.P., "Semisynthetic production of unnatural L-α-amino acids by metabolic engineering of the cysteine- biosynthetic pathway," Nature Biotechnology, vol. 21, No. 4, Mar. 2003, pp. 422-427.
Muttach et al., "A Biocatalytic Cascade for Versatile One-Pot Modification of mRNA Starting from Methionine Analogues," Angewandte Chemie International Edition, vol. 55, No. 5, Dec. 2015, pp. 1917-1920.
Ngo et al., "Noncanonical Amino Acids in the Interrogation of Cellular Protein Synthesis," Accounts of Chemical Research, vol. 44, No. 9, Aug. 2011, pp. 677-685.
O'Donoghue et al., "Upgrading protein synthesis for synthetic biology," Nature Chemical Biology, vol. 9, No. 10, Oct. 2013, pp. 594-598.
Omura et al., "Purification, Characterization and Gene Cloning of Thermostable O-Acetyl-L-Homoserine Sulfhydrylase Forming γ-Cyano-α-Aminobutyric Acid," Journal of Bioscience and Bioengineering, vol. 96, No. 1, Jan. 2003, pp. 53-58.
Rostovtsev et al., "A Stepwise Huisgen Cycloaddition Process: Copper(I)-Catalyzed Regioselective "Ligation" of Azides and Terminal Alkynes," Angewandte Chemie International Edition, vol. 41, No. 14, Jul. 2002, pp. 2596-2599 and Supporting Information 5 pp.
Ryu et al., "Efficient incorporation of unnatural amino acids into proteins in *Escherichia coli*," Nature Methods, vol. 3, No. 4, Mar. 2006, pp. 263-265 and Supplementary Methods 4 pp.
Sampson et al., "Exploiting CRISPR/Cas systems for biotechnology," BioEssays: news and reviews in molecular, cellular and developmental biology, vol. 36, No. 1, Dec. 2013, pp. 34-38.
Thomsen et al., "Chemoenzymatic synthesis and in situ application of S-adenosyl-l-methionine analogs," Organic & Biomolecular Chemistry, vol. 11, No. 43, Nov. 2013, pp. 7606-7610.
Van Kasteren et al., "Expanding the diversity of chemical protein modification allows post-translational mimicry," Nature, vol. 446, No. 7139, Apr. 2007, pp. 1105-1109 and Supplementary Information 109 pp.
Walsh et al., "Nonproteinogenic Amino Acid Building Blocks for Nonribosomal Peptide and Hybrid Polyketide Scaffolds," Angewandte Chemie International Edition, vol. 52, No. 28, May 2013, pp. 7098-7124 and Supporting Information 32 pp.
Wan et al., "Pyrrolysyl-tRNA synthetase: An ordinary enzyme but an outstanding genetic code expansion tool," Biochimica et Biophysica Acta, vol. 1844, No. 6, Mar. 2014, pp. 1059-1070.
Wang et al., "Expanding the Genetic Code of *Escherichia coli*," Science, vol. 292, No. 5516, Apr. 2001, pp. 498-500 and Supplemental Data 2 pp.
Wiltschi, B., "Chapter 13 Expressed Protein Modifications: Making Synthetic Proteins," Synthetic Gene Networks: Methods in Molecular Biology (MIMB), Weber et al. Eds., Humana Press, vol. 813, Oct. 2011, pp. 211-225.
Wiltschi, B., "Chapter 4 Protein Building Blocks and the Expansion of the Genetic Code," Synthetic Biology, Glieder et al. Eds., Springer International Publishing Switzerland, 2016, pp. 143-209.
Wiltschi, B., "Non-canonical amino acids as building blocks for designer proteins," Designer Biology: From proteins and cells to scaffolds & materials, Conference Paper, Jun. 2017, pp. 2.
Young et al., "Beyond the Canonical 20 Amino Acids: Expanding the Genetic Lexicon," Journal of Biological Chemistry, vol. 285, No. 15, Feb. 2010, pp. 11039-11044.
GenBank Protein Accession No. E16859: DNA encoding Bacillus gamma-cyano-alpha-aminobutyric acid synthetase (1302 bp), Nov. 5, 2005, 2 pages.
Enzyme entry: EC 2.3.1.31 homoserine O-acetyltransferase, from Expasy downloaded May 31, 2024.
Enzyme entry: EC 2.5.1.49 O-acetylhomoserine aminocarboxypropyltranserase, from Expasy downloaded May 31, 2024.
UniProt Protein Accession No. Q9RVZ8: Homoserine O-acetyltransferase (334 aa), Mar. 27, 2024, 2 pages.
PDBsum entry: 2b61 Transferase, from EMBL-EBI downloaded May 31, 2024, 2 pages.
PDBsum entry: 4oc9 Lyase, from EMBL-EBI downloaded May 31, 2024, 1 page.
UniProt Protein Accession No. W7N293: Homoserine O-acetylransferase FUB5, Apr. 16, 2014, 6 pages.

(56) References Cited

OTHER PUBLICATIONS

Safety Data Sheet, Version 6.2, Section 1: Identification of the substance/mixture and of the company/undertaking, Product name: 5-Norbornen-2-ol, mixture of endo and exo, Sigma-Aldrich, Print Date May 26, 2024, 9 pages.

* cited by examiner

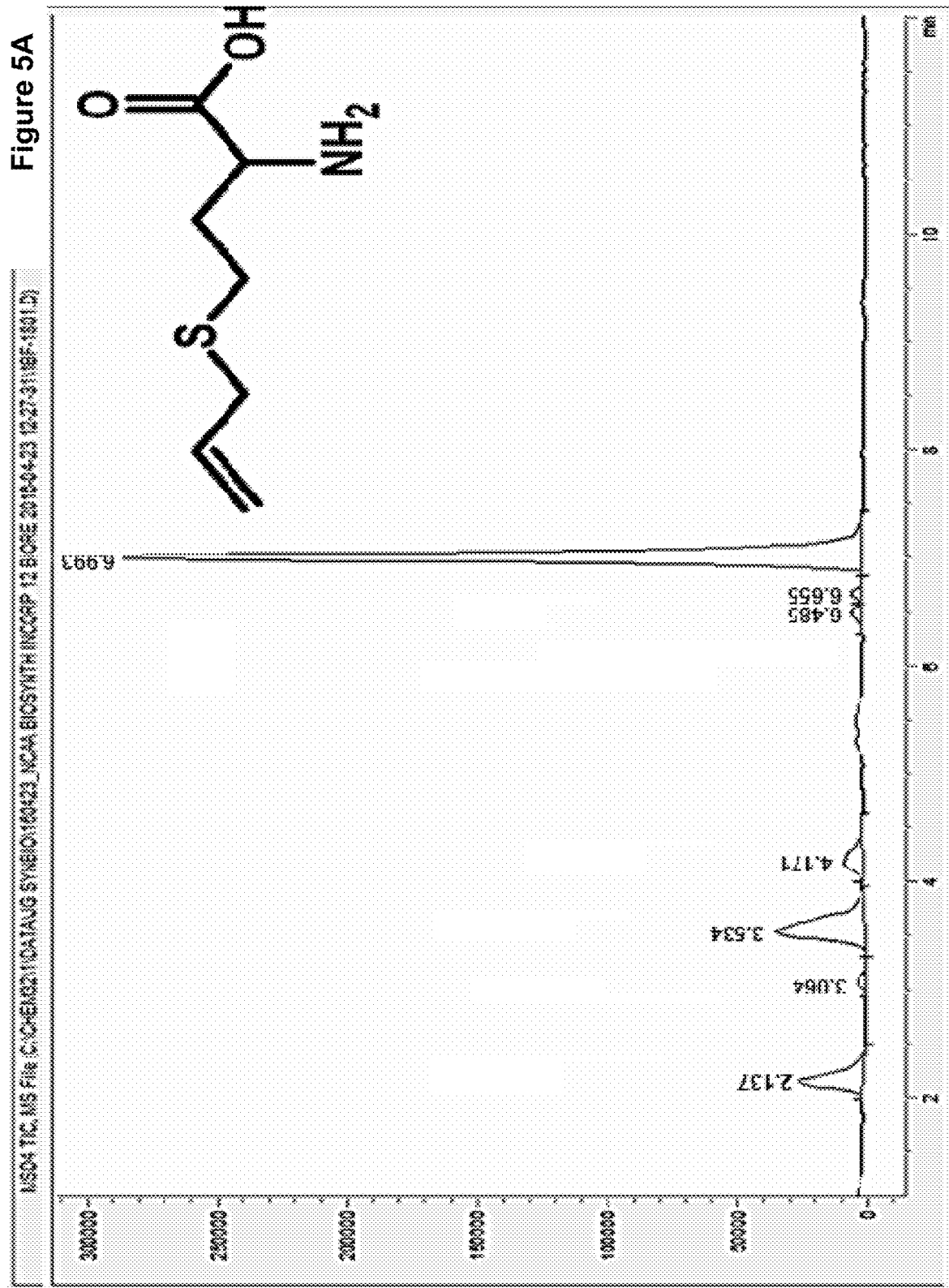

A

B

A

B

METHIONINE ANALOGUE SYNTHESIS

PRIORITY CLAIM

This application claims priority to International Application No. PCT/EP2019/065290, filed Jun. 12, 2019, which claims priority to Luxembourg Application No. 100833, filed Jun. 13, 2018, wherein the contents of said applications are incorporated herein by reference in their entireties. Also, the entire contents of the ASCII text file entitled "IPM0108US_Sequence_Listing.txt" created on Dec. 10, 2020, having a size of 12 kilobytes is incorporated herein by reference.

The present invention relates to a method for preparing a methionine analogue, comprising contacting a host cell with L-homoserine and one or more nucleophiles and cultivating said host cell and said one or more nucleophiles of (a) in a fermentation broth to produce said methionine analogue, wherein said host cell encodes and stably expresses a L-homoserine-O-acetyl-transferase (HSAT) and an O-acetyl-L-homoserine sulfhydrylase (OAHS). The present invention also relates to host cells encoding and expressing such HSAT and OAHS, as well as uses thereof for producing a methionine analogue.

With a few exceptions, all known organisms use the same set of 20 canonical amino acids (cAAs) prescribed by the genetic code for protein biosynthesis. As a result, the chemical diversity in proteins is confined to this small and defined set of cAAs (O'Donoghue, et al. Nat Chem Biol (2013), 9(10): 594-598; Wiltschi (2016). Protein building blocks and the expansion of the genetic code. In *Synthetic Biology*. A. Glieder, C. Kubicek, D. Mattanovich, B. Wiltschi and M. Sauer. Switzerland, Springer International Publishing, pp. 143). Proteins Implement a remarkable range of functions, but often they do not offer the chemistries that are desirable for biotechnological applications. These limitations may be overcome using non-canonical amino acids (ncAAs), which are a very diverse group of compounds. Though naturally not participating in protein translation, ncAAs offer a broad spectrum of side chain chemistries and many of them occur in nature (Walsh et al., Angew Chem Int Ed Engl (2013), 52(28): 7098-7124). Currently, there are several approaches available to incorporate these ncAAs into proteins to exploit their broad structural and functional repertoire.

Tools for the site-specific incorporation of ncAAs into target proteins are known in the art (Wang et al., Science (2001), 292(5516): 498-500; Hohsaka et al., Curr Opin Chem Biol (2002), 6(6): 809-815). To do so, an engineered aminoacyl-tRNA synthetase (aaRS) is needed that accepts exclusively the ncAA and charges it on its cognate tRNA. For example, a tRNA suppressing a stop codon may be used. This methodology is known as stop codon suppression (SCS) (Young et al., J Biol Chem (2010), 285(15): 11039-11044). For SCS it is important that the pair consisting of the ncAA-specific aaRS and the $tRNA_{CUA}$ is orthogonal (o-pair), which means it does not interfere with the endogenous translation system of the host (Wang (2001), loc. cit.). In early years, many of the o-pairs developed were based on the archaeal $TyrRS/RNA_{CUA}^{Tyr}$ from *Methanocaldococcus jannaschii* (Mj) (Ryu et al., Nat Methods (2006), 3(4): 263-265; Liu et al., Annu Rev Biochem (2010), 79(1): 413-444). The Mj o-pairs have been extensively used for the incorporation of a whole set of different ncAAs (Dumas et al., Chem Sci (2015), 6(1): 50-59).

Besides Phe and Lys analogs (Wan et al., Biochim Biophys Acta (2014), 1844(6): 1059-1070), Met analogs with reactive side chains have been alternatively incorporated into proteins (van Kasteren et al., Nature (2007), 446(7139): 1105-1109). This technique enables the labeling of proteins with unique handles amenable for subsequent bioorthogonal conjugation reactions (Ngo et al., Acc Chem Res (2011), 44(9): 677-485; Johnson et al., Curr Opin Chem Biol (2010), 14(6): 774-780; and Ma et al., Molecules (2014), 19(1): 1004-1022). Bioorthogonal conjugations are indispensable for the directed, site-specific chemical modification of proteins (Lang et al., ACS Chem Biol (2014), 9(1): 16-20). The commonly used Met analogs L-azidohomoalanine (Aha) and L-homopropargylglycine (Hpg) (Johnson et al., (2010), loc. cit.) are commercially available but both ncAAs come at a high price, which makes their large scale applications forbiddingly expensive. A corresponding method for the biosynthesis of cysteine analogs applying a different set of enzymes was shown (Maier Nat Biotechnol (2003), 21(4): 422-427). Additionally, a proof of concept for the biosynthesis and direct incorporation of Aha was shown in a recent study (Ma et al., (2014), loc. cit.). In this study, Aha was biosynthesized from O-acetyl-L-homoserine (OAH) and sodium azide using the O-acetyl-homoserine sulfhydrylase (OAHS) from *Corynebacterium glutamicum*. In a first approach, the OAH was supplemented to the medium, but also a strategy for the biosynthesis of OAH from L-homoserine (HS) using the L-homoserine-O-acetyltransferase (HSAT) from *Corynebacterium glutamicum* was shown. Furthermore, using this approach the in-situ synthesis of S-allyl-L-homocysteine (Sen) providing allyl mercaptan as nucleophile was successfully demonstrated. Additionally, a whole list of possible substrates for the synthesis of different Met analogs using the OAHS from *Corynebacterium glutamicum* is provided (Ma, (2016), Metabolic engineering of O-acetyl-L-homoserine sulfhydrylase and Met-biosynthetic pathway in *Escherichia coli*, Technische Universität Berlin).

However, commercially available methionine analogues are expensive, and known synthesis methods are cumbersome and require feeding of intermediates which are expensive themselves or need to be synthesized in a time-consuming manner.

Accordingly, the technical problem underlying the present invention was to comply with the needs set out above. The technical problem has been solved by means and methods as described herein as defined in the claims.

The present invention therefore provides a method for preparing a methionine analogue, comprising the following steps:
  (a) contacting a host cell with L-homoserine and one or more nucleophiles; and
  (b) cultivating said host cell and said one or more nucleophiles of (a) in a fermentation broth to produce said methionine analogue,
  wherein said host cell encodes and stably expresses a L-homoserine-G-acetyl-transferase (HSAT) and an O-acetyl-L-homoserine sulfhydrylase (OAHS).

In context with the present invention, it does not matter whether the L-homoserine of (a) is added to the host cell, or synthesized by the host cell. That is, L-homoserine may be added to the host cell to bring into contact with the host cell, and/or the host cell may comprise and/or synthesize L-homoserine endogenously (e.g., naturally or via genetic engineering) and is thus contacted with L-homoserine. In accordance with the present invention, the same applies mutatis mutandis to nucleophiles which may be added to the host cell or be comprised and/or synthesized by the host cell endogenously.

In one embodiment of the present invention, said O-acetyl-L-homoserine sulfhydrylase (OAHS) is derived from *Geobacillus stearothermophilus* (for example, sequence as shown in genbank accession no. E16859.1; Omura et al., J Biosci Bioeng (2003), 96(1): 53-58). In one embodiment of the present invention, the OAHS has the amino acid sequence as shown in SEQ ID NO: 1.

A specific enzyme (e.g., OAHS or HSAT) or protein sequence being "derived from" a certain organism (e.g., *Geobacillus stearothermophilus, Deinococcus radiodurans*, or *Mycobacterium smegmatis*, respectively) as used herein means a corresponding enzyme or protein sequence which are obtainable from said organism and comprises all variants of such enzyme which exhibit the corresponding enzyme ability. For example and in context with the present invention, an O-acetyl-L-homoserine sulfhydrylase (OAHS) preferably exhibits the ability to convert O-acetyl-L-homoserine (together with a nucleophile as described herein) to a methionine analogue as known in the art (e.g., Ma, (2016), loc. cit., and Omura et al., (2003), loc. cit.) and as described herein. As another example in this context, an L-homoserine-O-acetyl-transferase (HSAT) preferably exhibits the ability to convert L-homoserine to O-acetyl-L-homoserine. The corresponding enzymes and their abilities are known in the art, e.g., in Ma (2014), loc. cit., and Ma (2016), loc. cit. For example, in context with the present invention, the amino acid sequence of a representative of OAHS derived from *Geobacillus stearothermophilus* (CN3) (for example, genbank accession no. E16859.1; Omura et al., (2003), loc. cit.) is shown in SEQ ID NO: 1, and the amino acid sequences of a representative of HSAT derived from *Deinococcus radiodurans* (for example, genbank accession no. Q9RVZ8) is shown in SEQ ID NO: 2, and that of *Mycobacterium smegmatis* is shown in SEQ ID NO: 3, respectively. Accordingly, in one embodiment of the present invention, an OAHS as used herein may be derived from *Geobacillus stearothermophilus* and may have an amino acid sequence as shown in SEQ ID NO: 1. In a further embodiment of the present invention, an HSAT may be derived from *Deinococcus radiodurans* and may have an amino acid sequence as shown in SEQ ID NO: 2, and/or an HSAT may be derived from *Mycobacterium smegmatis* and may have an amino acid sequence as shown in SEQ ID NO: 3.

The term "derived from" as used herein also comprises al variants of a given protein derived from a given organism as it can be directly obtained from said organism, wherein the sequence of the protein (or the sequence of the encoding nucleic acid molecule, respectively) may have changed over time in the course of cultivation of the organism, provided the protein still exhibits the function of the original protein as directly obtainable by the organism before the cultivation. For example, in context with the present invention, an O-acetyl-L-homoserine sulfhydrylase (OAHS) preferably exhibits the ability to convert O-acetyl-L-homoserine (together with a nucleophile as described herein) to a methionine analogue as known in the art (e.g., Ma, (2016), loc. cit., and Omura et al., (2003), loc. cit.) and as described herein. As another example in this context, an L-homoserine-O-acetyl-transferase (HSAT) preferably exhibits the ability to convert L-homoserine to O-acetyl-L-homoserine. The corresponding enzymes and their abilities are known in the art, e.g., in Ma (2014), loc. cit., and Ma (2016), loc. cit.

Furthermore, as used herein, the term "derived from" also includes enzymes having a similar amino acid sequence as the corresponding enzyme directly obtained from the corresponding organism. For example, in context with the present invention, an OAHS derived from *Geobacillus stearothermophilus* may have the amino acid sequence shown in SEQ ID NO: 1, or a sequence having up to 50, 45, 40, 35, 30, 25, 20, 15, 12, 10, 9, 8, 7, 6, 5, 4, 3, 2 or 1 amino acid deviations (substitutions, additions, insertions and/or deletions) compared to the amino acid sequence of SEQ ID NO: 1, provided it is able to convert O-acetyl-L-homoserine (together with a nucleophile as described herein) to a methionine analogue as described and exemplified herein. Likewise, in context with the present invention, an HSAT derived from *Deinococcus radiodurans* may have an amino acid sequence as shown in SEQ ID NO: 2, or a sequence having up to 50, 45, 40, 35, 30, 25, 20, 15, 12, 10, 9, 8, 7, 6, 5, 4, 3, 2 or 1 amino acid deviations (substitutions, additions, insertions and/or deletions) compared to the amino acid sequence of SEQ ID NO: 2, provided it is able to convert homoserine to O-acetyl-L-homoserine. As another example in context with the present invention, an HSAT derived from *Mycobacterium smegmatis* may have an amino acid sequence as shown in SEQ ID NO: 3, or a sequence having up to 50, 45, 40, 35, 30, 25, 20, 15, 12, 10, 9, 8, 7, 6, 5, 4, 3, 2 or 1 amino acid deviations (substitutions, additions, insertions, and/or deletions) compared to the amino acid sequence of SEQ ID NO: 3, provided it is able to convert homoserine to O-acetyl-L-homoserine.

In context with the present invention, amino acid substitutions compared to a given amino acid sequence are preferably conservative amino acid substitutions. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be in an acidic amino acid substituted for another acidic amino acid, an amino acid with a nonpolar side chain substituted for another amino acid with a nonpolar side chain, a basic amino acid substituted for another basic amino acid, an amino acid with a polar side chain substituted for another amino acid with a polar side chain, etc. that may be made, for instance, on the basis of similarity in polarity, charge, solubility, hydrophobicity, hydrophilicity, and/or the amphipathic nature of the residues involved. As used herein, "silent" mutations mean base substitutions within a nucleic acid sequence which do not change the amino acid sequence encoded by the nucleic acid sequence. "Conservative" substitutions mean substitutions as listed as "Exemplary Substitutions" in Table I below. "Highly conservative" substitutions as used herein mean substitutions as shown under the heading "Preferred Substitutions" in Table I below.

The term "addition" as used herein refers to adding at least one nucleic acid residue/amino acid to the end of the given sequence, whereas "insertion" refers to inserting at least one nucleic acid residue/amino acid within a given sequence. The term "deletion" refers to deleting or removal of at least one nucleic acid residue or amino acid residue in a given sequence. The term "substitution" refers to the replacement of at least one nucleic acid residue/amino acid residue in a given sequence. These definitions as used here apply, mutatis mutandis, for all sequences provided and described herein.

The term "position" when used in accordance with the present invention means the position of an amino acid within an amino acid sequence depicted herein. The term "corresponding" in this context also includes that a position is not only determined by the number of the preceding nucleotides/amino acids.

TABLE I

Amino Acid Substitutions

| Original | Exemplary Substitutions | Preferred Substitutions |
| --- | --- | --- |
| Ala (A) | val; leu; ile | Val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; | leu |
| Leu (L) | norleucine; ile; val; met; ala; | ile |
| Lys (K) | arg; gin; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | ser | ser |
| Trp (W) | tyr; phe | tyr |
| Tyr (Y) | trp; phe; thr; ser | Phe |
| Val (V) | ile; leu; met; phe; ala; | leu |

Figure 7:
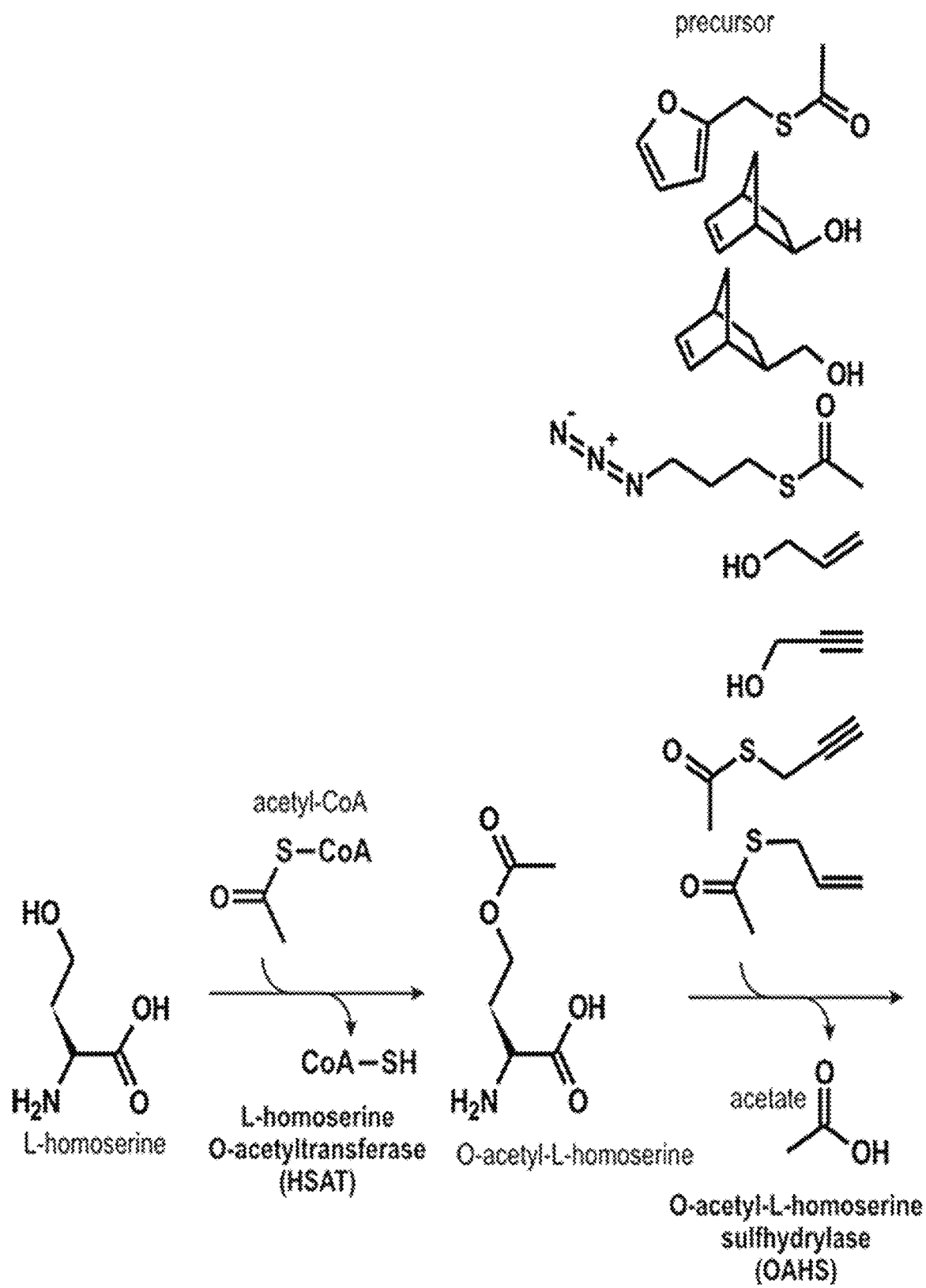
Figure 7:
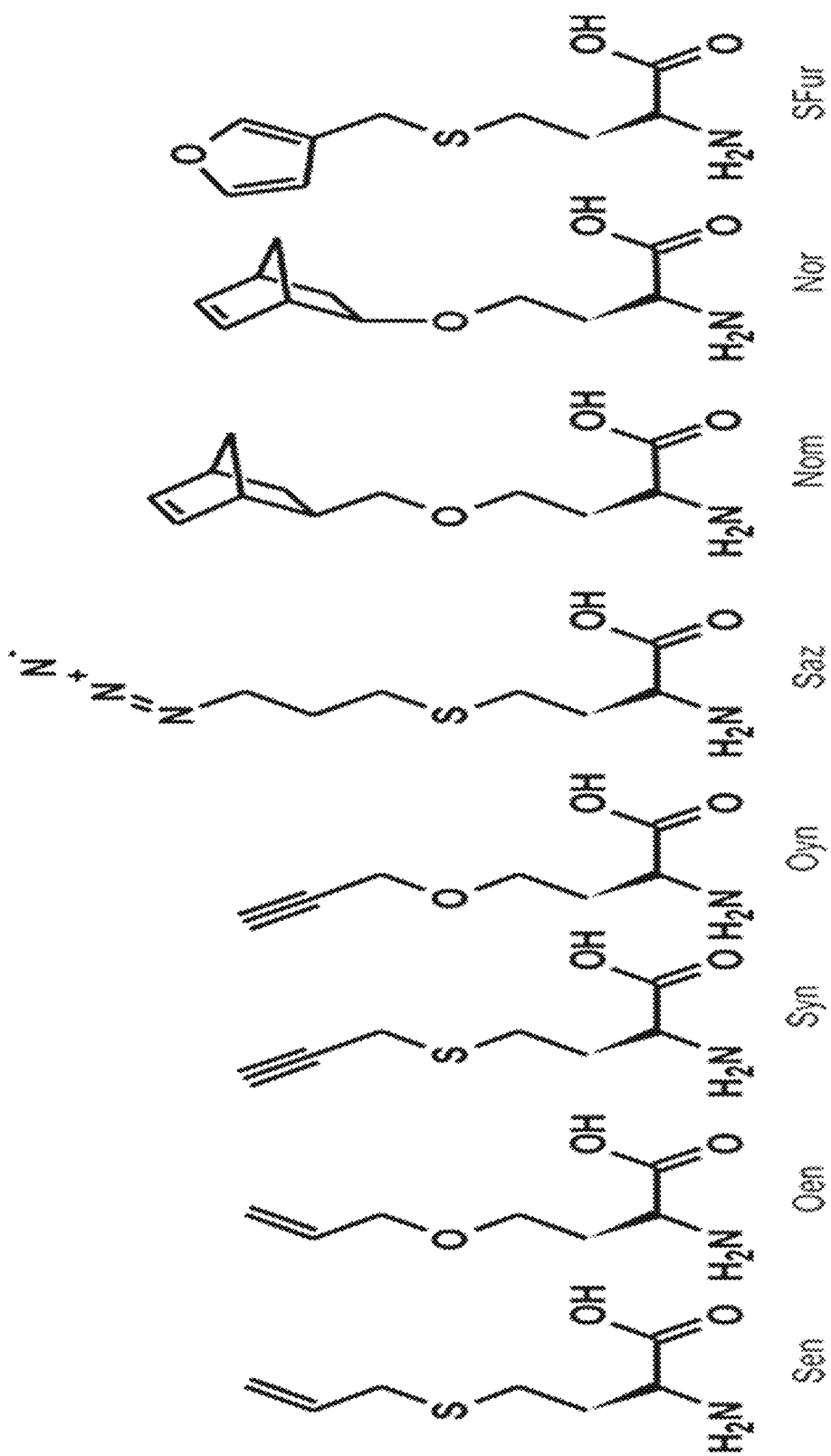

As has been surprisingly found in context with the present invention, co-expression of OAHS beside HSAT led to an improved method to synthesize methionine analogues since the addition or feeding of expensive intermediate metabolites (such as O-acetyl-L-homoserine) can be avoided. An exemplary scheme for synthesis of methionine analogues in accordance with the present invention is shown in FIG. 1. Further examples for synthesis of methionine analogues and corresponding nucleophiles in accordance with the present invention are shown in FIG. 7. In fact, the expression of OAHS derived from *Geobacillus stearothermophilus* has been shown in context with the present invention to be particularly advantageous compared to other OAHS as it shows improved production rates of methionine analogues (e.g., azidohomoalanine, Aha), allows thioester and surprisingly also easily available alcohols as nucleophiles for synthesizing the methionine analogues, and it is capable of converting not only simple nucleophiles with unsaturated side chains, but also those with ring systems (e.g., norbornene or furan). Finally, the inventive method not only allows residue-specific introduction of methionine analogues in proteins, but also site-specific introduction.

In context with the present invention, the host cell encodes and stably expresses an HSAT and an OAHS as described herein. Such host cell may in general be any kind of host cell, including eukaryotic or prokaryotic, as long as it encodes and is able to stably express HSAT and OAHS proteins. "Encoding" in this context means that the respective host cell comprises a nucleic acid molecule (e.g., DNA or (m)RNA) which encodes for the respective amino acid sequence of the respective HSAT or OAHS. The nucleic acid molecule may be a single molecule or integrated into a larger nucleic acid molecule (e.g., a chromosome, plasmid, vector, phage, phagemid, cosmid, or other) and may be, e.g., integrated or be part of an original genomic chromosome of the respective host cell, or it may be artificially introduced (e.g., via transduction, transfection, transformation) into the cell and, for example, Introduced into a chromosome of the host cell, or it may be on its own or part of, e.g., a plasmid or other nucleic acid vector within the host cell. The nucleic acid molecule encoding HSAT and that encoding OAHS may be part of a common nucleic acid molecule (e.g., be comprised by the same plasmid or integrated into the same chromosome), or may be separate or on separate nucleic acid molecules (e.g., comprised by separate plasmids). In one embodiment of the present invention, the HSAT encoding nucleic acid molecule and the OAHS encoding nucleic acid molecule are comprised within the same molecule, i.e. there is one nucleic acid molecule encoding for HSAT and OAHS. For example, this one nucleic acid molecule encoding for HSAT and OAHS may be a chromosome, a plasmid, a vector, phage, phagemid, cosmid, or other kind of suitable nucleic acid molecule, for example a plasmid. In this context, in a specific embodiment of the present invention, HSAT and OAHS genes are arranged in the order HSAT→OAHS (in view of a 5'→3' orientation) on the nucleic acid molecule. This order may allow even improved methionine analogue biosynthesis in accordance with the present invention (cf. FIG. 3). In this context, HSAT and OAHS may be under the control of a common promoter, for example in a polycistronic expression cassette. There may also be further genes under the same promoter control, either upstream or downstream of HSAT and/or OAHS. In another embodiment, HSAT and OAHS may have individual promoters (which may be each the same or different promoters) and/or other individual sequences such as RBS.

"Stable expression" of a given protein (e.g., HSAT or OAHS) or similar terms as used herein are generally known in the art (see, e.g., Condreay et al., PNAS (1999), 96(1): 127-132) and means preferably that the protein is actually expressed in the cell, i.e. It is synthesized. As known in the art, biosynthesis of a protein generally comprises the step of transcription of a nucleic acid molecule into an mRNA and translation of the mRNA into a protein (e.g., ribosomal translation). For translation, depending on the respective host cell, further nucleic acid segments beside that encoding the desired protein (e.g., HSAT or OAHS) may be required, e.g., promoter sequences, enhancer sequences, or other as known to the skilled person. Also, depending on the host cell used and the promoter sequence, the presence of suitable promoter activators or enhancers may be required. The skilled person is readily able to recognize how the proper translation of a given nucleic acid sequence can be realized. "Stable expression" and similar terms as used herein and as known in the art may also include that the nucleic acid molecule encoding the desired protein must be stably integrated into a larger nucleic acid molecule, e.g., a chromosome of the respective host cell, and that it must not be degraded or otherwise be inactivated within the host cell.

Generally, as used herein, the terms "polynucleotide" and "nucleic acid" or "nucleic acid molecule" are to be construed synonymously. Generally, nucleic acid molecules may comprise inter alia DNA molecules, RNA molecules, oligonucleotide thiophosphates, substituted ribo-oligonucleotides or PNA molecules. Furthermore, the term "nucleic acid molecule" may refer to DNA or RNA or hybrids thereof or any modification thereof that is known in the art (see, e.g., U.S. Pat. Nos. 5,525,711, 4,711,955, 5,792,608 or EP 302175 for examples of modifications). The polynucleotide sequence may be single- or double-stranded, linear or circular, natural or synthetic, and without any size limitation. For instance, the polynucleotide sequence may be genomic DNA, cDNA, mitochondrial DNA, mRNA, antisense RNA, ribozymal RNA or a DNA encoding such RNAs or chimeroplasts (Gamper et al., Nucleic Acids Res (2000), 28(21): 4332-4339). Said polynucleotide sequence may be in the form of a vector, plasmid or of viral DNA or RNA. Also described herein are nucleic acid molecules which are complementary to the nucleic acid molecules described above and nucleic acid molecules which are able to hybridize to nucleic acid molecules described herein. A nucleic acid molecule described herein may also be a fragment of the nucleic acid molecules in context of the present invention.

Particularly, such a fragment is a functional fragment. Examples for such functional fragments are nucleic acid molecules which can serve as primers.

A nucleic acid molecule (or its sequence, respectively) encoding a protein (e.g., OAHS and/or HSAT) derived from a given organism may be also be codon-optimized or codon-harmonized (both terms used interchangeably herein) for the respective host cell.

The term "codon-optimized", "codon-optimization", etc. as used herein is generally known in the art and inter alia relates to the fact that different organisms use different codons for the same amino acid in different frequencies ("codon usage" as known in the art). Due to different codon usage, it is possible that a gene from one organism may hardly or differently be expressed in another organism as the other organism uses one or more codons more often, more rarely or not at all and, thus, may have only few or no corresponding tRNAs for such codons and, consequently, suitable aminoacyl tRNA synthetases for such tRNAs. Accordingly, it may be required or at least advantageous to optimize the codons of a certain gene from one organism before transferring it to another organism in order to ensure comparable expression patterns. Such optimization usually takes place by substituting one or more bases within a nucleic acid sequence such as not to change its coded amino acid (i.e. silent mutation), but just to conform with the codon usage for a given amino acid codon with regard to the organism in which the nucleic acid molecule shall be expressed. For example, if in the original sequence of an aaRS the codon CTC for Leu and/or AGG for Arg is frequently contained, but the host cell (e.g., *E. coli*) in which the aaRS is expressed uses rather CTG for Leu and/or CGT for Arg, the codons in the nucleic acid sequence may be optimized (harmonized) accordingly. As such, as used herein, a given polynucleotide sequence may be considered "codon-optimized" to a selected host cell if it contains one or more codons for a given amino acid which is used with the highest frequency for said amino acid in said host cell. In one embodiment of the present invention, a given polynucleotide sequence may be considered "codon-optimized" to a selected host cell if it contains one or more respective codons used with the highest usage frequency in said selected host cell for 1, 2, 3 or all respective amino acids encoded by the polynucleotide. In a specific embodiment of the present invention, a given polynucleotide sequence may be considered "codon-optimized" to a selected host cell if it contains exclusively the respective codons with the highest usage frequency in the selected host cell for 1, 2, 3 or all respective encoded amino acids, i.e. no codon with a lower usage frequency for 1, 2, 3 or all respective encoded amino acids. Such codons with the highest frequency usage may be naturally contained in said polynucleotide or be introduced via suitable genetic modification tools known in the art (e.g., random or preferably site-specific mutations; PCR, restriction enzyme-based mutagenesis, CRISPR/Cas; gene/DNA synthesis, etc). Codon-optimization may also and additionally refer to exchange of different stop codons. For example, if a given host cell expresses certain suppressor molecules for certain stop codons, the stop codon (e.g., amber, ochre or opal) may be adapted accordingly. Such process as defined herein above is referred to herein as "codon-optimization". For many though not al organisms, there are codon usage tables available which show the codon usage frequency for the respective host cell, i.e. which codons are used more often than others (and at which ratio).

The host cell to be used in accordance with the present invention may be any kind of host cell, including eukaryotic or prokaryotic, as long as it encodes and is able to stably express HSAT and OAHS proteins. In context with the present invention, it is not necessary that the host cell naturally expresses a HSAT and/or OAHS. In one embodiment, the host cell used in accordance with the present invention does not express OAHS, in a further embodiment it neither expresses HSAT. In one embodiment, the host cell of the present invention may be a bacterium, or an eukaryote such as a fungi or mammal cell. In one embodiment, the host cell of the present invention may be a representative of Enterobacteriaceae (e.g., *Escherichia coli*), *Pichia* sp. (e.g., *Pichia pastoris*), a mammal cell (e.g., CHO or HEK) or a yeast (e.g., *S cerevisiae*), for example *E. coli*.

The present invention relates to methods for producing methionine analogues as described and provided herein. Such methionine analogues are preferably non-canonical amino acids. In one embodiment of the present invention, the methionine analogues are amino acids comprising an azido, alkyne, keto/aldehyde, alkene, norbornene, bis(2-sulfanylethyl)amido (SEA) or furan moiety in its side chain, for example azido, alkyne, keto/aldehyde, or norbornene.

The methionine analogues as prepared in accordance with the present invention may further substitute for Met in a target protein by residue specific incorporation by the supplementation based incorporation approach (SPI) (Wiltschi, Methods Mol Biol (2012), 813: 211-225), which results in labeling of the target protein with single or multiple reactive groups per protein depending on the number of Met codons. The palette of reactive groups is applicable in diverse biorthogonal conjugation reactions known in the art, such as, e.g., Cu(I)-catalyzed (e.g., for Aha, Oyn, Saz and Syn) (Rostovtsev et al., (2002), Angewandte Chemie International Edition. 41, 2596 Rostovtsev et al., Angew Chem Int Ed Engl (2002), 41(14): 2596-2599) or strain-promoted (e.g., for Aha, Saz) (Agard et al., J Am Chem Soc (2004), 126(46): 15046-15047) azide-alkyne cycloadditions ("click chemistry"); olefin metathesis of alkenes (e.g., for Sen, Oen) (Lin et al., ChemBioChem (2009), 10(6): 959-969); thiolene click chemistry (e.g., for Oen, Son) (Floyd et al., Angew Chem Int Ed Engl (2009), 48(42): 7798-7802; Li et al., Chem Sci (2012), 3(9): 2766-2770); Diels-Alder conjugation of furan and alkenes (e.g., for Fur, Son, Oen) (Garner, (1998) Diels-Alder reactions in aqueous media in Organic Synthesis in Water pp. 1, Springer Netherlands, Dordrecht), inverse electron demand Diels-Alder reactions (e.g., for Nor) (Knall et al., Chem Soc Rev (2013), 42(12): 5131-5142), e.g. between tetrazine and norbornene (Lang et al., Nat Chem (2012), 4(4): 298-304), oxime coupling for e.g., O-(3-oxobutoxy)-L-homoserine (Obo, IUPAC (2S)-2-amino-4-(3-oxobutoxy)butanoic acid), or SEA native peptide ligation for e.g. O-[2-(1,2,5-dithiazepan-5-yl)-2-oxoethoxy]-L-homoserine (SEA-Hse, IUPAC (2S)-2-amino-4-[2-(1,2,5-dithiazepan-5-yl)-2-oxoethoxy]butanoic acid) (Boll et al., Org Lett (2012), 14(9): 2222-2225). However, the biosynthesis of methionine analogues as shown and provided herein in context with the present invention is independent of their incorporation into a target protein.

In one embodiment of the present invention, the methionine analogues as prepared in accordance with the present invention may be selected from the group consisting of S-allyl-L-homocysteine ((2S)-2-amino-4-(prop-2-en-1-ylsulfanyl)butanoic acid; Sen or Sahc), S-propargyl-L-homocysteine (Syn), S-furyl-L-homocysteine (Fur), S-furfuryl-L-homocysteine (SFur), O-furfuryl-L-homoserine (OFur), O-allyl-L-homoserine (Oen), O-propargyl-L-homoserine (O-propargyloxy-L-homoserine, Oyn), L-azidohomoalanine (Aha), S-azidopropyl-L-homocysteine (Saz or SN₃), O-norbornenemethoxy-L-homoserine ((2S)-2-amino-4-(bicyclo[2.2.1]hept-5-en-2-ylmethoxy)butanoic acid; Nom), O-norbornenoxy-L-homoserine ((2S)-2-amino-4-(bicyclo[2.2.1]hept-5-en-2-yloxy)butanoic acid; Nor), O-(2-oxopropoxy)-L-homoserine ((2S)-2-amino-4-(2-oxopropoxy)butanoic acid; Opo), O-(3-oxobutoxy)-L-homoserine ((2S)-2-amino-4-(3-oxobutoxy)butanoic acid; Obo), and O-[2-(1,2,5-dithiazepan-5-yl)-2-oxoethoxy]-L-homoserine ((2S)-2-amino-4-[2-(1,2,5-dithiazepan-5-yl)-2-oxoethoxy]butanoic acid, SEA-Hse). In one specific embodiment of the present invention, the methionine analogues may be selected from the group consisting of S-allyl-L-homocysteine (Sen or Sahc), S-propargyl-L-homocysteine (Syn), S-furyl-L-homocysteine (Fur), S-furfuryl-L-homocysteine (SFur), O-furfuryl-L-homoserine (OFur), O-allyl-L-homoserine (Oen), O-propargyl-L-homoserine (O-propargyloxy-L-homoerine) (Oyn), L-azidohomoalanine (Aha), S-azidopropyl-L-homocysteine (Saz or SN₃), O-(3-oxobutoxy)-L-homoserine ((2S)-2-amino-4-(3-oxobutoxy)butanoic acid (Obo), and O-norbornenoxy-L-homoserine ((2S)-2-amino-4-(bicyclo[2.2.1]hept-5-en-2-yloxy)butanoic acid (Nor). In a further specific embodiment of the present invention, the methionine analogues may be selected from the group consisting of S-allyl-L-homocysteine (Sen or Sahc), S-propargyl-L-homocysteine (Syn), S-furfuryl-L-homocysteine (SFur), O-allyl-L-homoserine (Oen), O-propargyl-L-homocysteine (O-propargyloxy-L-homocysteine) (Oyn), L-azidohomoalanine (Aha), S-azidopropyl-L-homocysteine (Saz or SN₃), O-(3-oxobutoxy)-L-homoserine ((2S)-2-amino-4-(3-oxobutoxy)butanoic acid (Obo), O-[2-(1,2,5-dithiazepan-5-yl)-2-oxoethoxy]-L-homoserine ((2S)-2-amino-4-[2-(1,2,5-dithiazepan-5-yl)-2-oxoethoxy]butanoic acid, SEA-Hse) and O-norbornenoxy-L-homoserine ((2S)-2-amino-4-(bicyclo[2.2.1]hept-5-en-2-yloxy)butanoic acid (Nor), or specifically the group consisting of S-allyl-L-homocysteine (Sen or Sahc), S-propargyl-L-homocysteine (Syn), S-furfuryl-L-homocysteine (SFur), O-allyl-L-homocysteine (Oen), O-propargyl-L-homocysteine (O-propargyloxy-L-homocysteine) (Oyn), L-azidohomoalanine (Aha), O-(3-oxobutoxy)-L-homoserine ((2S)-2-amino-4-(3-oxobutoxy)butanoic acid (Obo), O-[2-(1,2,5-dithiazepan-5-yl)-2-oxoethoxy]-L-homoserine ((2S)-2-amino-4-[2-(1,2,5-dithiazepan-5-yl)-2-oxoethoxy]butanoic acid, SEA-Hse) and O-norbornenoxy-L-homoserine ((2S)-2-amino-4-(bicyclo[2.2.1]hept-5-en-2-yloxy)butanoic acid (Nor), particularly S-propargyl-L-homocysteine (Syn), O-propargyl-L-homoserine (O-propargyloxy-L-homocysteine) (Oyn), L-azidohomoalanine (Aha), O-(3-oxobutoxy)-L-homoserine ((2S)-2-amino-4-(3-oxobutoxy)butanoic acid (Obo), O-[2-(1,2,5-dithiazepan-5-yl)-2-oxoethoxy]-L-homoserine ((2S)-2-amino-4-[2-(1,2,5-dithiazepan-5-yl)-2-oxoethoxy]butanoic acid, SEA-Hse) and O-norbornenoxy-L-homoserine ((2S)-2-amino-4-(bicyclo[2.2.1]hept-5-en-2-yloxy)butanoic acid (Nor).

As described herein, the methionine analogues are synthesized by OAHS which converts O-acetyl-L-homoserine (synthesized via HSAT from homoserine as known in the art and shown herein) together with a nucleophile to the desired methionine analogue. The methionine analogues differ in the respective moiety in their side chains, were such moieties may be, e.g., azido, alkyne, alkene, keto/aldehyde, norbornene, or furan moieties. The resulting moiety depends on the specific nucleophile which is converted by OAHS together with O-acetyl-L-homoserine to the desired methionine analogue. As set forth herein, all suitable nucleophiles may be used in context with the present invention, Including those with unsaturated side chains and ring systems. In one embodiment of the present invention, the nucleophile used for producing the methionine analogue may be selected from the group consisting of thiols, thioesters (e.g., thioacetates), selenols, selenoacetates, norbornene, alcohols, azides, cyanides and amines. In a further embodiment in this context, the OAHS may be derived from *Geobacillus stearothermophilus* (for example, genbank accession no. E16859.1; Omura et al., J Biosci Bioeng (2003), 96(1): 53-58). In a specific embodiment, the nucleophiles may be selected from thioesters (e.g., thioacetates), norbornene, alcohols, and azides.

Generally, as used herein, the term "nucleophile" comprises both, the actual nucleophile as well as precursors which are converted in the cell to actual nucleophiles. For example, S-allyl thioacetate as nucleophile precursor is termed herein as nucleophile and is converted in the cell to allyl mercaptan (the actual nucleophile). Likewise, S-propargyl thioacetate as nucleophile precursor is termed herein as nucleophile and is converted in the cell to propargyl mercaptan (the actual nucleophile).

In one embodiment of the present invention, the nucleophile to be used as described herein may be selected from the group consisting of allylthiol (allyl mercaptan, 2-propene-1-thiol), S-allyl thioacetate (S-prop-2-en-1-yl ethanethioate), propargyl mercaptan (2-propyne-1-thiol), S-propargyl thioacetate (S-prop-2-yn-1-yl ethanethioate), 3-azidopropane-1-thiol, S-(3-azidopropyl)thioacetate (S-(3-azidopropyl) ethanethioate), 2-propene-1-selenol, Se-allyl selenoacetate, allyl alcohol (2-propen-1-ol), propargyl alcohol (2-propyn-1-ol), furanthiol, 3-furanmethanethiol, 5-norbornene-2-methanol (bicyclo[2.2.1]hept-5-en-2-ylmethanol), 5-norbornen-2-ol (bicyclo[2.2.1]hept-5-en-2-ol), sodium azide, sodium cyanide, hydroxyacetone (1-hydroxypropan-2-one), 4-hydroxybutan-2-one, 1-(1,2,5-dithiazepan-5-yl)-2-hydroxyethanone, norbornen, and furan. In a specific embodiment of the present invention, the nucleophile to be used as described herein may be selected from the group consisting of allylthiol (allyl mercaptan, 2-propene-1-thiol), propargyl mercaptan (2-propyne-1-thiol), 3-azidopropane-1-thiol, allyl alcohol (2-propen-1-ol), propargyl alcohol (2-propyn-1-ol), 5-norbornene-2-methanol (bicyclo[2.2.1]hept-5-en-2-ylmethanol), 5-norbornen-2-ol (bicyclo[2.2.1]hept-5-en-2-ol), and furanthiol. In this context, as an example of the present invention, the OAHS may be derived from *Geobacillus stearothermophilus* (for example, genbank accession no. E16859.1 (Omura et al., J Biosci Bioeng (2003), 96(1): 53-58).

The skilled person is readily able to identify the suitable nucleophile to produce a corresponding desired methionine analogue. Specific embodiments of the present invention for choosing nucleophiles for producing specific methionine analogues are provided in Table 1 below, the respective compounds are depicted in FIG. 4 and resulting methionine analogues in FIG. 5.

Figure 4:
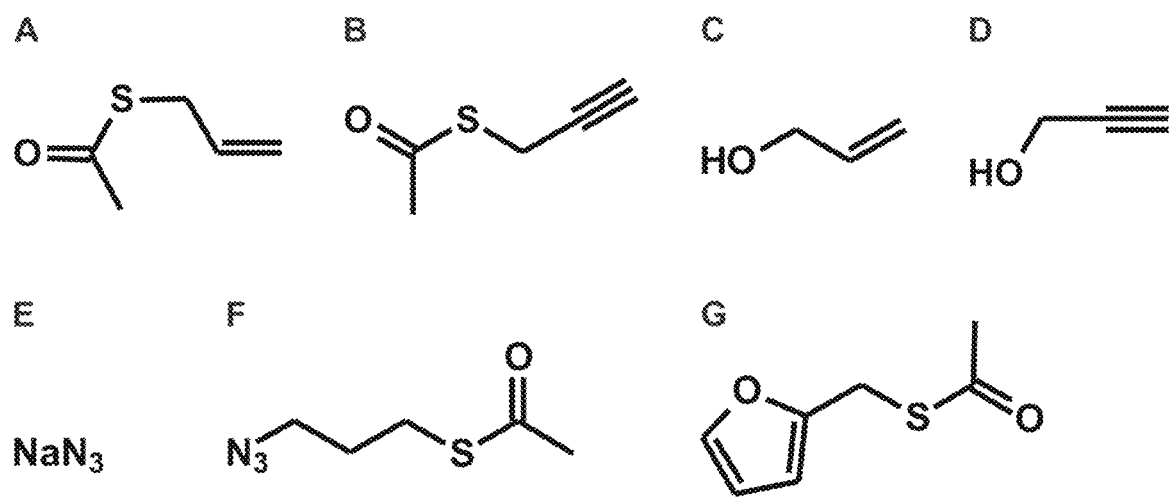

TABLE 1 correspond to the respective structures of the nucleophile and resulting methionine analogue, respectively, as shown in FIGS. 4 and 5.

| # | Substrate/ nucleophile | functionality | Mw [g/mol] | Methionine analogue | Mw [g/mol] | $t_R$ [min][1] |
|---|---|---|---|---|---|---|
| A | S-allyl thioacetate | alkene | 116.18 | Sen-S-allyl-L-homocysteine | 175.25 | 7.062 |
| B | S-propargyl thioacetate | alkyne | 114.16 | Syn-S-propargyl-L-homocysteine | 173.24 | 6.749 |
| C | Allyl alcohol | alkene | 58.08 | Oen-O-allyl-L-homoserine | 159.18 | 6.768 |
| D | Propargyl alcohol | alkyne | 56.06 | Oyn-O-propargyl-L-homoserine | 157.18 | 5.075 |
| E | Sodium azide | azide | 65.00 | Aha-L-azido homoalanine | 144.13 | 3.695 |
| F | S-furfuryl thioacetate | furyl | 156.20 | SFur-S-furfuryl-L-homocysteine | 215.57 | 7.427 |
| G | S-(3-azido-propyl) thioacetate | azide | 159.21 | $SN_3$-S-azidopropyl-L-homocysteine | 218.28 | 7.427 |
| H | 5-norbornene-2-ol | norbornene | 110.15 | Nor-O-norbornenoxy-L-homoserine | 211.26 | 7.062[2] |
| I | exo-5-norbornene-2-methanol | norbornene | 124.18 | Nom-O-norbornene-methoxy-L-homoserine | 225.28 | 6.749[2] |

[1]substrates A and B were produced by chemical synthesis.
[2]chromatograms not shown.

In context with the present invention, the HSAT may be of any origin or kind, wherein it is preferably capable to convert homoserine to O-acetyl-L-homoserine. The corresponding enzymes and their abilities are known in the art, e.g., in Ma (2014), loc. cit., and Ma (2016), loc. cit. In one embodiment of the present invention, the HSAT may be derived from, e.g., Deinococcus radiodurans or Mycobacterium smegmatis. In a specific embodiment, the HSAT is derived from Deinococcus radiodurans (for example, genbank accession no. Q9RVZ8). In one embodiment of the present invention, the amino acid sequences of an HSAT derived from Deinococcus radiodurans (for example, genbank accession no. Q9RVZ8) is shown in SEQ ID NO: 2, and that of Mycobacterium smegmatis is shown in SEQ ID NO: 3, respectively. Accordingly, in one embodiment of the present invention, an HSAT may be derived from Deinococcus radiodurans and may have an amino acid sequence as shown in SEQ ID NO: 2, and/or an HSAT may be derived from Mycobacterium smegmatis and may have an amino acid sequence as shown in SEQ ID NO: 3. In context with the present invention, an HSAT derived from Deinococcus radiodurans may have an amino acid sequence as shown in SEQ ID NO: 2, or a sequence having up to 50, 45, 40, 35, 30, 25, 20, 15, 12, 10, 9, 8, 7, 6, 5, 4, 3, 2 or 1 amino acid deviations (substitutions, additions, insertions and/or deletions) compared to the amino acid sequence of SEQ ID NO: 2, provided it is able to convert homoserine to O-acetyl-L-homoserine. As another example in context with the present invention, an HSAT derived from Mycobacterium smegmatis may have an amino acid sequence as shown in SEQ ID NO: 3, or a sequence having up to 50, 45, 40, 35, 30, 25, 20, 15, 12, 10, 9, 8, 7, 6, 5, 4, 3, 2 or 1 amino acid deviations (substitutions, additions, insertions, and/or deletions) compared to the amino acid sequence of SEQ ID NO: 3, provided it is able to convert homoserine to O-acetyl-L-homoserine. In a specific embodiment, the HSAT is derived from Deinococcus radiodurans and has an amino acid sequence as shown in SEQ ID NO: 2.

As a specific example of the present invention, the methionine analogue may be S-allyl-L-homocysteine (Sen) and is produced in accordance with the method of the present invention starting from L-homoserine. L-homoserine is then acetylated by the acetyl-CoA dependent enzyme L-homoserine-O-acetyltransferase (HSAT) e.g., derived from Deinococcus radiodurans. The resulting O-acetyl-L-homoserine is then converted to the methionine analog catalyzed by the O-acetyl-L-homoserine sulfhydrylase (OAHS) from Geobacillus stearothermophilus. Depending on which nucleophile is supplemented, different methionine analogs can be produced. For example, in context with the present invention, allylthiol (allyl mercaptan) may be used as the substrate to biosynthesize S-allyl-L-homocysteine, Sen; cf. also exemplary biosynthesis cascade depicted in FIG. 1. Further examples of methionine analogues to be produced in accordance with the present invention and corresponding nucleophiles are shown in FIG. 7.

One advantage of the present invention is, that the methionine analogues prepared in accordance with the present invention can not only be incorporated into a protein in a residue-specific manner (i.e. dependent on the respective residue of the non-canonical amino acid), but also in a site-specific manner), i.e. in a specific site within a given sequence).

The methionine analogues produced as described herein in accordance with the present invention may be incorporated into proteins. Accordingly, in one embodiment of the present inventions, the methionine analogue is incorporated into a protein during protein biosynthesis (e.g., during ribosomal translation). That is, the present invention also relates to a method for preparing a protein comprising a methionine analogue as described herein and to be produced in accordance with the present invention. The present invention also relates to proteins comprising such methionine analogues.

Accordingly, the present invention encompasses a protein comprising such methionine analogues, wherein said protein is obtainable by (or, in the alternate, is obtained by) the methods of the present invention. In particular, a protein comprising such methionine analogues is obtainable by (or, in the alternate, is obtained by) by a method as described herein, wherein in a further step a methionine analogue as described herein is incorporated into a protein during protein biosynthesis.

A protein comprising one or more, e.g., one, two, three, four, five, six, seven, eight, nine, ten or more, methionine analogues is thus preferably characterized in that said one or more methionine analogues have the following structural formula:

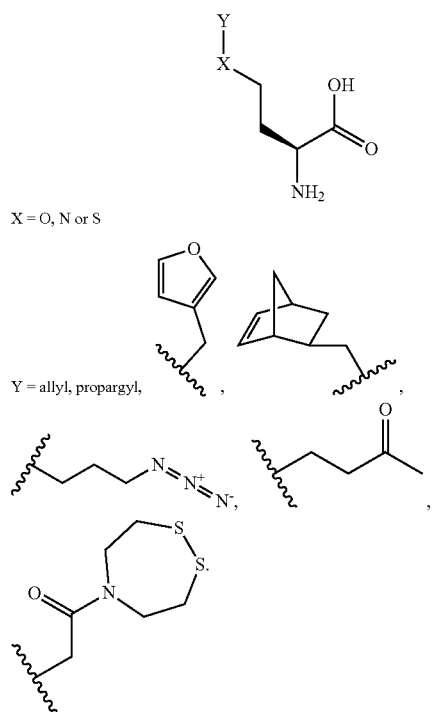

More preferably, a protein comprising one or more, e.g., one, two, three, four, five, six, seven, eight, nine, ten or more, methionine analogues is characterized in that said one or more methionine analogues comprise an azido, alkyne, alkene, norbornene, keto, aldehyde or furan moiety in its side chain.

Most preferably, a protein comprising one or more, e.g., one, two, three, four, five, six, seven, eight, nine, ten or more, methionine analogues is characterized in that said one or more methionine analogues is selected from the group consisting of S-allyl-L-homocysteine (Sen or Sahc), S-propargyl-L-homocysteine (Syn), S-furyl-L-homocysteine (Fur), S-furfuryl-L-homocysteine (SFur), O-furfuryl-L-homoserine (OFur), O-allyl-L-homoserine (Oen), O-propargyl-L-homoserine (O-propargyloxy-L-homoserine; Oyn), L-azidohomoalanine (Aha), S-azidopropyl-L-homocysteine (Saz or SN$_3$), norbornenemethoxy-L-homoserine ((2S)-2-amino-4-(bicyclo[2.2.1]hept-5-en-2-ylmethoxy)butanoic acid), and norbornenoxy-L-homoserine ((2S)-2-amino-4-(bicyclo[2.2.1]hept-5-en-2-yloxy)butanoic acid), whereby S-furyl-L-homocysteine (Fur), S-furfuryl-L-homocysteine (SFur), O-furfuryl-L-homoserine (OFur), O-allyl-L-homoserine (Oen), O-propargyl-L-homoserine (O-propargyloxy-L-homoserine, Oyn), L-azidohomoalanine (Aha), S-azidopropyl-L-homocysteine (Saz or SN), norbornenemethoxy-L-homoserine ((2S)-2-amino-4-(bicyclo[2.2.1]hept-5-en-2-ylmethoxy)butanoic acid), norbornenoxy-L-homoserine ((2S)-2-amino-4-(bicyclo[2.2.1]hept-5-en-2-yloxy)butanoic acid), O-(2-oxopropoxy)-L-homoserine (Opo), O-(3-oxobutoxy)-L-homoserine (Obo), O-[2-(1,2,5-dithiazepan-5-yl)-2-oxoethoxy]-L-homoserine ((2S)-2-amino-4-[2-(1,2,5-dithiazepan-5-yl)-2-oxoethoxy]butanoic acid, SEA-Hse) and S-allyl-L-cysteine (Sac) are being preferred.

Methods for preparing proteins including non-canonical amino acids are known in the art and described and exemplified herein (see, e.g., Wang et al., Science (2001), 292 (5516): 498-500; Hohsaka et al., J Biol Chem (2010), 6 (6): 809-815). As generally known in the art, aminoacyl tRNA synthetases (aaRS) are capable of attaching amino acids onto tRNAs cognate to the respective aaRS. As known in the art, "cognate tRNA" may mean that such tRNA is usually specifically recognized or preferred by the respective corresponding aaRS. This attachment step corresponds to an esterification step which is catalyzed by the aaRS, so that the respective tRNA is charged (or aminoacylated, attached, linked, loaded, etc.) with the respective amino acid to form an aminoacyl-tRNA. Accordingly, this attachment step may also be referred to as charging, loading, esterification, aminoacylation, or the like as understood by the person of skill in the art. tRNAs comprise an anticodon which are capable of identifying corresponding codons on the mRNA, usually either specific/base-by-base, or by wobble base pairing as known in the art. Also, as known in the art, usually tRNAs are specific for or prefer a particular amino acid with which the cognate tRNA may be charged by a corresponding aaRS.

The present invention further relates to a host cell encoding and stably expressing a L-homoserine-O-acetyl-transferase (HSAT) and an O-acetyl-L-homoserine sulfhydrylase (OAHS) as described herein. The host cell to be used in accordance with the present invention may be any kind of host cell, including eukaryotic or prokaryotic, as long as it encodes and is able to stably express HSAT and OAHS proteins. In context with the present invention, it is not necessary that the host cell naturally expresses a HSAT and/or OAHS. In one embodiment, the host cell used in accordance with the present invention does not express OAHS, in a further embodiment it neither expresses HSAT. In one embodiment, the host cell of the present invention may be a representative of Enterobacteriaceae (e.g., *Escherichia coli*), *Pichia* sp. (e.g., *Pichia pastoris*), a mammal cell (e.g., CHO or HEK) or a yeast (e.g., *S cerevisiae*), for example *E. coli*.

In one embodiment of the present invention, the host cell described and provided herein encodes and stably expresses OAHS derived from *Geobacillus stearothermophilus* (for example, genbank accession no. E16859.1; Omura et al., J Biosci Bioeng (2003), 96(1): 53-58). In one embodiment of the present invention, the OAHS has the amino acid sequence as shown in SEQ ID NO: 1, or a sequence having up to 50, 45, 40, 35, 30, 25, 20, 15, 12, 10, 9, 8, 7, 6, 5, 4, 3, 2 or 1 amino acid deviations (substitutions, additions, and/or deletions) compared to the amino acid sequence of SEQ ID NO: 1, provided it is able to convert O-acetyl-L-homoserine (together with a nucleophile as described herein) to a methionine analogue as described and exemplified herein.

In one embodiment of the present invention, the host cell described and provided herein encodes and stably expresses HSAT derived from *Deinococcus radiodurans* or *Mycobacterium smegmatis*. In a specific embodiment, the host cell described and provided herein encodes and stably expresses HSAT is derived from *Deinococcus radiodurans* (for example, genbank accession no. Q9RVZ8). In one embodiment of the present invention, the amino acid sequences of an HSAT derived from *Deinococcus radiodurans* (for example, genbank accession no. Q9RVZ8) is shown in SEQ ID NO: 2, and that of *Mycobacterium smegmatis* is shown in SEQ ID NO: 3, respectively. Accordingly, in one embodiment of the present invention, an HSAT may be derived from *Deinococcus radiodurans* and may have an amino acid sequence as shown in SEQ ID NO: 2, and/or an HSAT may be derived from *Mycobacterium smegmatis* and may have an amino acid sequence as shown in SEQ ID NO: 3. In context with the present invention, an HSAT derived from *Deinococcus radiodurans* may have an amino acid sequence as shown in SEQ ID NO: 2, or a sequence having up to 50, 45, 40, 35, 30, 25, 20, 15, 12, 10, 9, 8, 7, 6, 5, 4, 3, 2 or 1 amino acid deviations (substitutions, additions, and/or deletions) compared to the amino acid sequence of SEQ ID NO: 2, provided it is able to convert homoserine to O-acetyl-L-homoserine. As another example in context with the present invention, an HSAT derived from *Mycobacterium smegmatis* may have an amino acid sequence as shown in SEQ ID NO: 3, or a sequence having up to 50, 45, 40, 35, 30, 25, 20, 15, 12, 10, 9, 8, 7, 6, 5, 4, 3, 2 or 1 amino acid deviations (substitutions, additions, insertions, and/or deletions) compared to the amino acid sequence of SEQ ID NO: 3, provided it is able to convert homoserine to O-acetyl-L-homoserine. In a specific embodiment, the HSAT is derived from *Deinococcus radiodurans* and has an amino acid sequence as shown in SEQ ID NO: 2.

The present invention further relates to the use of a host cell described and provided herein for preparing a methionine analogue as described herein. Such methionine analogues are preferably non-canonical amino acids. In one embodiment of the present invention, the methionine analogues are amino acids comprising an azido, alkyne, alkene, norbornene, keto, aldehyde or furan moiety in its side chain, preferably azido, alkyne, norbornene, or keto. In one embodiment of the present invention, the methionine analogues prepared in accordance with the use of the host cell of present invention may be selected from the group consisting of S-allyl-L-homocysteine ((2S)-2-amino-4-(prop-2-en-1-ylsulfanyl)butanoic acid; Sen or Sahc), S-propargyl-L-homocysteine (Syn), S-furyl-L-homocysteine (Fur), S-furfuryl-L-homocysteine (SFur), O-furfuryl-L-homoserine (OFur), O-allyl-L-homoserine (Oen), O-propargyl-L-homoserine (O-propargyloxy-L-homoserine, Oyn), L-azido-homoalanine (Aha), S-azidopropyl-L-homocysteine (Saz or SN$_3$), O-norbornenemethoxy-L-homoserine ((2S)-2-amino-4-(bicyclo[2.2.1]hept-5-en-2-ylmethoxy)butanoic acid; Nom), O-norbornenoxy-L-homoserine ((2S)-2-amino-4-(bicyclo[2.2.1]hept-5-en-2-yloxy)butanoic acid; Nor), O-(2-oxopropoxy)-L-homoserine ((2S)-2-amino-4-(2-oxopropoxy)butanoic acid; Opo), O-[2-(1,2,5-dithiazepan-5-yl)-2-oxoethoxy]-L-homoserine ((2S)-2-amino-4-[2-(1,2,5-dithiazepan-5-yl)-2-oxoethoxy]butanoic acid, SEA-Hse) and O-(3-oxobutoxy)-L-homoserine ((2S)-2-amino-4-(3-oxobutoxy)butanoic acid; Obo). In one specific embodiment of the present invention, the methionine analogues may be selected from the group consisting of S-allyl-L-homocysteine (Sen or Sahc), S-propargyl-L-homocysteine (Syn), S-furyl-L-homocysteine (Fur), S-furfuryl-L-homocysteine (SFur), O-furfuryl-L-homoserine (OFur), O-allyl-L-homoserine (Oen), O-propargyl-L-homoserine (O-propargyloxy-L-homoerine) (Oyn), L-azidohomoalanine (Aha), S-azidopropyl-L-homocysteine (Saz or SN$_3$), O-(3-oxobutoxy)-L-homoserine ((2S)-2-amino-4-(3-oxobutoxy)butanoic acid (Obo), O-[2-(1,2,5-dithiazepan-5-yl)-2-oxoethoxy]-L-homoserine ((2S)-2-amino-4-[2-(1,2,5-dithiazepan-5-yl)-2-oxoethoxy]butanoic acid, SEA-Hse) and O-norbornenoxy-L-homoserine ((2S)-2-amino-4-(bicyclo[2.2.1]hept-5-en-2-yloxy)butanoic acid (Nor). In a further specific embodiment of the present invention, the methionine analogues may be selected from the group consisting of S-allyl-L-homocysteine (Sen or Sahc), S-propargyl-L-homocysteine (Syn), S-furfuryl-L-homocysteine (SFur), O-allyl-L-homoserine (Oen), O-propargyl-L-homocysteine (O-propargyloxy-L-homocysteine) (Oyn), L-azidohomoalanine (Aha), S-azidopropyl-L-homocysteine (Saz or SN$_3$), O-(3-oxobutoxy)-L-homoserine ((2S)-2-amino-4-(3-oxobutoxy)butanoic acid (Obo), and O-norbornenoxy-L-homoserine ((2S)-2-amino-4-(bicyclo[2.2.1]hept-5-en-2-yloxy)butanoic acid (Nor), or specifically the group consisting of S-allyl-L-homocysteine (Sen or Sahc), S-propargyl-L-homocysteine (Syn), S-furfuryl-L-homocysteine (SFur), O-allyl-L-homocysteine (Oen), O-propargyl-L-homocysteine (O-propargyloxy-L-homocysteine) (Oyn), L-azidohomoalanine (Aha), O-(3-oxobutoxy)-L-homoserine ((2S)-2-amino-4-(3-oxobutoxy)butanoic acid (Obo), O-[2-(1,2,5-dithiazepan-5-yl)-2-oxoethoxy]-L-homoserine ((2S)-2-amino-4-[2-(1,2,5-dithiazepan-5-yl)-2-oxoethoxy]butanoic acid, SEA-Hse) and O-norbornenoxy-L-homoserine ((2S)-2-amino-4-(bicyclo[2.2.1]hept-5-en-2-yloxy)butanoic acid (Nor), particularly S-propargyl-L-homocysteine (Syn), O-propargyl-L-homocysteine (O-propargyloxy-L-homocysteine) (Oyn), L-azidohomoalanine (Aha), O-(3-oxobutoxy)-L-homoserine ((2S)-2-amino-4-(3-oxobutoxy)butanoic acid (Obo), and O-norbornenoxy-L-homoserine ((2S)-2-amino-4-(bicyclo[2.2.1]hept-5-en-2-yloxy)butanoic acid (Nor).

The embodiments which characterize the present invention are described herein, shown in the Figures, illustrated in the Examples, and reflected in the claims.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferably within 10%, and more preferably within 5% or 2% of a given value or range.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

All publications and patents cited throughout the text of this specification (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

The Figures show:

FIG. 1 Biosynthesis of methionine analogue via HSAT and OAHS in accordance with the present invention, example with allylthiol as nucleophile to produce S-allyl-L-homocysteine (Sen)

1: L-homoserine; 2: O-acetyl-L-homoserine; 3: Nucleophile (example 3a: allylthiol)—Depending on which nucleophile 3 is supplemented, different Met analogs can be produced in accordance with the present invention; 4: methionine analogue to be produced in accordance with the present invention (example 4a: Sen, S-allyl-L-homocysteine)

HSAT: L-homoserine-O-acetyltransferase; OAHS: O-acetyl-L-homoserine sulfhydrylase FIG. 2 Successful biosynthesis of Sen (S-allyl-L-homocysteine) In E. col. Times indicate hours of Sen biosynthesis.

Figure 3:
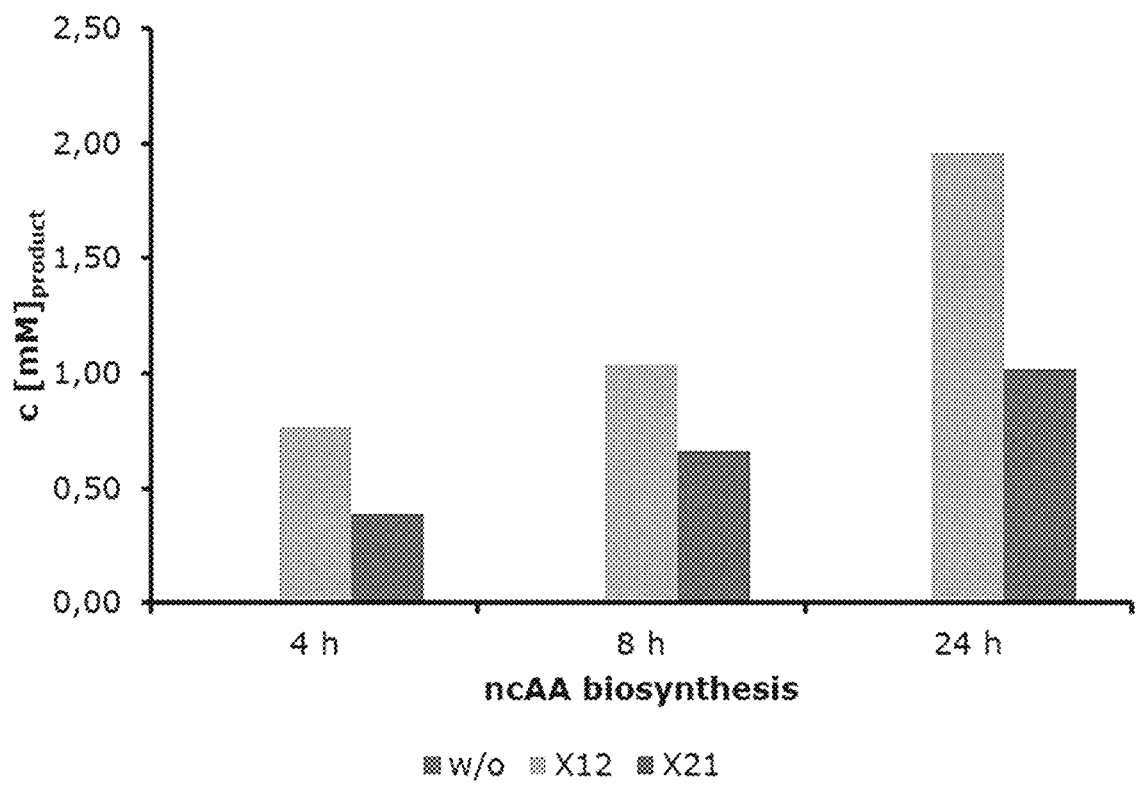

FIG. 3 HSAT (1) and OAHS (2) gene order impact on Sen-biosynthesis. Indication 5'→3'.

Gene order in polycistronic expression construct: X12, gene X (1$^{st}$ position), HSAT (2$^{nd}$ position), OAHS (3$^{rd}$ position); X21, gene X (1$^{st}$ position), OAHS (2$^{nd}$ position), HSAT (3$^{rd}$ position); gene X does not participate in Sen biosynthesis. Times indicate hours of Sen biosynthesis.

FIG. 4 Structures of the nucleophiles used for the biosynthesis of the reactive methionine analogues by the HSAT-OHAS cascade; cf. Table 1.

FIG. 5 Confirmation of the biosynthesis of different methionine analogs by HPLC-MS; structures, assignment to letters A-G, molecular weight and retention times cf. Table 1.

All retention times and masses were confirmed by chemically synthesized standards.

Figure 6:
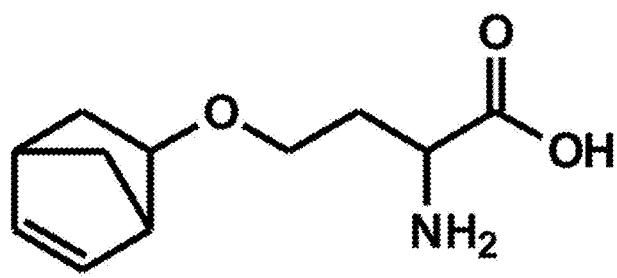
Figure 6:
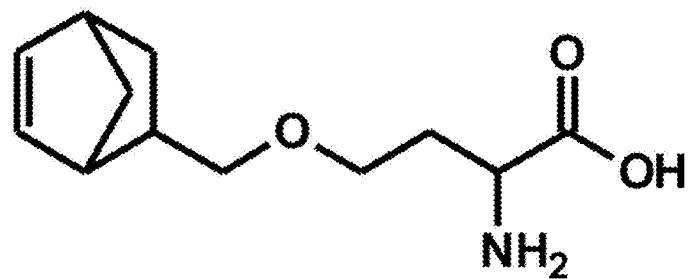

FIG. 6 A: S-norbornenoxy-L-homocysteine (Nor)
B: S-norbornenmethoxy-L-homocysteine (Nom)

Figure 8:
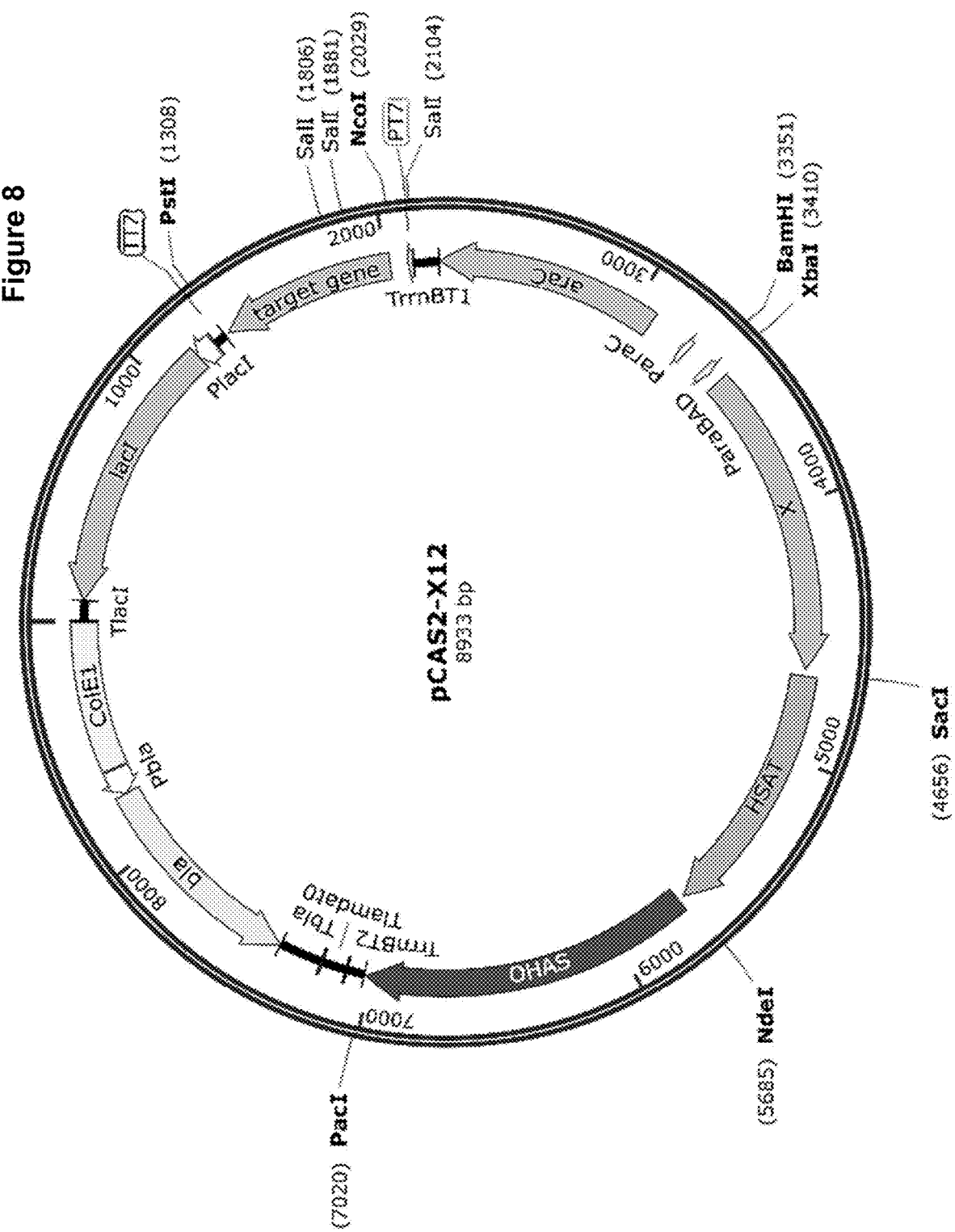

FIG. 7 Examples for suitable nucleophiles (also referred to herein and in the Figure as "precursor") and corresponding methionine analogues in accordance with the present invention FIG. 8 Plasmid 1 pCAS2-X12.

The L-homoserine O-acetyltransferase (HSAT, 1) and O-acetyl-L-homoserine sulfhydrylase (OHAS, 2) genes are under the control of an arabinose-inducible araBAD promoter ($P_{araBAD}$) and a combined rrnBT2 ($T_{rrnBT2}$) lamda $t_0$ ($T_{lamdat0}$) terminator. The target gene can be inserted at the NcoI/PstI sites to be under the control of an IPTG-inducible T7/lacO promoter ($P_{T7}$) and a T7 terminator (Tn). Alternatively, the PT7 promoter can be exchanged by using the SalI site. All genes carry the same RBS sequence from the pET21a(+) plasmid. Besides the parts already mentioned, the plasmid carries the lac repressor gene (lacI) with its own promoter ($P_{lacI}$) and terminator; as well as the ara repressor gene (araC) under its own promoter ($P_{araC}$) and an rrnBT1 terminator (TrrnBT1). It also contains the β-lactamase gene (bla) with its own promoter (Pbla) and terminator ($T_{bla}$) for plasmid maintenance; X, additional gene not participating in the synthesis of the Met analogs.

Figure 9:
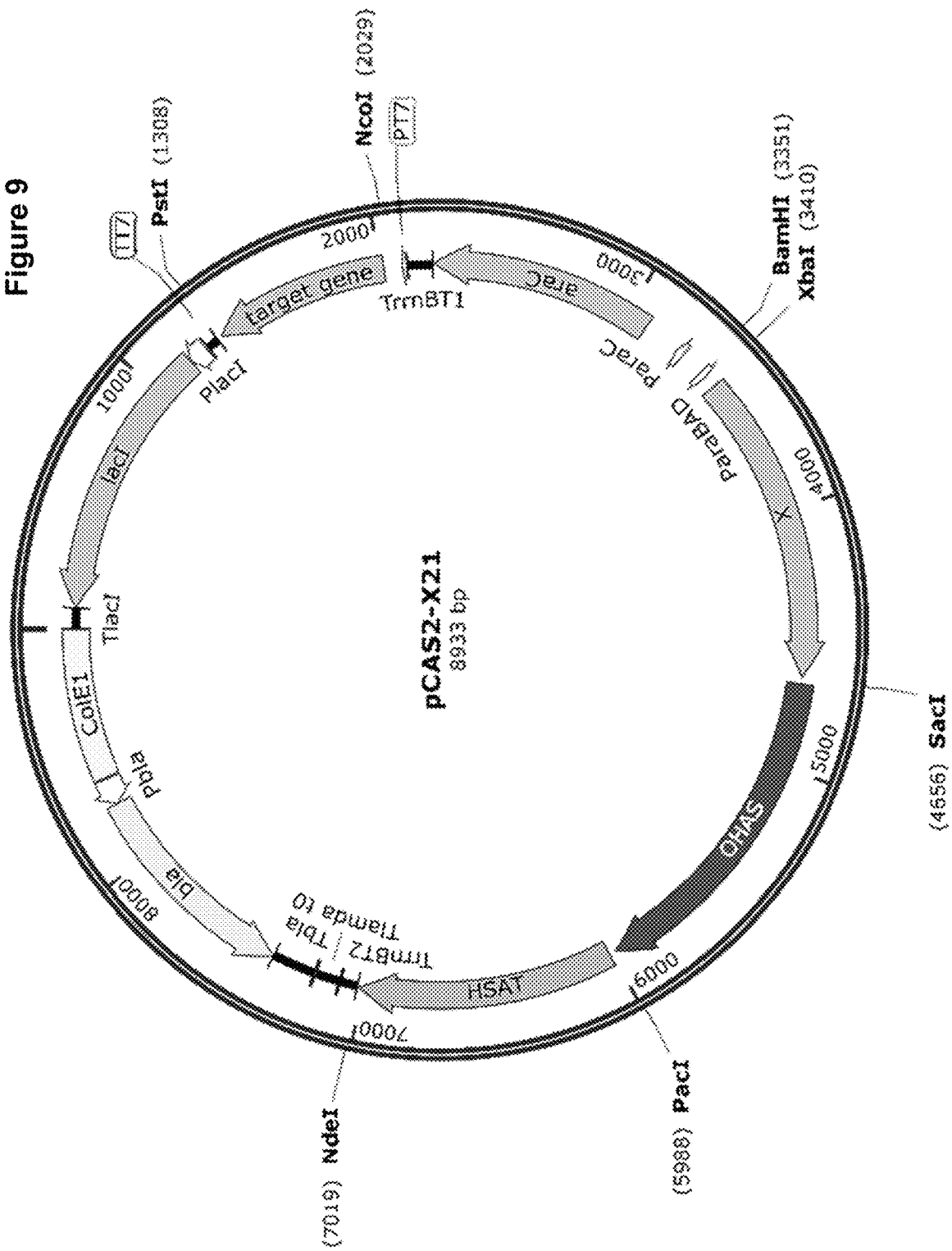

FIG. 9 Plasmid 2 pCAS2-X21.

The L-homoserine O-acetyltransferase (HSAT, 1) and O-acetyl-L-homoserine sulfhydrylase (OHAS, 2) genes are under the control of an arabinose-Inducible araBAD promoter ($P_{araBAD}$) and a combined rrnBT2 ($T_{rrnBT2}$) lamda $t_0$ ($T_{lamdat0}$) terminator. The target gene can be inserted at the NcoI/PstI sites to be under the control of an IPTG-inducible T7/lacO promoter ($P_{T7}$) and a T7 terminator ($T_{T7}$). Alternatively, the PT7 promoter can be exchanged by using the SalI site. All genes carry the same RBS sequence from the pET21a(+) plasmid. Besides the parts already mentioned, the plasmid carries the lac repressor gene (lacI) with its own promoter ($P_{lacI}$) and terminator; as well as the are repressor gene (araC) under its own promoter ($P_{araC}$) and an rrnBT1 terminator (TrrnBT1). It also contains the β-lactamase gene (bla) with its own promoter (Pbla) and terminator ($T_{bla}$) for plasmid maintenance; X, additional gene not participating in the synthesis of the Met analogs.

Figure 10:
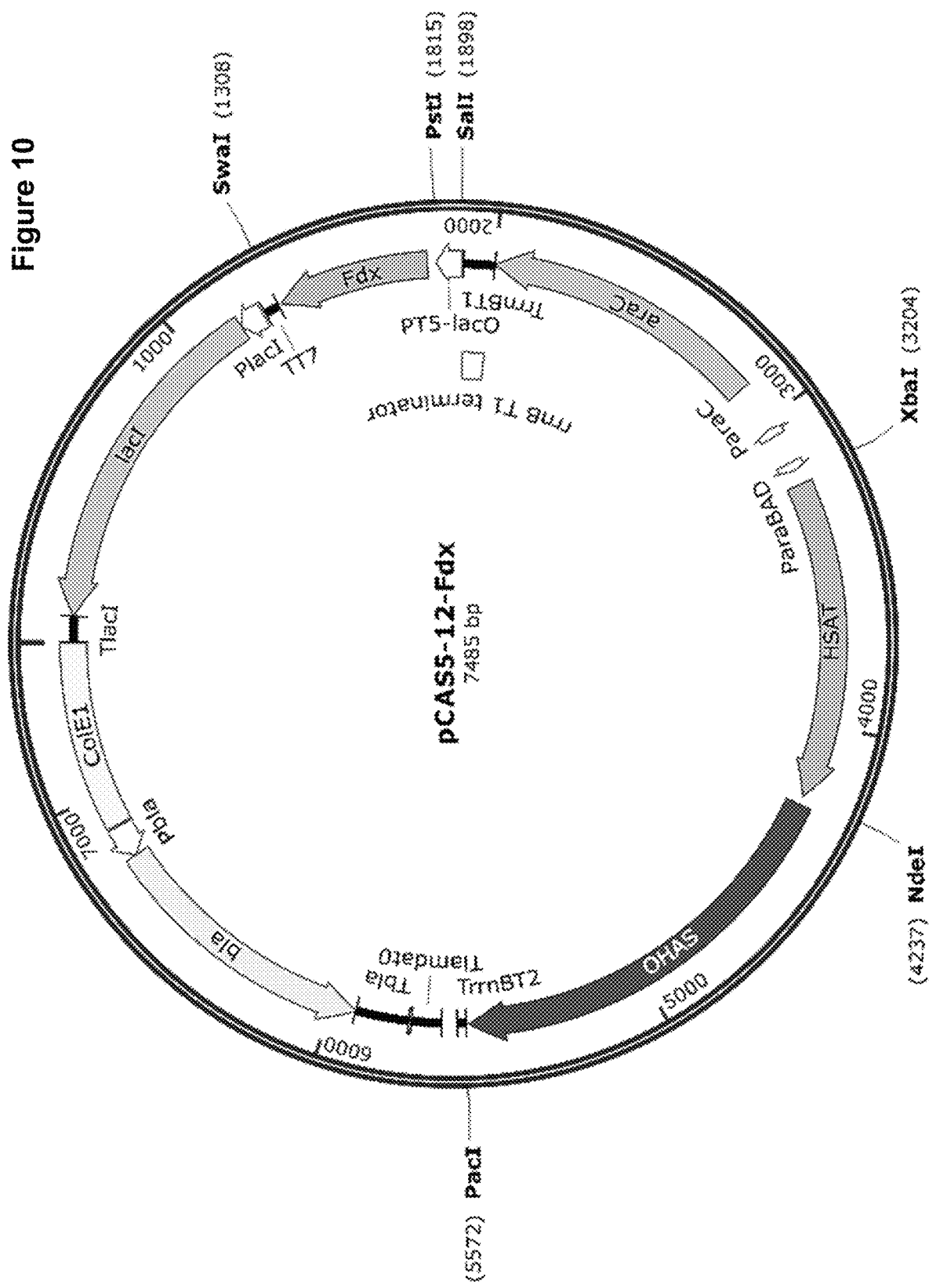

FIG. 10 Plasmid 3 pCAS5-12-Fdx.

The L-homoserine O-acetyltransferase (HSAT, 1) and O-acetyl-L-homoserine sulfhydrylase (OHAS, 2) genes are under the control of an arabinose-inducible araBAD promoter ($P_{araBAD}$) and a combined rrnBT2 ($T_{rrnBT2}$) lamda $t_0$ ($T_{lamdat0}$) terminator. The target gene flavodoxin (Fdx) is under the control of an IPTG inducible PT5-lacO ($P_{T5-lacO}$) promoter. The Fdx carries a N-terminal StrepII-tag and a C-terminal hexahistidine-tag for affinity chromatography. Besides the parts already mentioned, the plasmid carries the lac repressor gene (lacI) with its own promoter ($P_{lacI}$) and terminator; as well as the ara repressor gene (araC) under its own promoter ($P_{araC}$) and an rrnBT1 terminator (TrrnBT1). It also contains the β-lactamase gene (bla) with its own promoter (Pbla) and terminator ($T_{bla}$) for plasmid maintenance.

Figure 11:
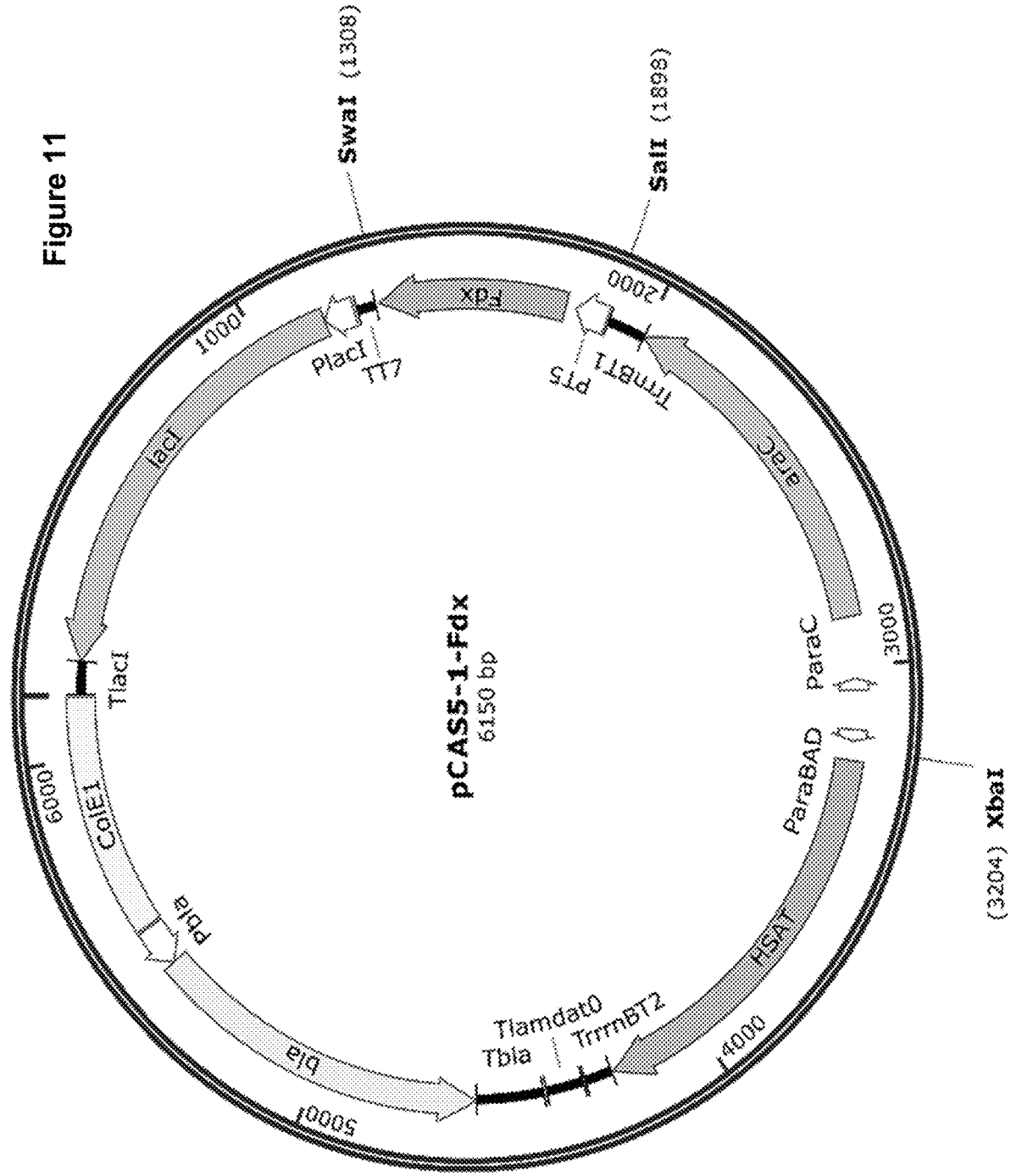

FIG. 11 Plasmid 4 pCAS5-1-Fdx.

The L-homoserine O-acetyltransferase (HSAT, 1) gene is under the control of an arabinose-inducible araBAD promoter ($P_{araBAD}$) and a combined rrnBT2 ($T_{rrnBT2}$) lamda $t_0$ ($T_{lamdat0}$) terminator. The target gene flavodoxin (Fdx) is under the control of an IPTG inducible PT5-lacO ($P_{T5-lacO}$) promoter. The Fdx carries a N-terminal StrepII-tag and a C-terminal hexahistidine-tag for affinity chromatography. Besides the parts already mentioned, the plasmid carries the lac repressor gene (lacI) with its own promoter ($P_{lacI}$) and terminator; as well as the ara repressor gene (araC) under its own promoter ($P_{araC}$) and an rrnBT1 terminator (TrrnBT1). It also contains the β-lactamase gene (bla) with its own promoter (Pbla) and terminator ($T_{bla}$) for plasmid maintenance.

Figure 12A:
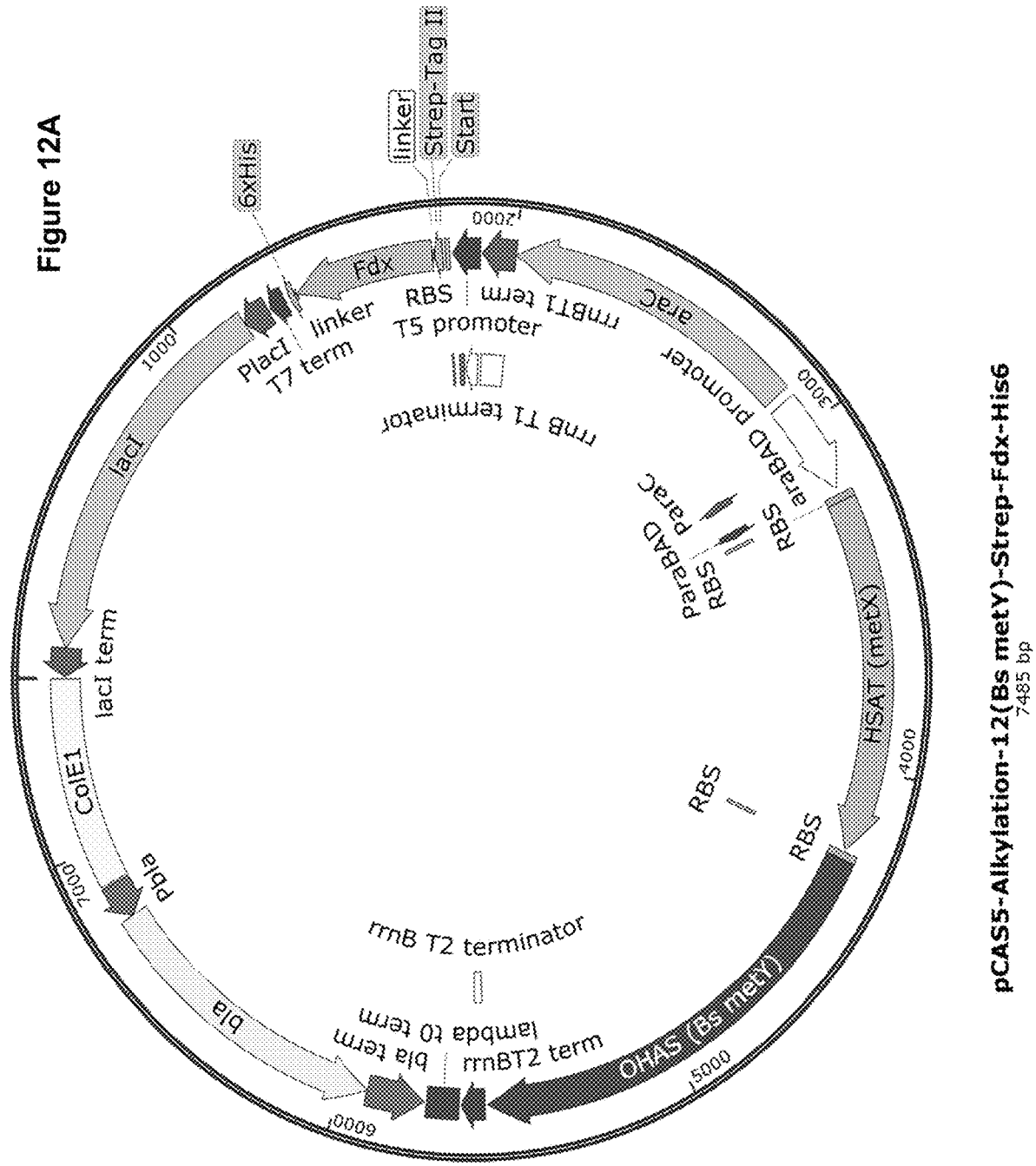
Figure 12B:
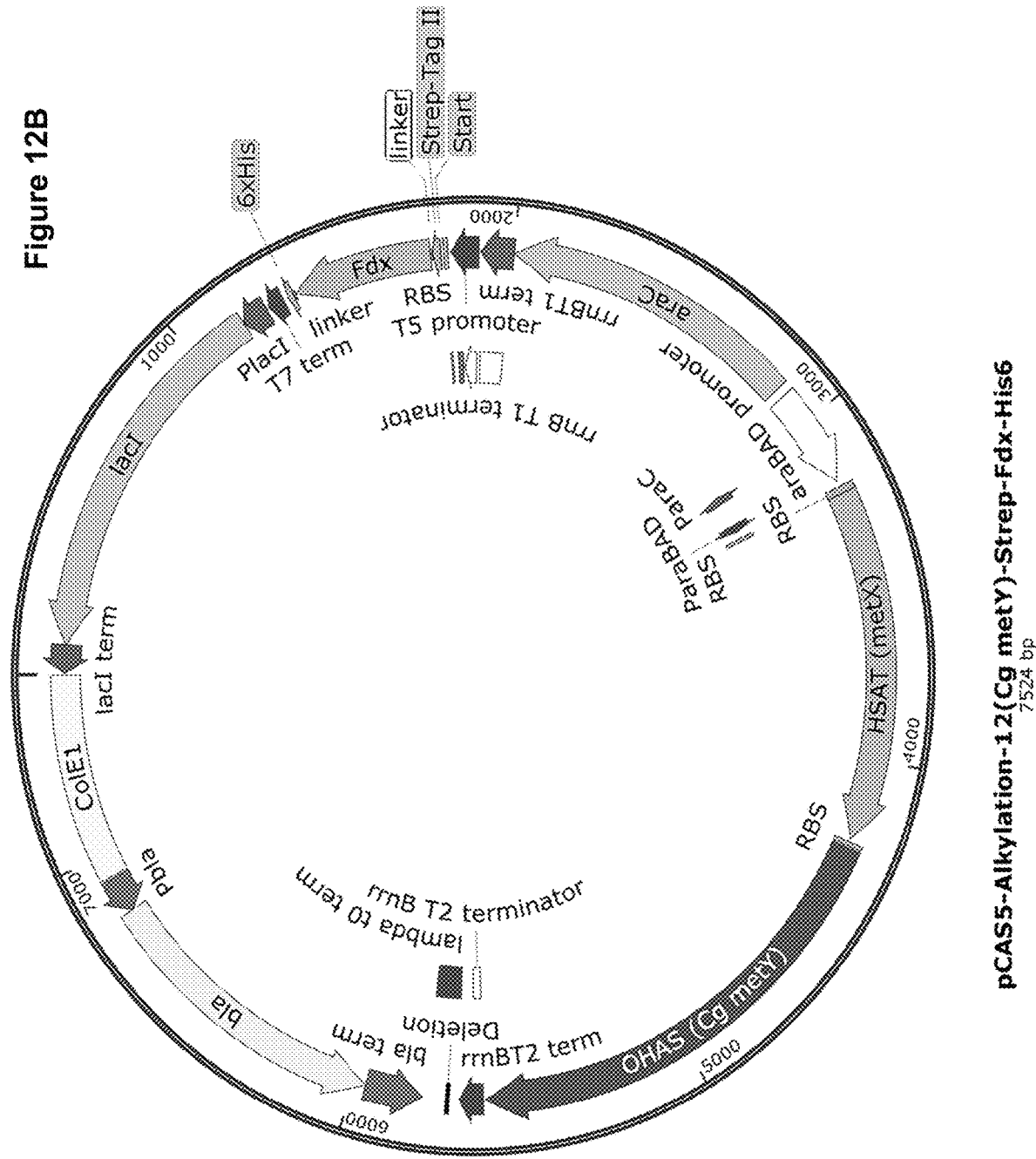

FIG. 12 Plasmids pCAS5-Alkylation-12(Bs metY)-Strep-Fdx-His6 and pCAS5-Alkylation-12(Cg metY)-Strep-Fdx-His6

The L-homoserine O-acetyltransferase (HSAT, 1) and O-acetyl-L-homoserine sulfhydrylase (OHAS, 2) genes are under the control of an arabinose-inducible araBAD promoter ($P_{araBAD}$) and a combined rrnBT2 ($T_{rrnBT2}$) lamda $t_0$ ($T_{lamdat0}$) terminator. OHAS is derived from *Bacillus stearothermophilus* CN3 (Bs metY) or *Corynebacterium glutamicum* (Cg metY), respectively. The target gene flavodoxin (Fdx) is under the control of an IPTG inducible PT5-lacO ($P_{T5-lacO}$) promoter. The Fdx carries a N-terminal StrepII-tag and a C-terminal hexahistidine-tag for affinity chromatography. Besides the parts already mentioned, the plasmid carries the lac repressor gene (lacI) with its own promoter ($P_{lacI}$) and terminator; as well as the are repressor gene (araC) under its own promoter ($P_{araC}$) and an rrnBT1 terminator (TrrnBT1). It also contains the β-lactamase gene (bla) with its own promoter ($P_{bla}$) and terminator ($T_{bla}$) for plasmid maintenance.

Figure 13:
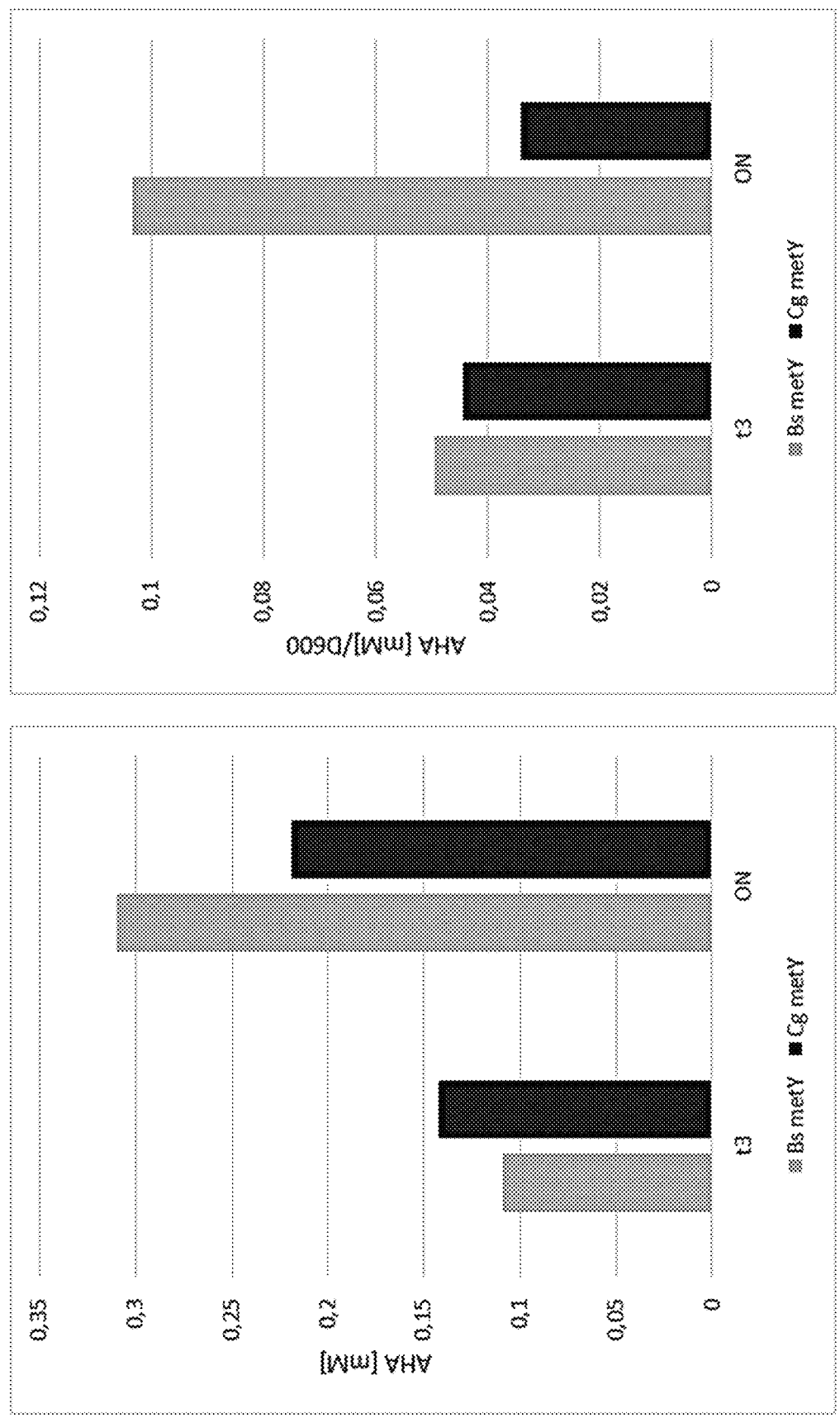

FIG. 13 Comparison of AHA concentration in culture supernatant in mM and in mM normalized to cell density (mM/$D_{600}$) of Bs metY (gray) and Cg metY (black) after 3 h of induction (t3) and ON incubation (ON) (cf. Example 3).

Figure 14:
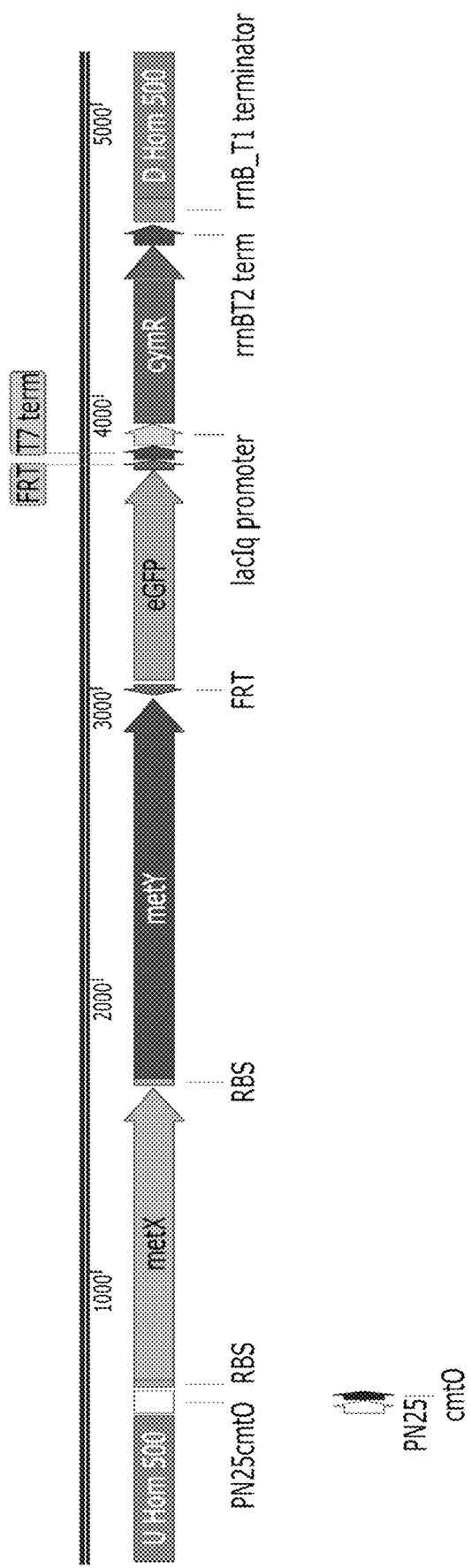

FIG. 14 Integration cassette of the cascade enzymes metXY and the eGFP reporter. U Hom 500, upstream 500 bp homology to the melAB locus, cascade enzyme sequences metX, metY and the reporter protein sequence eGFP flanked with FRT sites under the cumate inducible promoter $P_{N25cmIO}$ followed by the regulator protein sequence cymR under the strong constitutive promoter lacI$^q$ and D Hom 500, downstream 500 bp homology to the melAB locus.

Figure 15:
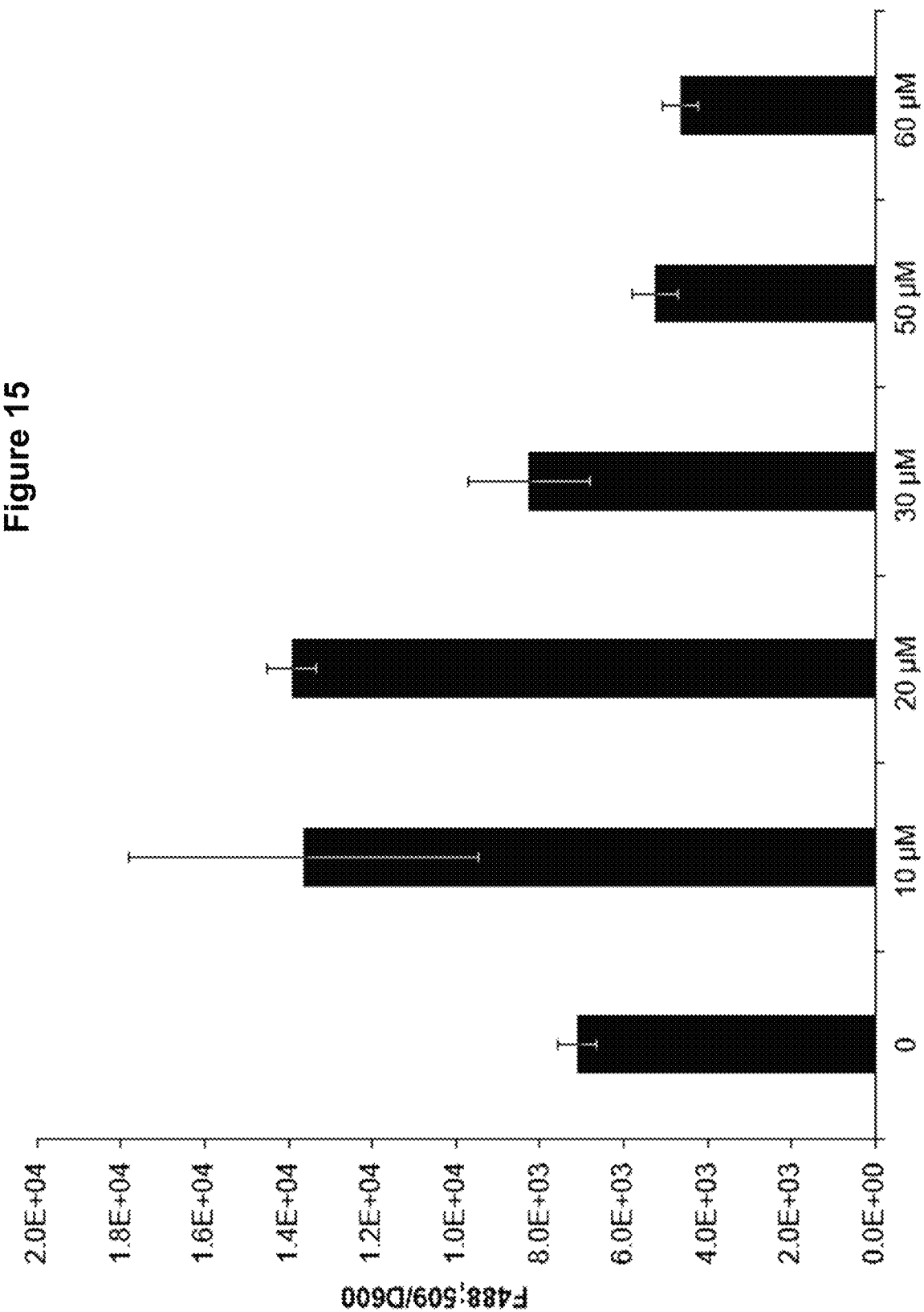

FIG. 15 Test expression of eGFP from the pTarget plasmid. BL21 {pMel (500) metXY-FRT>eGFP>FRT$_{lacI}^q$-cymR} cells were grown in M9 medium. The cells were induced with 0-60 μM cumate. Fluorescence measurement was performed after overnight incubation. Cells were diluted 1:5 with 1×PBS buffer. Fluorescence units were correlated to the cell density ($F_{488/508}/D_{600}$) and the average of seven technical replicates is shown. The error bars indicate the standard deviation.

Figure 16:
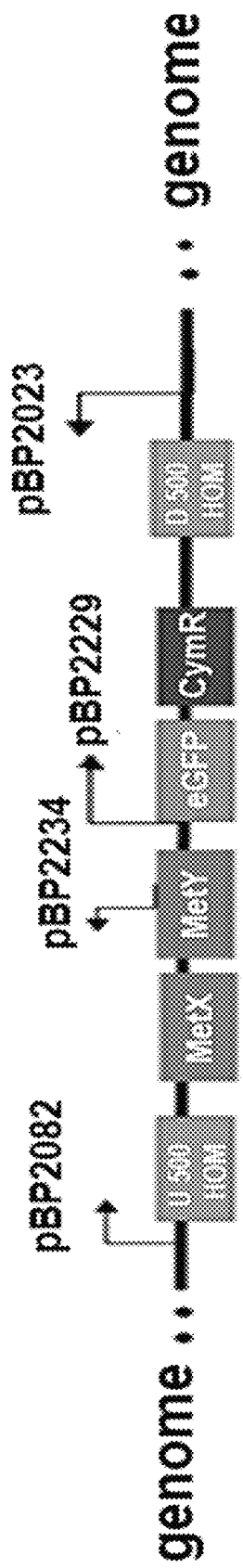

FIG. 16 Primers for analysis of the genomic integration of the expression cassette. To check the integration of metXY in the melAB locus, we used the primer pairs pBP2082/pBP2234 and pBP2229/pBP2023. In each primer pair, one primer annealed outside of the 500 bp homology hooks and the other annealed to the inserted fragment.

Figure 17:
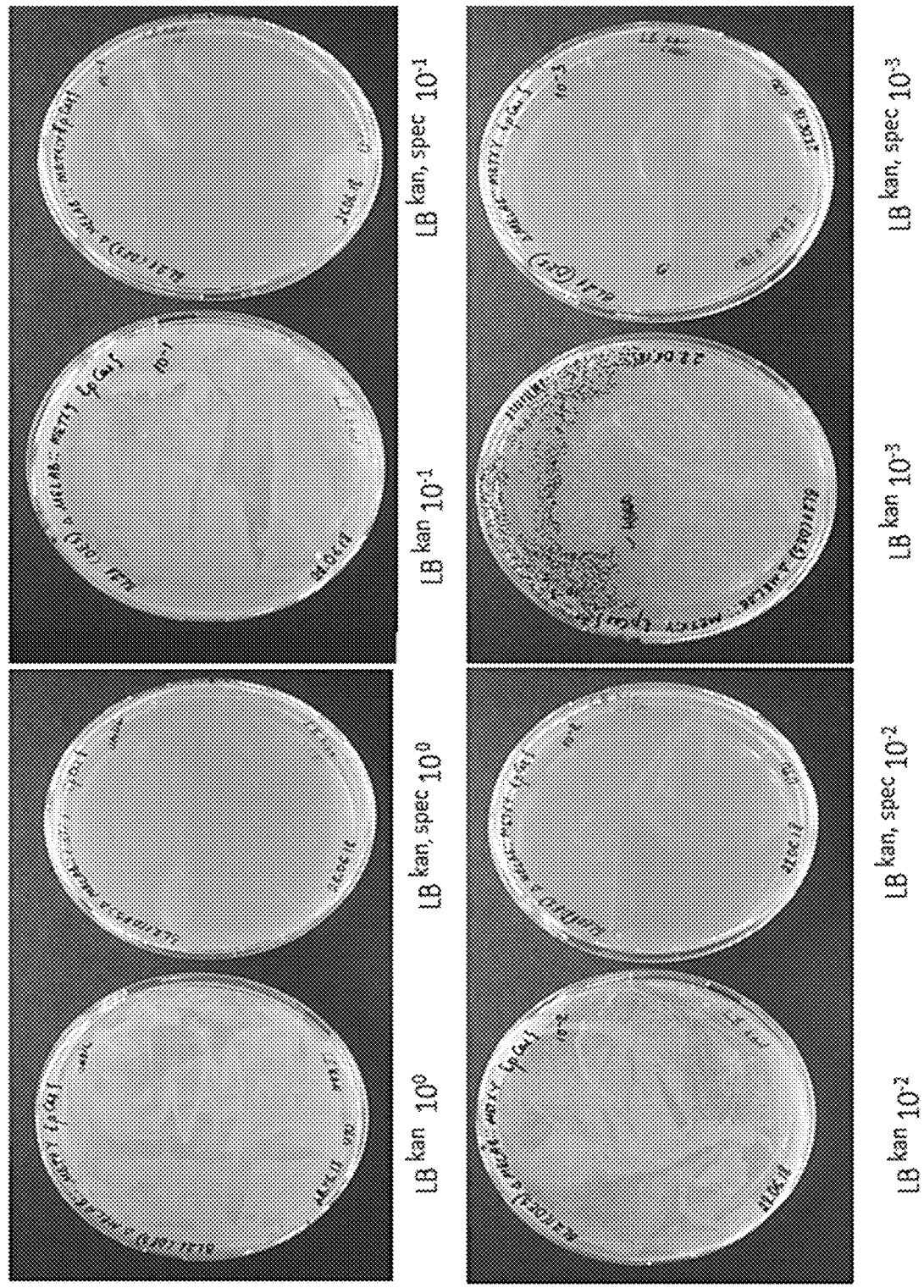

FIG. 17 pTarget cured cells plated on LB plates in presence as well as absence of spectinomycin. From the overnight culture of pTarget cured cells, dilutions of $10^0$ to $10^{-3}$ were plated on LB$^{kan}$ (50 μg/mL of kanamycin) and LB$^{kan, spec}$ (50 μg/mL of each antibiotic) plates. The plates were incubated at 28° C. overnight.

Figure 18:
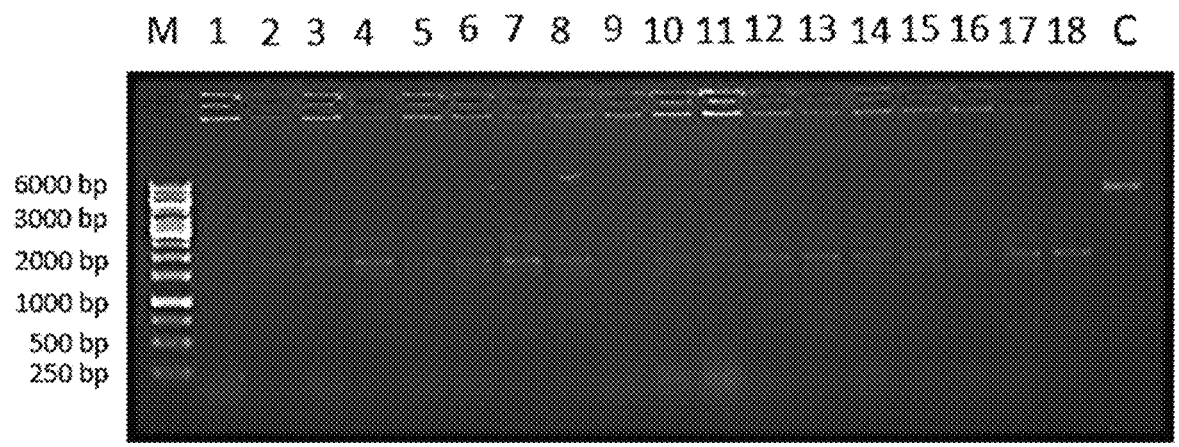
Figure 18:
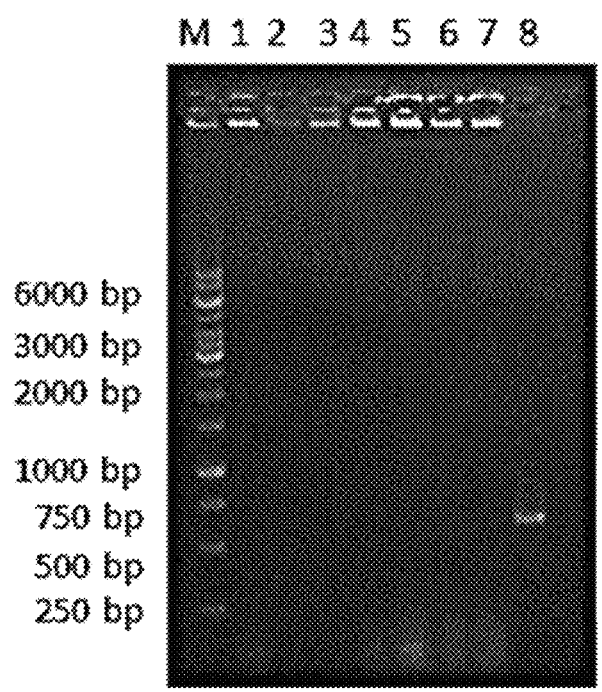

FIG. 18 Colony PCR after pTarget and pCas curing. a. pTarget curing, M, DNA size marker GeneRuler, 1-18 chosen clones, C-control pTarget plasmid, expected band size 3214 bp. b. pCas curing. M, DNA size marker, GeneRuler; 1-7 selected clones, 8, control with pCas sequence, expected band size: 655 bp.

Figure 19:
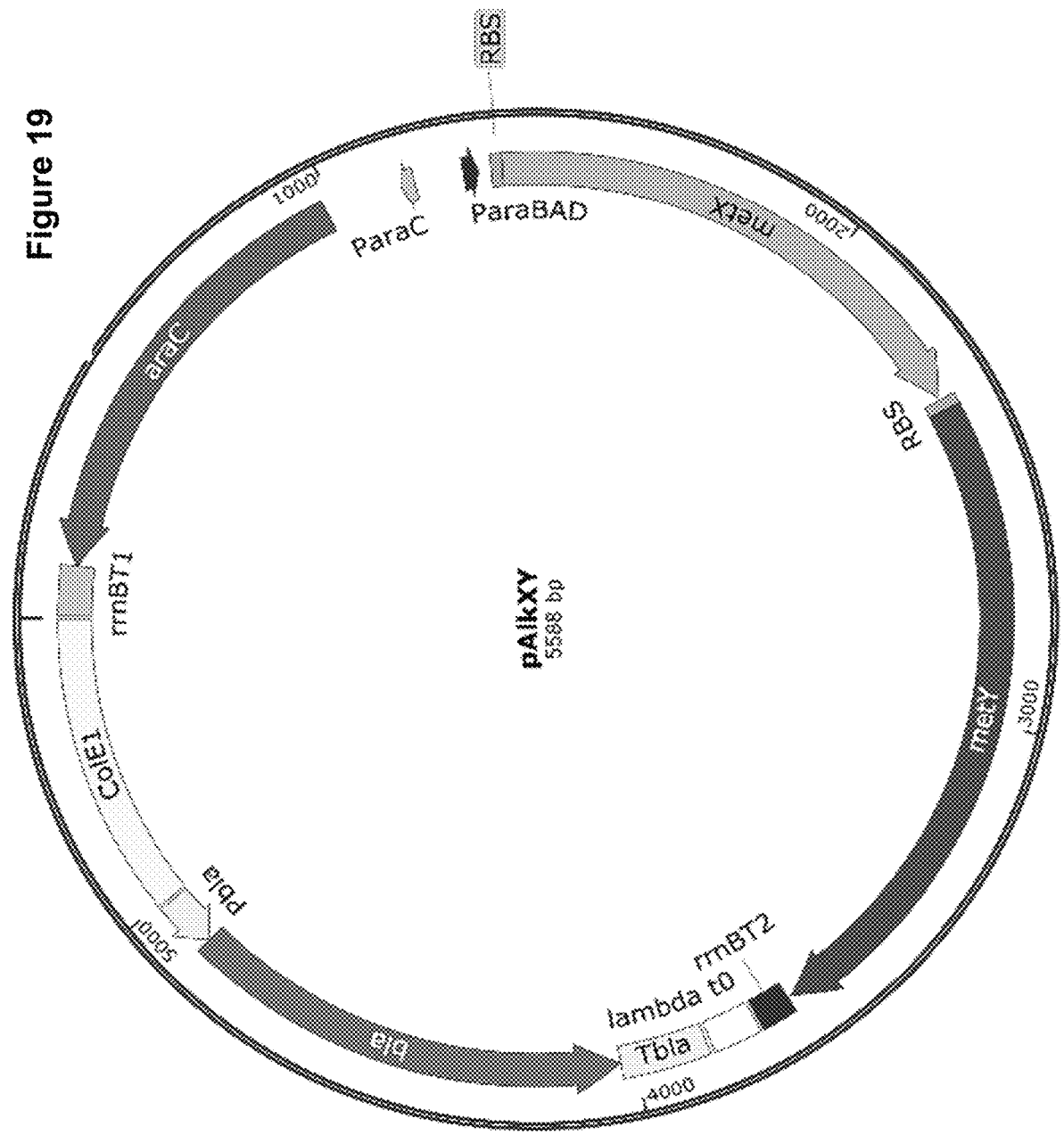
Figure 20A:
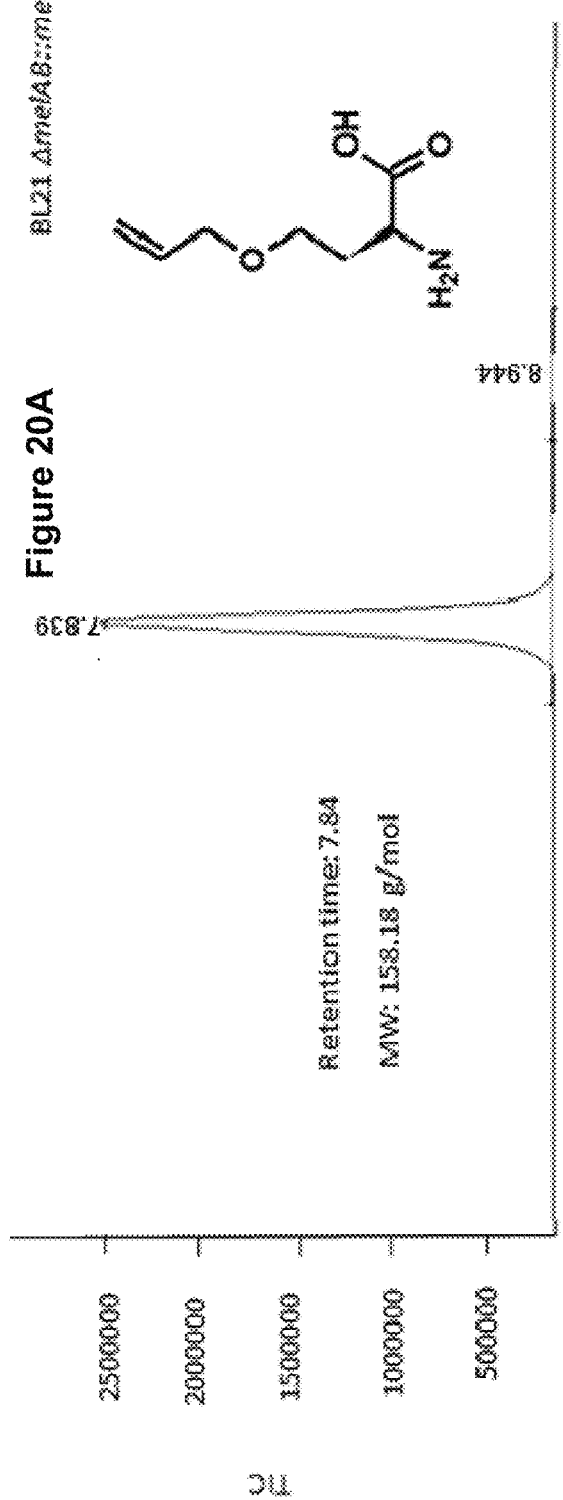
Figure 20A:
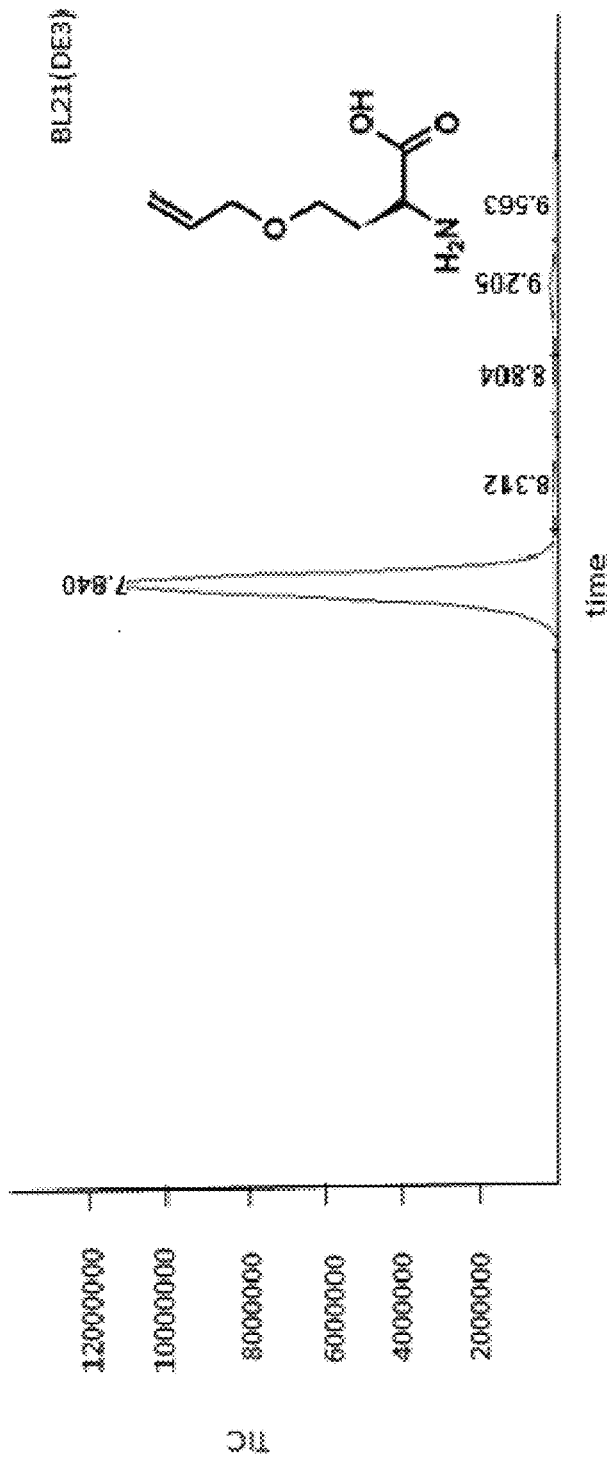
Figure 20B:
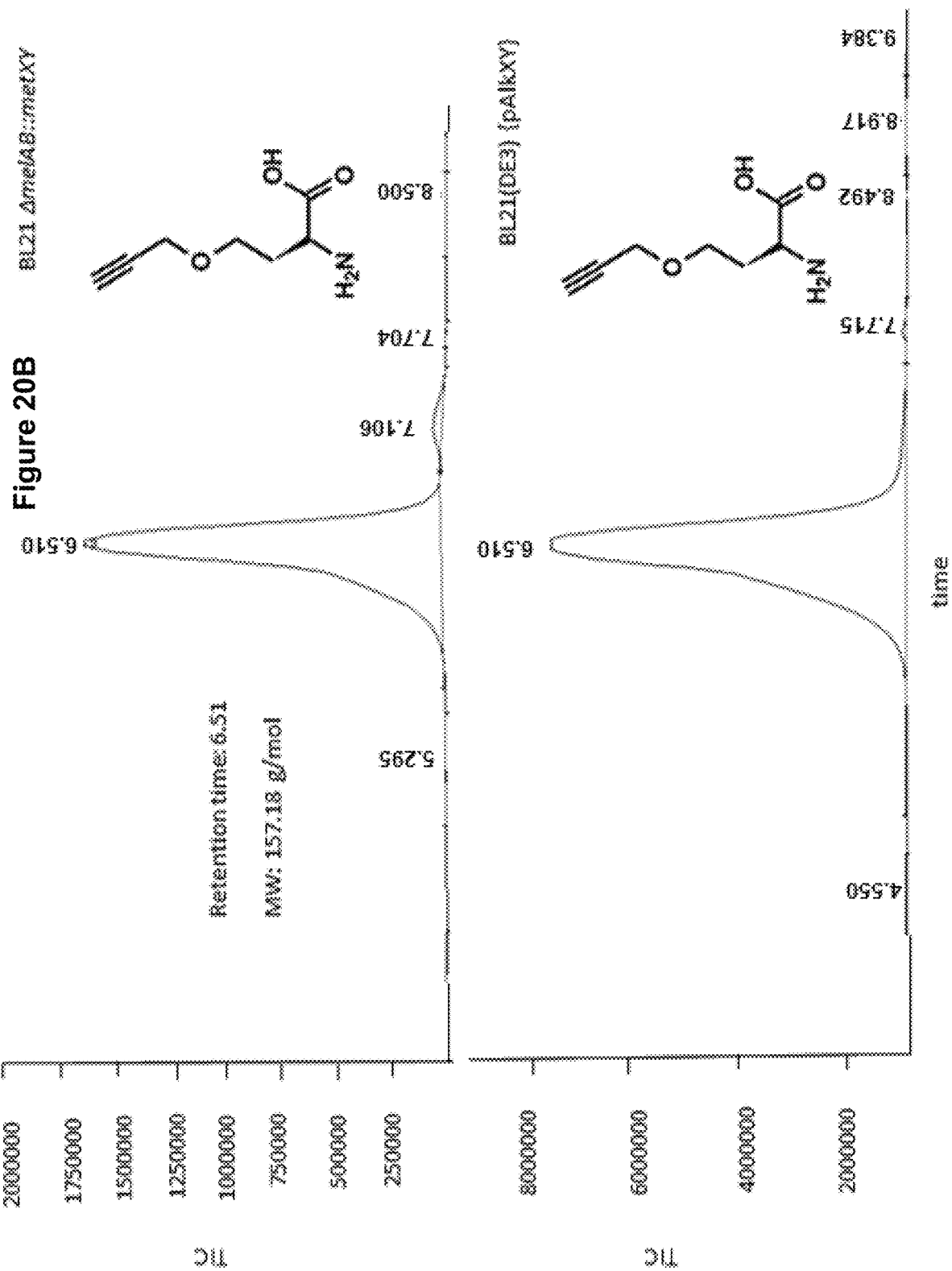
Figure 20C:
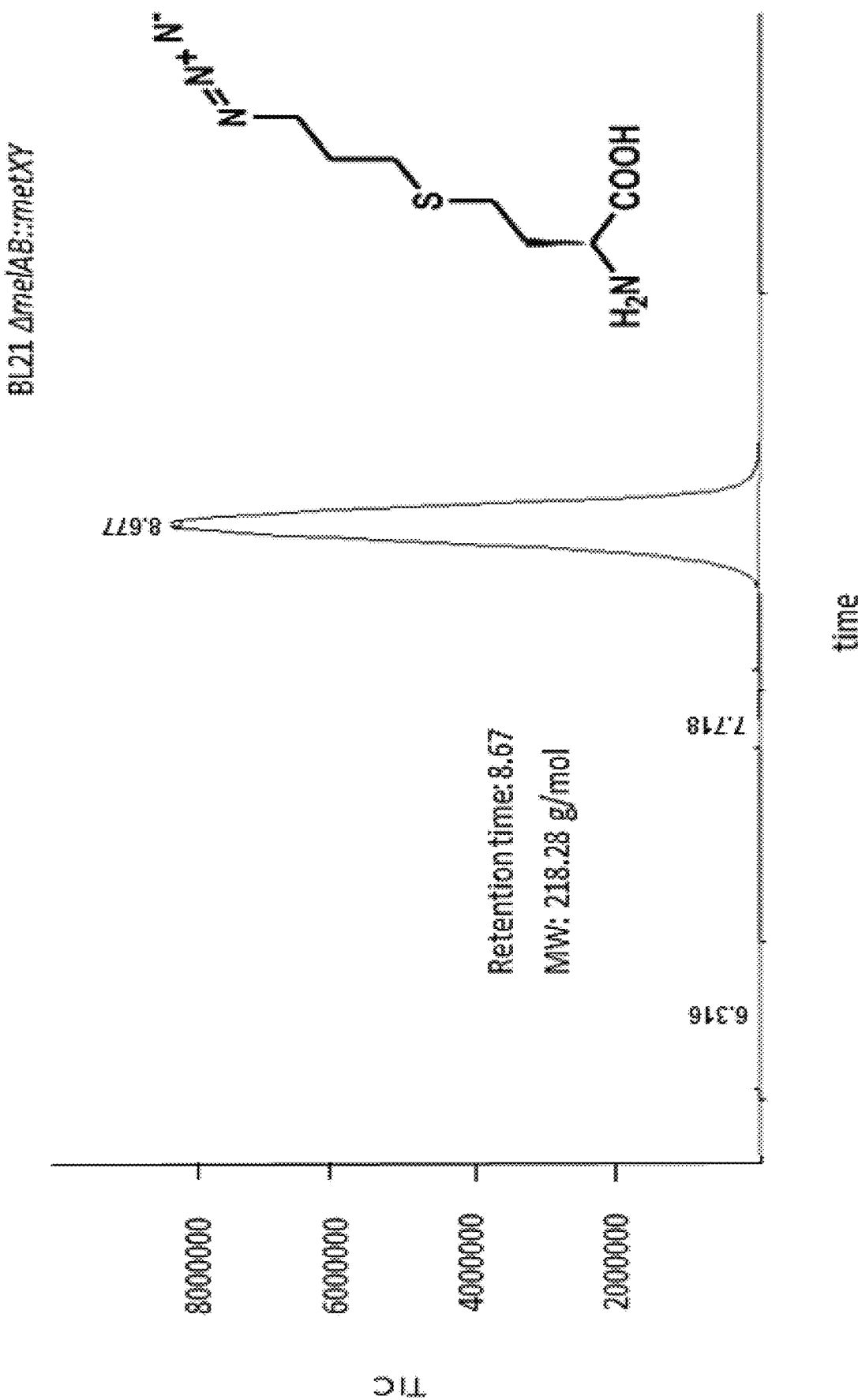
Figure 20D:
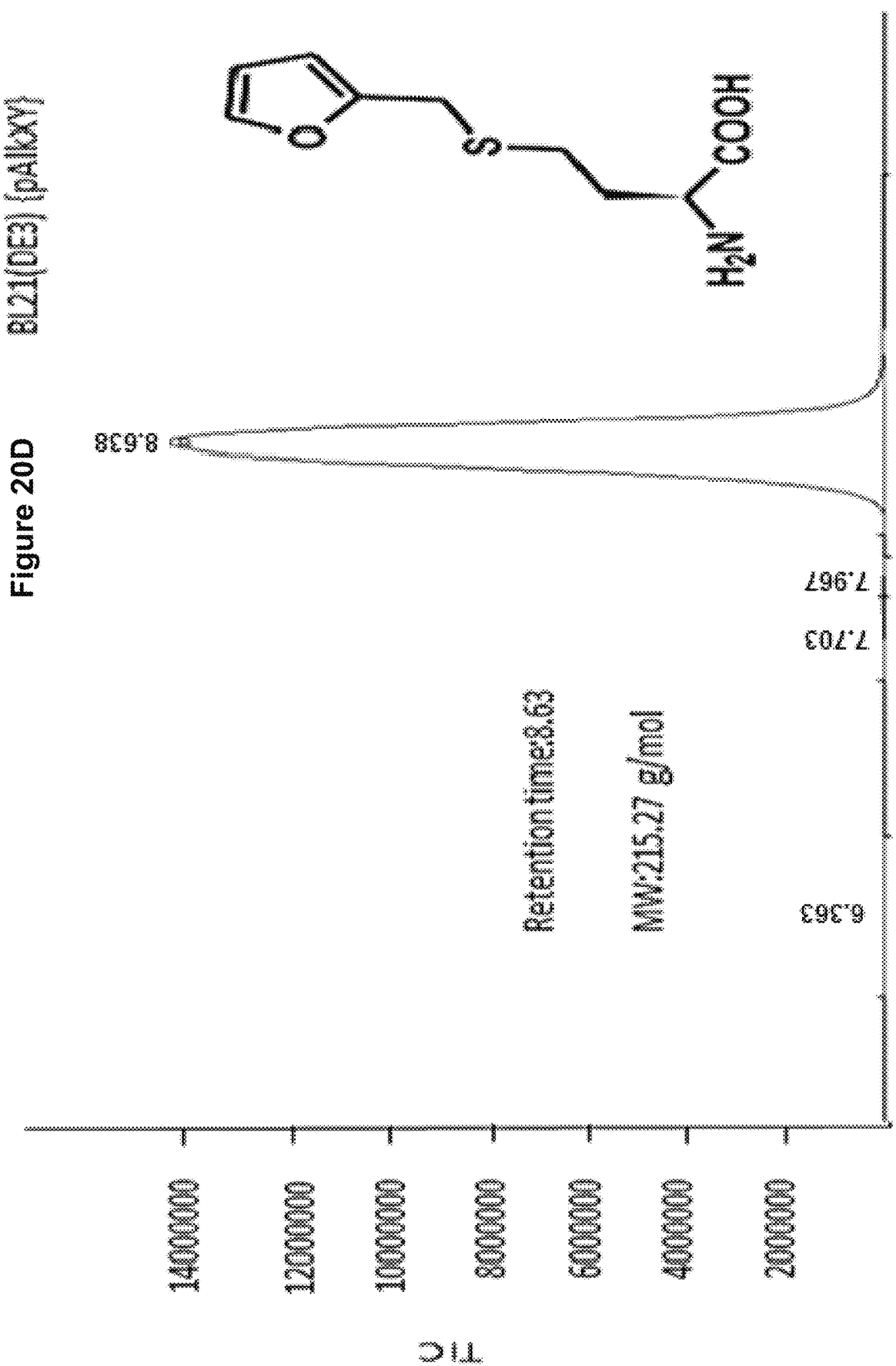

FIG. 19 pAlkXY. metX, gene encoding L-homoserine-O-acetyltransferase (HSAT) from *Deinococcus radiodurans*; metY, gene encoding O-acetyl-homoserine sulfhydrylase (OAHS) from *Bacillus stearothermophilus*; $P_{araBAD}$, arabinose-inducible promoter; bla, ampicillin resistance marker with native promoter ($P_{bla}$) and terminator ($T_{bla}$); araC, arabinose promoter regulator with native promoter ($P_{araC}$); ColE1, origin of replication; RBS, ribosome binding site; rrnBT1, rrnBT2 and lambda t0 are terminators.

FIG. 20 HPLC-MS spectra of the Met analogs biosynthesized by BL21ΔmelAB::metXY and BL21(DE3) {pAlkXY}. A) O-allyl-L-homoserine (Oen); B) O-propargyl-L-homoserine (Oyn); C) S-azidopropyl-L-homocysteine (Saz) and D) S-furfuryl-L-homocysteine (SFur). TIC, total ion count.

The following sequences are described and provided herein:

Protein sequence of OAHS derived from *Geobacillus stearothermophilus*
SEQ ID NO: 1
MSNEQTFRPETLAIHAGQKPDAETGARAVPIYQTSSYVFRDSEHAANLFG

LKEEGFIYTRIMNPTNDVLEKRIAALEGGIGALALSSGQAAVFYSIINIA

SAGDEIVSSSSIYGGTYNLFAHTLRKFGITVKFVDPSDPENFERAITDKT

KALFAETIGNPKNDVLDIEAVADIAHRHAIPLIVDNTVASPYLLRPIEFG

ADIVVHSATKFIGGHGNSIGGVIVDSGKFDWKGSGKFPEFTEPDPSYHGL

VYVDAVGEAAYITKARIQLLRDLGAALSPFNAFLLLQGLETLHLRMQRHS

ENALAVAKFLEEEEAVESVNYPGLPSHPSHELAKKYLPNGQGAIVTFEIK

GGVEAGKKLIDSVKLFSHLANIGDSKSLIIHPASTTHEQLTPEEQLSAGV

TPGLVRLSVGTEAIDDILDDLRQAIRQSQTVGVK

Protein sequence of HSAT derived from *Deinococcus radiodurans* (UniProtKB Q9RVZ8)
SEQ ID NO: 2
MTAVLAGHASALLLTEEPDCSGPQTVVLFRREPLLLDCGRALSDVRVAFH

TYGTPRADATLVLHALTGDSAVHEWWPDFLGAGRPLDPADDYVVCANVLG

GCAGTTSAAELAATCSGPVPLSLRDMARVGRALLDSLGVRRVRVIGASMG

GMLAYAWLLECPDLVEKAVIIGAPARHSPWAIGLNTAARSAIALAPGGEG

LKVARQIAMLSYRSPESLSRTQAGQRVPGVPAVTSYLHYQGEKLAARDEQ

TYCALTWAMDAFQPSSADLKAVRAPVLVVGISSDLLYPAAEVRACAAELP

HADYWELGSIHGHDAFLMDPQDLPERVGAFLRS

Protein sequence of HSAT derived from *Mycobacterium smegmatis* (UniProtKB A0QSZ0)
SEQ ID NO: 3
MTIIEERATDTGMATVPLPAEGEIGLVHIGALTLENGTVLPDVTIAVQRW

GELAPDRGNVVMVLHALTGDSHVTGPAGDGHPTAGWWDGVAGPGAPIDTD

HWCAIATNVLGGCRGSTGPGSLAPDGKPWGSRFPQITIRDQVAADRAALA

ALGITEVAAVVGGSMGGARALEWLVTHPDDVRAGLVLAVGARATADQIGT

QSTQVAAIKADPDWQGGDYHGTGRAPTEGMEIARRFAHLTYRGEEELDDR

FANTPQDDEDPLTGGRYAVQSYLEYQGGKLARREDPGTYVVLSDALSSHD

-continued
VGRGRGGVEAALRSCPVPVVVGGITSDRLYPIRLQQELAELLPGCQGLDV

VDSIYGHDGFLVETELVGKLIRRTLELAQR artificial DNA
Primer pBP1471
SEQ ID NO: 4
ctgagtaggacaaatccgccgtcgacAAATCATAAAAAATTTATTTGCTT

TGTGAGCGG artificial DNA
Primer pBP1472
SEQ ID NO: 5
agaggccccaaggggttatgctagcATTTAAATcTATCAGTGATGGTGAT

GGTGATGGG

DNA
Flavodoxin (Fdx) from Clostridium beijerinckii
(codon harmonized for E. coli)
The gene encodes Fdx carrying an N-terminal
StrepII-tag and C-terminal hexahistidine tag for
affinity purification (bold); GS linker,
italic and underlined.
SEQ ID NO: 6
ATGTGGAGCCACCCGCAGTTCGAAAAAGGATCCATGAAAATCGTATATTG

GTCTGGTACCGGCAACACTGAGAAAATGGCAGAGCTCATCGCTAAAGGTA

TCATCGAATCTGGTAAAGACGTCAACACCATCAACGTGTCTGACGTTAAC

ATCGATGAACTGCTGAACGAAGATATCCTGATCCTGGGTTGCTCTGCCAT

GGGCGATGAAGTTCTCGAGGAAAGCGAATTTGAACCGTTCATCGAAGAGA

TCTCTACCAAAATCTCTGGTAAGAAGGTTGCGCTGTTCGGTTCTTATGGT

TGGGGCGACGGTAAGTGGATGCGTGACTTCGAAGAACGTATGAACGGCTA

TGGTTGCGTTGTTGTTGAGACCCCGCTGATCGTTCAGAACGAGCCGGACG

AAGCTGAGCAGGACTGCATCGAATTTGGTAAGAAGATCGCGAACATC*GGA*

*TCC*CATCACCATCACCATCACTGATAG

The invention is further illustrated by the following examples, however, without being limited to the example or by any specific embodiment of the examples.

EXAMPLES

Example 1: Material and Methods 1.1 Chemicals and Methods

All standard chemicals used herein were purchased from Sigma (St. Louis, MO), Merck KGaA (Darmstadt, Germany) or Carl Roth GmbH (Karlsruhe, Germany), if not stated differently. Sulfo-Cyanine3-alkyne (CLK-TA117) was purchased from Jena Bioscience (Jena, Germany) and azido-HiLyteF488 from AnaSpec (Fremont, CA). Aqueous stock solutions were sterilized by filtration through 0.20 μm CA syringe filters (Lab Logistic Group GmbH, Meckenheim, Germany). Enzymes for cloning and PCR were from Thermo Fisher Scientific (Waltham, MA). PCRs were performed using Phusion® High-Fidelity DNA polymerase (Thermo Fisher Scientific). S-allyl thioester, S-propargyl thioester and all of the ncAA standards were chemically synthesized as part of the PhD thesis of Kathrin Heckenbichler.

1.2 Plasmid and Strains

The Met auxotrophic E. coli B834(DE3) (E. coli B F⁻ ompT hsdSB (rB⁻ mB⁻) dcm⁺ gal met λ(DE3); Merck KGaA, Darmstadt, Germany) was used for the biosynthesis of the Met analogs, as well as for the in-situ biosynthesis and SPI experiments. E. coli Top10F' (E. coli K-12 F'[lacI$^q$ Tn10(Tet$^r$)] mcrA Δ(mrr-hsdRMS-mcrBC) φ80lacZΔM15 ΔlacX74 deoR nupG recA1 Δ(araABC-leu)7697 galU galK rpsL(Str$^r$) endA1 λ⁻; Thermo Fisher Scientific) was used for cloning experiments and plasmid propagation. pCAS5-X12 and pCAS5-X21 were constructed as part of the master thesis of Lisa Offner (Offner, (2015) Synthetic Biology— Looking at it from a chemist's and an engineer's point of view, University of Technology Graz). pCAS5-12-Fdx was constructed by modification of pCAS5-X12. The Fdx gene carrying an N-terminal StrepII-tag and a C-terminal hexahistidine together with the $P_{T5\text{-}lacO}$ promoter was amplified from a pQE80L vector by PCR (in-house plasmid collection) using primers pBP1471 (ctgagtaggacaaatccgccgtcgacAAATCATAAAAAATTTATTTGCTTTGTGAGCGG) (SEQ ID NO: 4) and pBP1472 (agaggccccc-aggggttatgctagc ATTTAAATcTATCAGTGATGGTGATGGTGATGGG) (SEQ ID NO: 5). The PCR product carried 20-25 bp overlaps for the vector backbone and was introduced at the SalI/PstI site of pCAS2-X12 by Gibson isothermal assembly (Gibson et al., Nat Methods (2009), 6(5): 343-345). In a next step gene X was excised by XbaI and SacI, the remaining vector was purified, blunted and religated following the instructions of the manufacturer (Thermo Scientific). pCAS5-1-Fdx was constructed the same way by excision of the OHAS using NdeI and PacI. All constructs were sequence verified (Microsynth, Vienna, Austria).

1.3 Cultivation Conditions for ncAA Biosynthesis (Shake Flask)

E. coli B834(DE3) cells were used carrying pCAS5-12-Fdx or pCAS5-1-Fdx for the biosynthesis for the Met analogs in shake flasks. 50 mL of M9-Pan medium containing M9 salt buffer (48 mM Na$_2$HPO$_4$, 22 mM KH$_2$PO$_4$, 9 mM NaCl and 19 mM NH$_4$Cl) was supplemented with 1 mM MgSO$_4$, 7 μM CaCl$_2$ and trace elements (9 μM FeSO$_4$, 3.5 μM MnSO$_4$, 2.5 μM AlCl$_3$, 2 μM CoCl$_2$, 0.4 μM ZnSO$_4$, 0.5 μM Na$_2$MoO$_4$, 0.4 μM CuCl$_2$ and 0.5 μM H$_3$BO$_4$). 20 mM glucose was provided as the carbon source. The medium was additionally supplemented with 0.01% (w/v) D-pantothenate and 100 mg/L ampicillin for plasmid propagation. 3 g/L of yeast extract were added for Met depletion at a $D_{600}$ of 3 (Anderhuber et al., J Biotechnol (2016), 235: 100-111). Main cultures were inoculated to an initial $D_{600}$ of 0.1 and cultivated at 37° C. and vigorous shaking. At a $D_{600}$ of 1, cascade enzyme expression was induced by the addition of 0.2% (w/v) of arabinose. All cultures were supplemented with 10 mM L-homoserine and 5 mM of the nucleophile substrate (Table 3). In case of the norbornene bearing substrates (Tables 4), we tested 1 mM and 5 mM. To analyze the in situ production of the Met analogs, we isolated clarified culture supernatants by centrifugation (13,000 g, 4° C., 10 minutes) and subsequent filtration through 0.20 μm CA syringe filters (PES, 0.2 μM, Agilent technologies Inc.). Clarified culture supernatants were directly used for HPLC-MS analysis.

1.4 NcAA Biosynthesis and Incorporation (1 L Benchtop Bioreactor)

The medium used fort the bioreactor cultivations is shown in Table 2. Cells were cultured in stirred tank bioreactors (DASGIP, Jülich, Germany). For process control, the reactor was equipped with a pH (Broadly James Corp, Bedford, Great Britain), as well as a $pO_2$ electrode (Broadly James Corp). The fermentation was performed at pH 7.0 by automated addition of 12.5% (v/v) $NH_3$ or 10% (v/v) $H_3PO_4$. Dissolved oxygen was maintained above 20% relative saturation by adjusting the stirrer speed from 500 to 2000 rpm. Oxygen was provided at maximum air flow rate by bubbling air into the culture with an aeration module (Vögtlin, Basel, Switzerland). Cells were incubated at 37 C. The initial $D_{600}$ was 0.1. At a $D_{600}$ of ~3 cultures were supplemented with 10 mM L-homoserine and 10 mM of the nucleophile substrate (Table 2). In case of $NaN_3$, we supplemented 0.5 mM at a $D_{600}$ of 3 and added the remaining 9.5 mM by constant feeding over 20 hours due to the cell toxic effects of $NaN_3$. HSAT and OHAS expression was induced by the addition of 20 mM of arabinose. At Met depletion ($D_{600}$ of ~12), Fdx expression (~9 h) was induced by the addition of 0.5 mM of IPTG. Cells were harvested by centrifugation after 24 hours (5000 g, 4° C., 30 minutes). Culture supernatants were clarified by centrifugation (13,000 g, 4° C., 10 minutes) and subsequent filtration through 0.20 µm CA syringe filters (PES, 0.2 µM, Agilent technologies Inc.) before Fdx induction and at the end of the fermentation. Clarified culture supernatants were directly used for HPLC-MS analysis.

TABLE 2

Bioreactor medium

| ingredient | $c_{stock}$ | $c_{final}$ | $V_{stock}$ [mL]/400 mL |
|---|---|---|---|
| M9 salt stock[2] | 5 X | 1 X | 80 |
| $MgSO_4$ | 1M | 2 mM | 0.8 |
| $Ca^{2+}$/citrate[2] | 1 mg/mL/ 100 mg/ml | 2 µg/mL/ 200 mg/mL | 0.8 |
| D-pantothenate | 10% | 0.02% | 0.8 |
| glucose[2] | 1M | 90 mM | 36 |
| TE[2] | 18.7 X | 1 X | 0.050 |
| yeast extract[1,4] | — | 12 g/L | 4.8 g |
| antifoam[2,3] | 1 + 9 | — | 0.4 |
| ampicilin[2] | 100 mg/mL | 100 mg/L | 0.4 |
| $ddH_2O$[1] | — | — | 280 |

[1]4.8 g YE were dissolved in $ddH_2O$ and autoclaved directly in the fermenter.
[2]All other ingredients were supplemented afterwards as sterile stock solutions via a septum.
[3]Antifoam was added under stirring.
[4]Yeast extract lead to Met depletion at $D_{600}$ of 12.

1.5 Analytics

Cell growth was monitored by reading the attenuance at 600 nm ($D_{600}$) using an Eppendorf BioPhotometer® (Eppendorf, Wesseling-Berzdorf, Germany). SDS-PAGE using 4-12% Bis-Tris SDS-gels (Thermo Fisher Scientific) was performed following the instructions of the manufacturer.

1.6 Protein Purification

The cells were mechanically lysed on a Homogenizer Emulsiflex C3 (Avestin, Ottawa, Canada). Cell lysates were clarified by centrifugation at 40,000 g at 4° C. for 60 minutes. The his-tagged proteins were further purified via gravity flow $Ni^{2+}$-chelate affinity chromatography using Ni-NTA agarose following the instructions of the manufacturer (Qiagen, Hilden, Germany).

1.7 HPLC-MS Analysis

For HPLC-MS (Agilent technologies Inc.), analysis of the biosynthesized ncAAs, 5 µL of the clarified culture supernatant were separated on a Litochrat 250 PurospherStar RP18e 5 µM column (Merck Millipore). Met analogs were separated from other metabolites in the culture supernatant by eluting with a gradient from 2 to 98% acetonitrile in 0.1% (v/v) formic acid in water within 12 minutes. A mixture of $ddH_2O$ with 0.1% formic acid and acetonitrile was used as the mobile phase at a flow rate of 0.7 mL/min and the column temperature was set to 30° C. The amino acids in the supernatant were identified by their retention times in comparison to calibration standards (chemically synthesized) with defined concentrations of 0.1 mM, 0.2 mM, 0.5 mM, 1.0 mM, 2.0 mM and 5.0 mM in bioreactor medium matrix (without glucose, yeast extract, D-pantothenate, antifoam and antibiotic). Calibration curves were calculated by linear curve fit using EXCEL (Microsoft, Redmond, WA). Data analysis was performed using the Agilent Chem Station Software (Agilent technologies Inc.).

1.8 Bioorthogonal Conjugation

34 µL of purified Fdx samples in a final volume of 40 µL 40 mM Tris-Cl buffer (pH 6.8) were incubated with 2.5 mM copper sulfate, 5 mM sodium ascorbate and 20 µM of Sulfo-Cyanine3-alkyne or azido-HiLyteF$_{488}$. The reaction mixture was incubated over night at 4° C. Samples were heated to 98° C. for 10 minutes prior SDS-PAGE analysis. Samples were separated on a 4-12% Bis-Tris gel following the instructions of the manufacturer (Thermo Fisher Scientific). The gels were analyzed using a broad range UV screen to detect dye fluorescence and subsequently stained with Coomassie Blue following standard procedures.

Example 2: Results and Discussion 2.1 Biosynthesis of S-Allyl-L-Homocysteine (Sen)

By genetic engineering, a protocol for the in vivo synthesis of S-allyl-L-homocysteine (FIG. 1, 4a; Sen) was developed, starting from L-homoserine (FIG. 1) in a modular two-enzyme cascade. The first step of the two-enzyme cascade is the acetylation of L-homoserine catalyzed by the acetyl-CoA dependent enzyme L-homoserine-O-acetyltransferase from *Deinococcus radiodurans* (HSAT; SEQ ID NO: 2). The second step of the cascade is the conversion of O-acetyl-L-homoserine (FIG. 1, 2) to the methionine analog (FIG. 1, 4) catalyzed by the O-acetyl-L-homoserine sulfhydrylase from *Geobacillus stearothermophilus* CN3 (OAHS; SEQ ID NO: 1). Depending on which nucleophile 3 (d. FIG. 1) is supplemented, different Met analogs can be produced. Allylthiol (allyl mercaptan; FIG. 1,3a) was used as the substrate to biosynthesize S-allyl-homocysteine, Sen (FIG. 1, 4a).

The vectors used for the expression of the cascade genes were derived from the customized pCAS plasmid (Gourinchas et al., Chem Commun (Camb) (2015), 51(14): 2828-2831) because this backbone carries two independently inducible promoters. HSAT and OAHS genes were put under the control of an arabinose-inducible araBAD promoter. The expression of the target protein was controlled by an IPTG-inducible T5-lacO promoter. This strategy facilitates the in vivo production of the ncAA as well as its simultaneous incorporation into a target protein.

For the initial biosynthesis trials, the plasmid carried an additional gene (X) which was in-frame with the HSAT (1) and OHAS (2). This gene was not required for the synthesis of Sen, but also controlled by the arabinose inducible promoter. This plasmid (pCAS2-X12; Plasmid 1; cd. FIG. 8) was generated in a different project and carried a random DNA sequence instead of the target protein (Offner, (2015) Synthetic Biology—Looking at it from a chemist's and an engineer's point of view, University of Technology Graz). The Met auxotrophic E. coli strain B834(DE3) was used to monitor the Sen biosynthesis. The strain was transformed with the pCAS2-X12 plasmid and cultivated in 50 mL M9 medium. 0.01% (w/v) of D-pantothenate was added to the medium (M9-Pan). Furthermore, 3 g/L of YE were used to provide a limiting amount of Met that would result in a Met depended growth stop at a $D_{600}$ of 3, as described in Anderhuber et al. (2016, loc. cit.). HSAT and OHAS expression was induced at a $D_{600}$ of 0.8-1.0 (⅓-¼ of $D_{600, final}$) to obtain functional expression of both cascade enzymes for sufficient biosynthesis of Sen before Met depletion.

Figure 2:
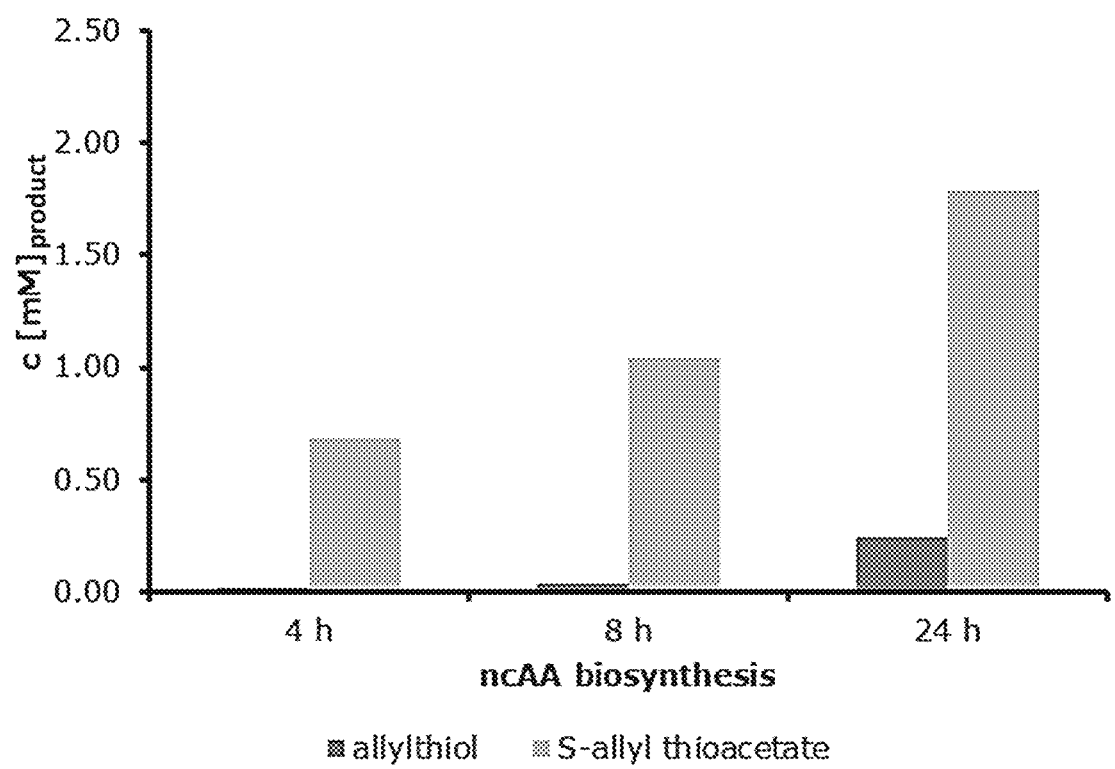

Cells expressing HSAT and OHAS produced only a traceable amount of Sen after 24 hours (roughly 0.4 mM) when L-homoserine and allylthiol were supplemented to the medium (FIG. 2, dark gray bars). The experiment was repeated and the cultures were supplemented with S-allyl thioacetate instead of allylthiol. The supply of the thiol in a "pre-drug" form resulted in a four-fold increased amount of biosynthesized Sen (FIG. 2, light grey bars).

As a next step, it was tested whether the order of the cascade genes had an influence on the Sen biosynthesis activity since HSAT and OHAS are expressed from the same promoter in a polycistronic manner. To do so, plasmids carrying an additional gene X (X) at the first position (as already discussed above) were used and the order of HSAT (1) and OHAS (2) was altered. The Sen biosynthesis capacity of cells harboring pCAS2-X12 (Plasmid 1; FIG. 8) or pCAS2-X21 (Plasmid 2; FIG. 9) was again tested in M9-Pan medium supplemented with L-homoserine and S-allyl thioacetate. The gene order of the cascade genes had an influence on the Sen biosynthesis capacity. After 24 hours, cells carrying pCAS-X12 (FIG. 3, light grey bars) synthesized about double the amount of Sen compared to cells harboring pCAS-X21 (FIG. 3, dark grey bars).

2.2 Substrate Promiscuity of OAHS Allows the Biosynthesis of a Whole Set of Met Analogs with Diverse Reactive Side Chain Chemistries pCAS2-X12 (Plasmid 1, FIG. 8) plasmid carrying the cascade genes HSAT and OHAS was modified to be suitable for coupling the in situ synthesis of Met analogs and direct incorporation into a target protein by SPI. For that, the flavodoxin (Fdx) from Clostridium beijerinckii (SEQ ID NO: 6) was introduced into pCAS2 at the SalI and PstI restriction sites. This led to the loss of the $P_{T7}$ promoter. To decouple the expression of the target gene from the expression of HSAT and OHAS, the Fdx was set under the control of an IPTG inducible $P_{T5-lacO}$ promoter (derived from pQE80L). For further protein purification the Fdx carried an N-terminal StrepII- and a C-terminal hexahistidine tag. Additionally, gene X (for details cf. Example 1, Materials and Methods) was excised from the plasmid. The resulting cascade plasmid pCAS5-12-Fdx is shown in Plasmid 3 (FIG. 10).

The functional pathway for the biosynthesis of the methionine analog S-allyl-L-homocysteine from L-homoserine and S-allyl thioacetate was again demonstrated (FIG. 4A and Table 1A). B834(DE3) cells harboring pCAS5-12-Fdx were cultivated in M9-Pan. At a $D_{600}$ of 0.8-1 (~after 1-2 h), 10 mM L-homoserine and 5 mM of S-allyl thioacetate were supplemented and HSAT and OHAS expression was induced by the addition of 0.2% arabinose. After 24 hours, the culture supernatants were analyzed by HPLC-MS and successful biosynthesis of Sen was confirmed (data not shown). No signal was received if cells carrying plasmid pCAS5-1-Fdx (Plasmid 4, FIG. 11) lacking the OHAS gene were treated the same way. This shows that the second step of the reaction is catalyzed by the OHAS and not by an unspecific endogenous host reactivity. Cells carrying pCAS5-Fdx lacking both cascade enzymes were tested and no unspecific formation of the Met analog was observed. The retention time as well as MS signal of the biosynthesized Met analog was confirmed by a Sen standard.

Figure 5B:
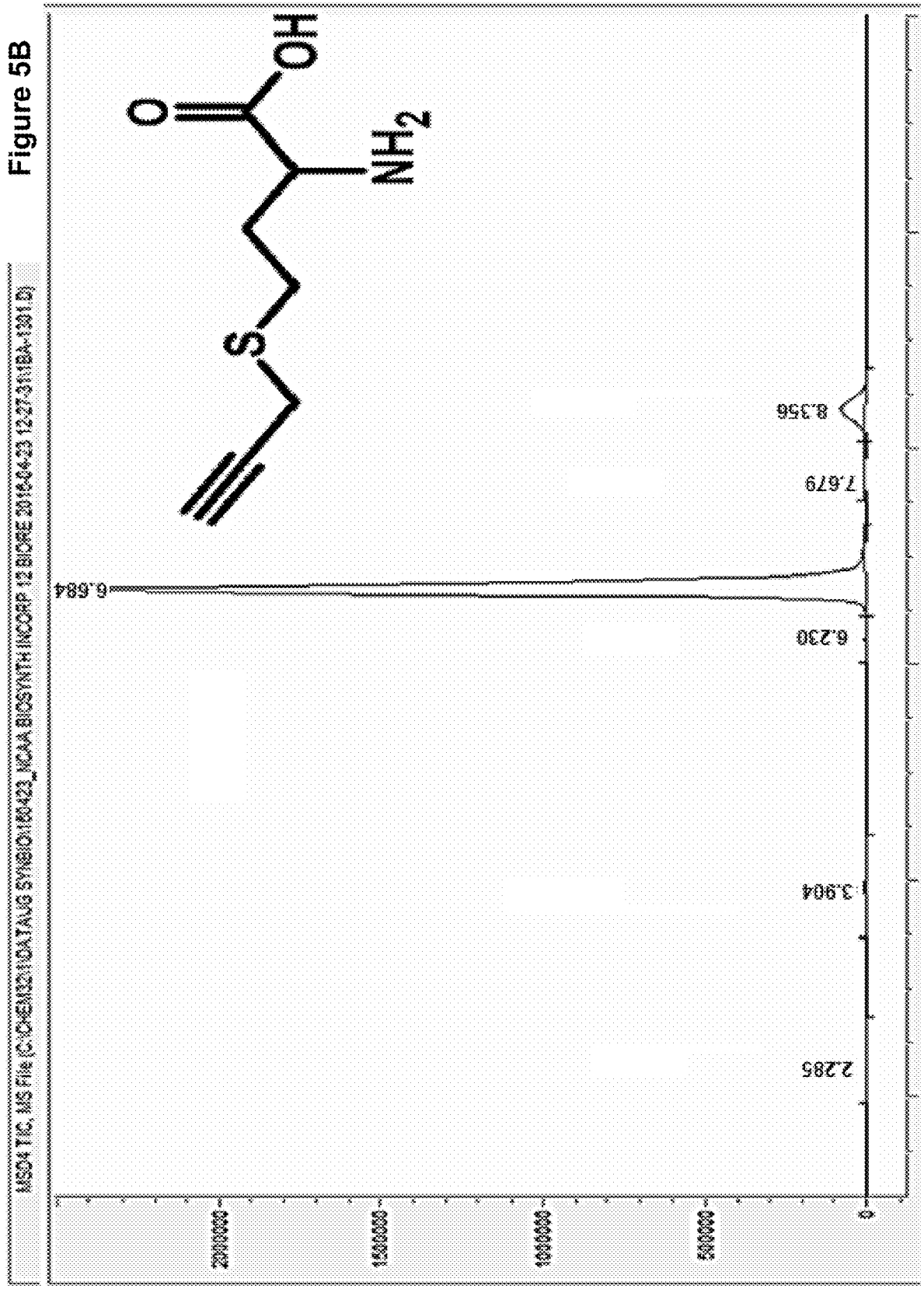
Figure 5C:
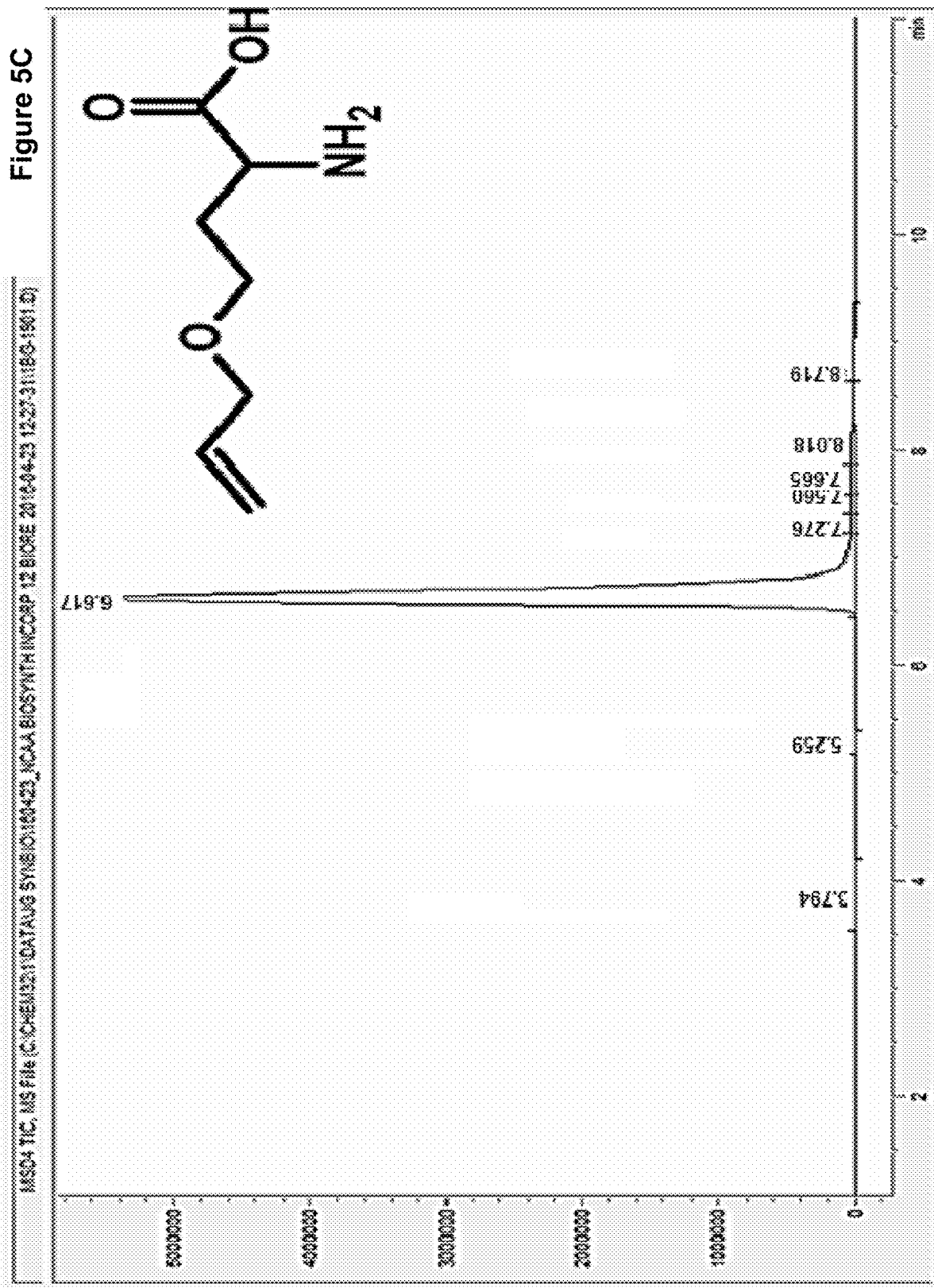
Figure 5D:
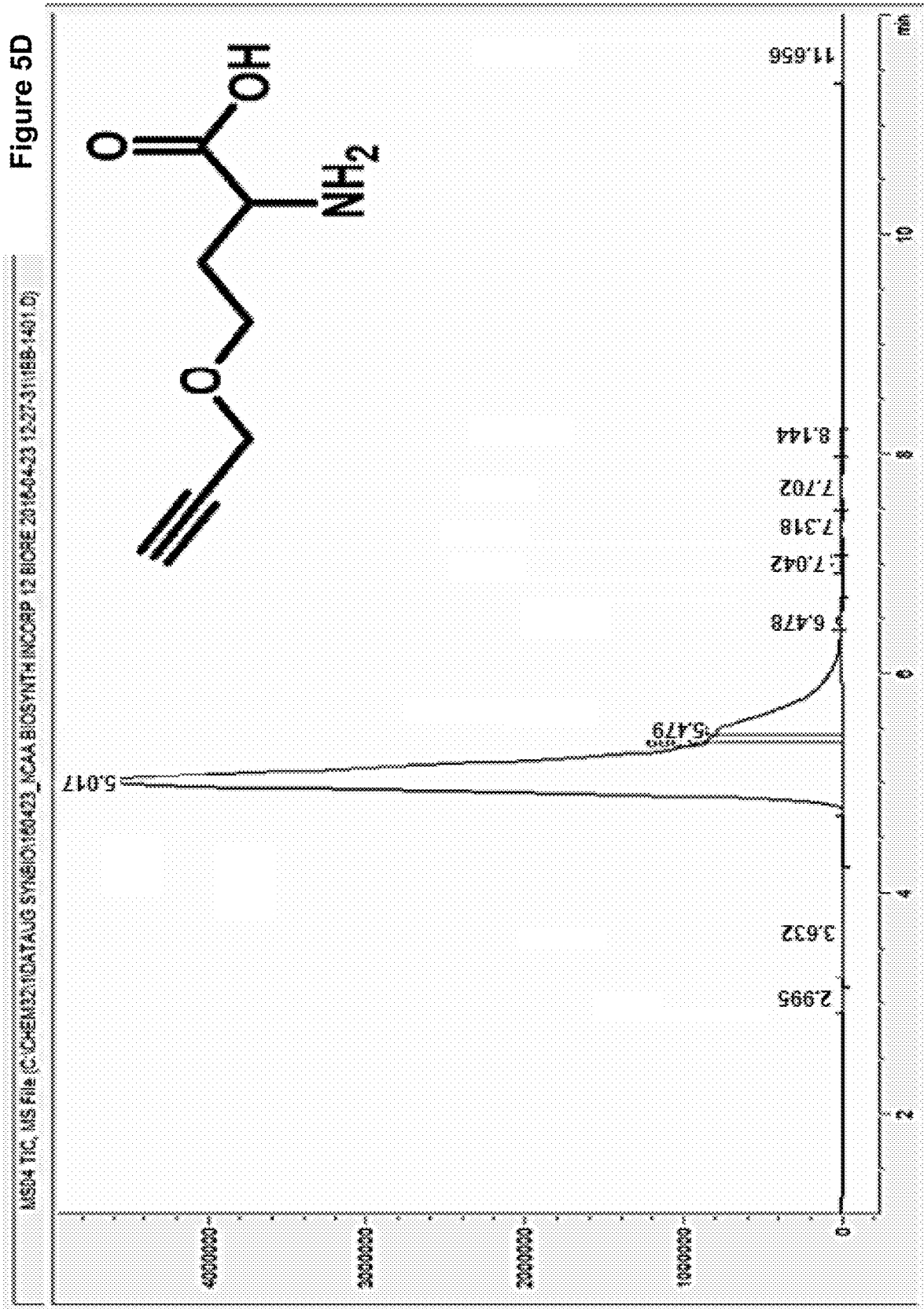
Figure 5E:
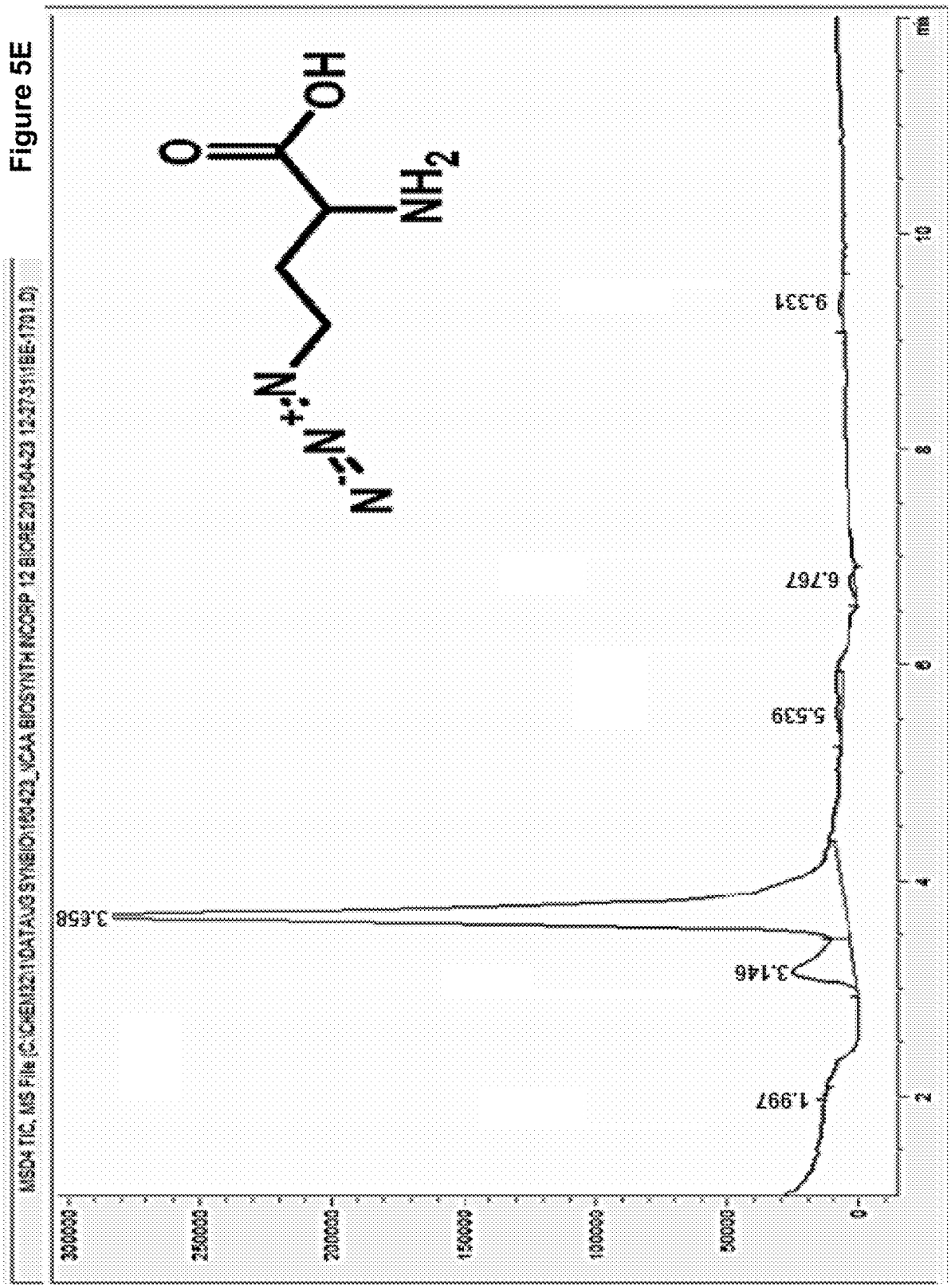
Figure 5F:
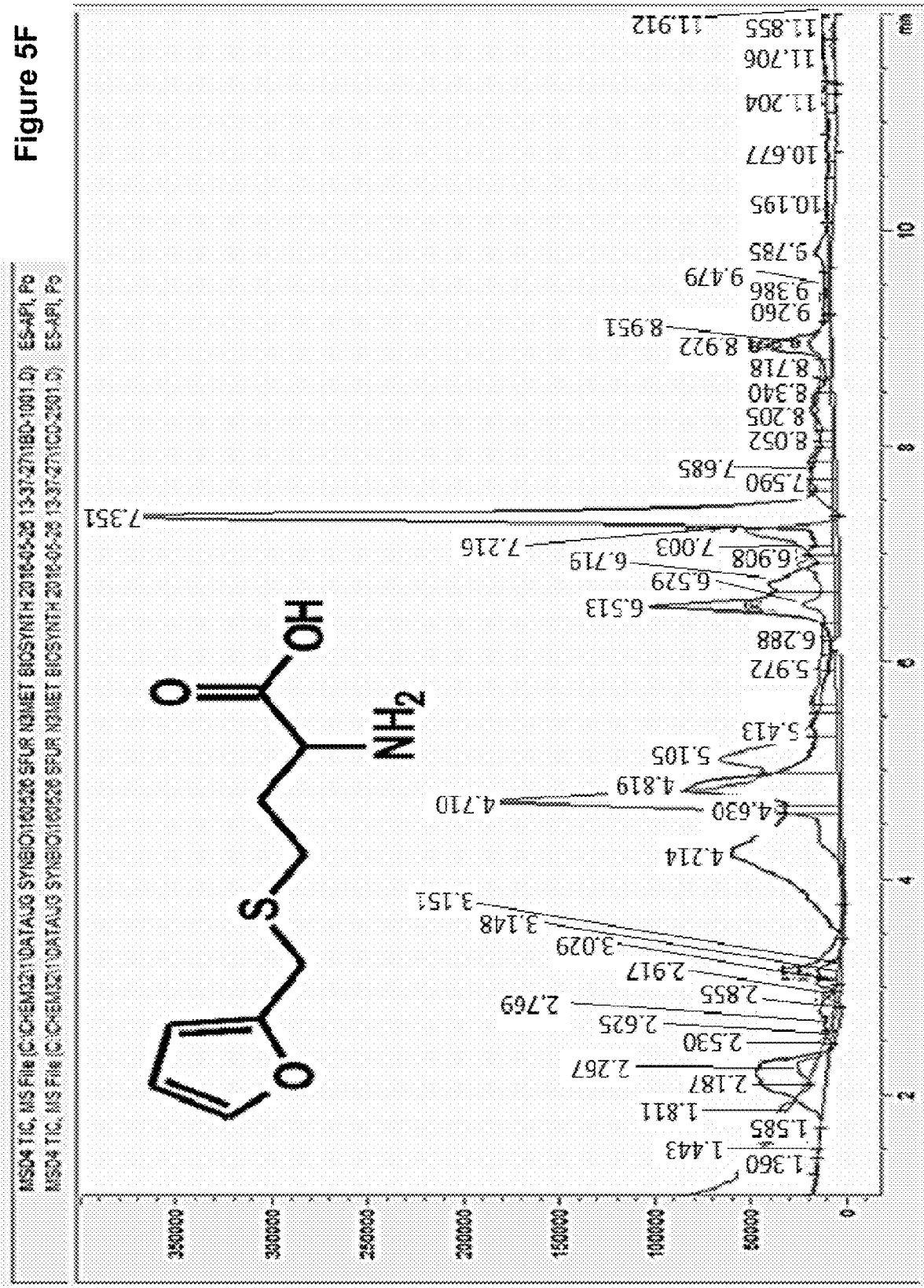
Figure 5G:
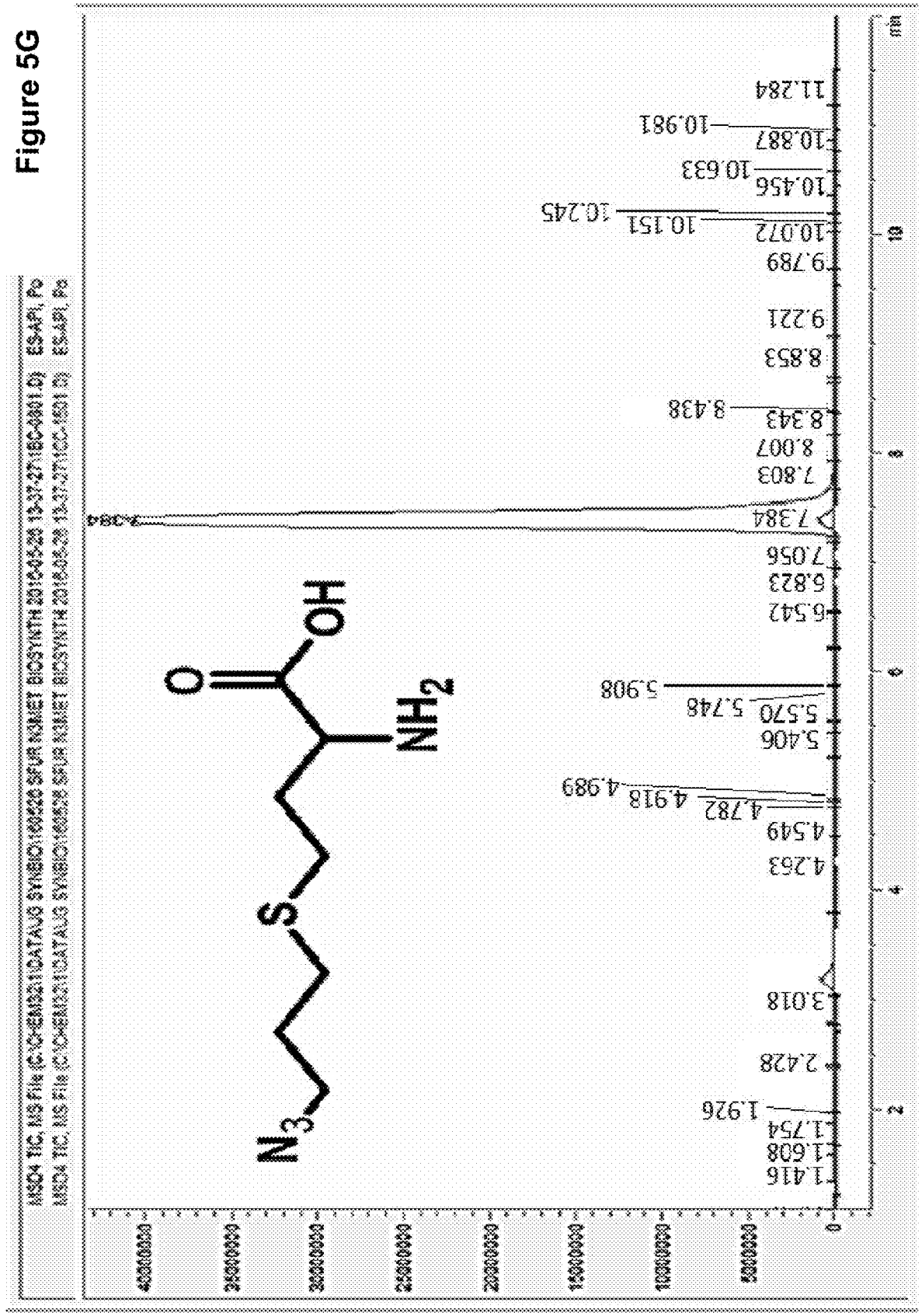

By exchanging the S-allyl thioester (FIG. 4A and Table 1A) for S-propargyl thioester (FIG. 4B and Table 1B); S-furfuryl thioester (FIG. 4G and Table 1G); S-azidopropyl thioester (FIG. 4F and Table 1F); allyl alcohol (FIG. 4C and Table 1C); propargyl alcohol (FIG. 4D and Table 1D); and sodium azide (FIG. 4E and Table 1E), S-propargyl-L-homocysteine (Syn; Figure SB); S-furfuryl-L-homocysteine (SFur; FIG. 5G); S-azidopropyl-L-homocysteine ($SN_3$; FIG. 5F); O-allyl-L-homoserine (Oen, FIG. 5B); O-propargyl-L-homoserine (Oyn; FIG. 5D); and L-azidohomoalanine (Aha, FIG. 5E) were generated. In a next step, the biosynthesis pathway was tested with other nucleophiles as well, such as different thioacetates, alcohols and azides. Analysis of culture supernatants by HPLC-MS after 24 hours confirmed the successful biosynthesis of all Met analogs. The retention time as well as MS signal was confirmed by chemically synthesized standards. Except Aha, all Met analogs were detectable in the low mM range (~0.5 mM) after Met depletion (4-5 hours of synthesis). In a standard residue-specific incorporation experiment 0.5-1.0 mM of the ncAA are usually supplemented (Anderhuber (2016), loc. cit.). Therefore, the amounts produced by the biosynthesis cascade were in the range necessary for the incorporation of the Met analog into the target protein.

2.3 In-Situ Production of Reactive Met Analogs and Direct Incorporation into the Target Protein Fdx in a Bioreactor The biosynthesis of Met analogs was coupled with their direct incorporation into the target protein Fdx. For the upscaling of the ncAA biosynthesis, a similar strategy as described in Anderhuber (2016, loc.cit.) was applied. To biosynthesize and incorporate the 7 Met analogs simultaneously, Met auxotrophic E. coli B834(DE3) cells were supplemented with a limiting amount of Met such that they grew until its depletion in late log phase ($D_{600, final}$), e.g. $D_{600}$ 12. The biosynthesis pathway for the Met analog was induced, when the cells reached a $D_{600}$ of ~3. To initiate the biosynthesis of the Met analogs, the cells were supplemented with L-homoserine and the nucleophile carrying the desired reactive group (cf. Example 1, Materials and Methods). HSAT and OHAS expression was induced by the addition of 0.2% of arabinose. All nucleophile substrates (cf. Table 1) were fed in two pulses (cf. Example 1, Materials and Methods) except $NaN_3$. Due to the cell toxic effect of the azide this substrate was supplemented at 0.5 mM and further continuously fed to the bioreactor (9.5 mM/20 h). After Met was depleted and the cells reached the $D_{600, final}$, the expression of the target protein was turned on by the addition of 1 mM IPTG. In this way, a panel of Met analog is considered to residue-specifically incorporate in place of methionine (6 residues) into Fdx. Syn, Sen, Oen and Oyn were synthesized at acceptable levels of 100-200 mg/L (~0.5-1 mM) when Met was depleted. Aha biosynthesis was weak, most probably due to the toxic effects of azide on the E. coli cells (Table 1). This cultures also showed a reduced growth rate (particularly during the first 4 hours after $NaN_3$ supplementation) compared to the other cultures (data not shown). The supplementation of the thioester "pre-drug" form was beneficial compared to the pure thiol (cf. Table 1, Sen* vs. Sen**). The biosynthesis of the reactive amino acid proceeded after Met depletion as indicated by increasing product titers (Table 1). Thus, sufficient amounts of HSAT and OHAS for the biosynthesis of the Met analogs was synthesized before Met depletion.

All Met analogs could be successfully produced in the bioreactor. The titers indicated that all Met analogs were biosynthesized at levels that are sufficient for their incorporation into a target protein. The protocol is fully scalable from shake flaks to the bioreactor.

TABLE 3

Titers of the Met analogs in the culture supernatant before Fdx induction (ni, 8-9 h) and at the end of the fermentation (24 h).

| Compound | $titer_{ni,1}$* [mg/L] | $titer_{ni,2}$* [mg/L] | $titer_{end,1}$ [mg/L] | $titer_{end,2}$ [mg/L] |
|---|---|---|---|---|
| Sen* | 13 | 14 | 29 | 27 |
| Sen** | n.d. | n.d. | 216 | n.d. |
| Syn | 148 | 160 | 268 | 238 |
| Oen | 269 | 273 | 400 | 398 |
| Oyn | 713 | 733 | 920 | 1040 |
| Aha | 2 | 2 | 5 | 4 |
| SFur | n.d: | n.d. | 137 | n.d. |
| $SN_3$ | n.d. | n.d. | 251 | n.d. | n.d., not determined;
$_{1,2}$indicate two technical replicates .;
*allylthiol;
** S-allyl thioacetate.

The successful incorporation of the reactive ncAAs into the target protein Fdx was confirmed by bioorthogonal conjugation with a fluorescence dye carrying a compatible reactive group. For that purpose, azide- and alkyne-bearing fluorescent dyes were used to proof the incorporation of Syn and Oyn as well as Aha, respectively. The azide bearing Fdx[Aha] was modified with the alkyne dye and the alkyne bearing Fdx[Syn] and Fdx[Oyn] with the azide-dye and vice versa to include controls to verify the specificity of the bioorthogonal click reactions. We also included Fdx[Met] as a negative control. In case of Fdx[Aha], a specific fluorescent band was detected at the expected size of 17 kDa (not shown). No reaction product for the azide dye was observed. In case of the proposed Fdx[Syn] and Fdx[Oyn], again a specific fluorescent band was detected at 40 kDa (not shown). The coupling reaction was specific in case of the azide dye, since no product was detected when the alkyne-dye was used.

These observations confirmed the in-situ synthesis and direct incorporation of the Met analogs. Also the biosynthesis of the ncAAs was confirmed by chemical standards. Furthermore, isolated proteins were labeled by bioorthogonal coupling with fluorescence dyes carrying the correct compatible reactivity (azide vs. alkyne and vice versa).

2.4 Biosynthesis of Norbornene Bearing Met Analogs

The biosynthesis pathway was tested with two alcohol nucleophiles, 5-norbornen-2-ol and exo-5-norbornene-2-methanol both carrying a norbornene functionality (Table 4). The same experiment as described in Example 2.2 was performed but the S-allyl thioester was exchanged for the two norbornene alcohols (Table 4). Due to possible cell toxic effects of the two alcohols, 1, 5 and 10 mM of each alcohol were tested. When analyzing the culture supernatants, a detectable peak corresponding to the expected mass of the O-norbornene-L-homoserine amino acid was obtained (not shown). The peak was not detectable if the norbornene alcohol was not supplemented to cells expressing the HSAT and OHAS enzymes. The peak also did not result from the substrate. In case of 5-norbornen-2-ol, an increase in O-norbornene-L-homoserine formation was observed with increasing nucleophile concentration. This was not the case when the cells were supplemented with exo-5-norbornene-2-methanol. This observation correlated with stalled growth behavior of cultures supplemented with exo-5-norbornene-2-methanol already at low concentrations of 1 mM.

TABLE 4

Overview of substrates used for the biosynthesis of different Met analogs using the HSAT-OHAS biosynthesis cascade.

| Substrate/nucleophile | functionality | Mw [g/mol] | source | Met-analog | Mw [g/mol] | $t_R$ [min] |
|---|---|---|---|---|---|---|
| 5-norbornen-2-ol | norbornene | 110.15 | Sigma-N32105 | O-norbornenoxy-L-homoserine | 211 | 7.062 |
| exo-5-norbornene-2-methanol | norbornene | 124.18 | Sigma-771953 | O-norbornenemethoxy-L-homoserine | 225 | 6.749 |

Example 3: Comparative AHA Biosynthesis

Methods

A over-night culture (ONC) of *E. coli* BL21 carrying pCAS5-Alkylation-12(Cg metY)-Strep-Fdx-His6 or pCAS5-Alkylation-12(Bs metY)-Strep-Fdx-His6, respectively, in 25 ml M9 Pan rich medium (1×M9 salt stock, 1 mM $MgSO_4$, 1 µg/ml $CaCl_2$, 1 µg/ml Thiamine, 0.01% D-Pantothenic acid, 20 mM glucose, 3 g/l yeast extract, trace elements, 100 µg/ml ampicillin) was incubated at 37° C., 140 rpm. A 50 ml main culture was inoculated to a start Do of 0.1 and incubated at 37° C., 130 rpm until a $D_{600}$ of 0.9. A 2 ml sample was taken before induction. The cultures were induced with 0.2% arabinose, 5 mM L-homoserine and 1 mM Na-azide. For negative controls, the addition of Na-azide was omitted in one set-up per strain. The cultures were incubated at 37° C., 130 rpm, over night (ON). A 2 ml sample was taken after 3 h of induction (t3) and after ON incubation (ON). Samples were measured for $D_{600}$ and centrifuged for 10 min at max. speed. Cells were separated from supernatant and stored at −20° C.

For HPLC-MS (Agilent technologies Inc.) analysis of the biosynthesized ncAA, 5 µL of the clarified culture supernatant were separated on a Litochrat 250 PurospherStar RP18e 5 μM column (Merck Millipore). Met analogs were separated from other metabolites in the culture supernatant by eluting with a gradient from 2 to 98% acetonitrile in 0.1% (v/v) formic acid in water within 12 minutes. A mixture of ddH$_2$O with 0.1% formic acid and acetonitrile was used as the mobile phase at a flow rate of 0.7 mL/min and the column temperature was set to 30° C. The amino acid in the supernatant was identified by its retention time in comparison to calibration standards with defined concentrations of 0.05 mM, 0.1 mM, 0.2 mM, 0.5 mM, 1.0 mM. Calibration curves were calculated by linear curve fit using EXCEL (Microsoft, Redmond, WA). Data analysis was performed using the Agilent ChemStation Software (Agilent technologies Inc.).

Results

TABLE 5

Calibration curve of AHA. Defined concentrations of AHA, their retention times ($t_R$) and peak areas were used to calculate a calibration curve with the equation: peak area = 8E+07*[mM] AHA + 1E+06, $R^2$ = 0.9998.

| AHA [mM] | channel | $t_R$ | Peak area |
|---|---|---|---|
| 0.05 | AHA | 3.792 | 5589533 |
| 0.1 | AHA | 3.774 | 8554332 |
| 0.2 | AHA | 3.778 | 16858760 |
| 0.5 | AHA | 3.778 | 38975164 |
| 1 | AHA | 3.779 | 78112096 |

Example 4: Biosynthesis of Met Analogs by Plasmid-Borne and Chromosomal Biosynthesis Pathways A two-enzyme cascade system for biosynthesis of reactive Met analogs was developed. The cascade consists of O-acetyl-homoserine sulfhydrylase (OAHS, encoded by the gene) from *Bacillus stearothermophilus* (see SEQ ID NO: 1) and L-homoserine-O-acetyltransferase (HSAT, encoded by metX) from *Deinococcus radiodurans* (see SEQ ID NO: 2). The biosynthesis reaction involves two steps and requires two precursors for biosynthesis of Met analogs. In the first step, L-homoserine (precursor 1) is acetylated to O-acetyl-homoserine and thus activated by HSAT. In the second step, OAHS converts the O-acetyl-homoserine from the first step to the Met analog in the presence of a nucleophile (precursor 2). While the nucleophile is an essential precursor that must be supplemented, L-homoserine occurs naturally in the host and supplementation is required only to increase the product yield. Depending on the nucleophile, different functionalities can be introduced into the Met analog.

A biosynthesis plasmid carrying the biosynthesis cascade genes was devised. It was intended to reduce the cellular burden for plasmid propagation and aimed at developing a stable biosynthesis host for Met analogs. To achieve this, the cascade enzymes was integrated into the chromosome of *E. coli* BL21 cells. The titer of Met analogs biosynthesized with the genomically engineered BL21 host was compared to BL21(DE3) cells carrying the biosynthesis plasmid.

Construction of the metXY Expression Strain

The bacterial clustered regularly interspaced short palindromic repeats (CRISPR)-Cas9 system for genome editing

TABLE 6

Results of HPLC analysis. Identified peaks corresponding to AHA in different samples by $t_R$, peak areas, calculated concentrations of AHA using equation obtained in Table 5, measured D$_{600}$ of cultures and AHA concentration normalized to D$_{600}$.

| | sample | channel | $t_R$ | Peak area | AHA [mM] | AHA [mg/l] | D$_{600}$ | AHA [mM]/D$_{600}$ |
|---|---|---|---|---|---|---|---|---|
| pCAS5-Alkylation-12(Bs metY)-Strep-Fdx-His6 | Before induction | AHA | — | — | — | — | 0.9 | — |
| | w/1 mM Na-azide t3 | AHA | 3.779 | 9734817 | 0.11 | 15.73 | 2.2 | 0.05 |
| | w/1 mM Na-azide ON | AHA | 3.779 | 25807920 | 0.31 | 44.69 | 3 | 0.10 |
| | w/o Na-azide t3 | AHA | — | — | — | — | 4.1 | — |
| | w/o Na-azide ON | AHA | — | — | — | — | 6 | — |
| pCAS5-Alkylation-12(Cg metY)-Strep-Fdx-His6 | Before induction | AHA | — | — | — | — | 0.9 | — |
| | w/1 mM Na-azide t3 | AHA | 3.76 | 12375072 | 0.14 | 20.49 | 3.2 | 0.04 |
| | w/1 mM Na-azide ON | AHA | 3.759 | 18526554 | 0.22 | 31.57 | 6.4 | 0.03 |
| | w/o Na-azide t3 | AHA | — | — | — | — | 4.8 | — |
| | w/o Na-azide ON | AHA | — | — | — | — | 7.4 | — | has greatly expanded toolbox for genome editing in prokaryotes and eukaryotes (Sampson & Weiss (2014) Bioessays 36(1): 34-8 https://doi.org/10.1002/bies.201300135). CRSPR/Cas9 was used for the genomic integration of the cascade enzymes metX and metY into BL21 host cells. As integration locus, E. coli melibiose operon me/AB (Albermann, et al. (2010) Biotechnol J 5(1): 32-8 doi.org/10.1002/biot.200900193) was chosen. To facilitate tight regulation of the gene expression, it was decided to use the synthetic $P_{T5\text{-}cmtO}$ promoter. Choi et al. previously reported the fusion of the E. coli T5 bacteriophage promoter N25 with the cmt operator cmtO of Pseudomonas putida F1 for the tightly regulated expression of heterologous target proteins in E. coli (Choi, et al. (2010) Appl Environ Microbiol 76(15): 5058-66 doi.org/10.1128/aem.00413-10). The $P_{T5\text{-}cmtO}$ promoter is inducible with p-isopropylbenzoate (cumate), which is nontoxic to the cells and inexpensive. They also reported that the expression of heterologous protein increases with an increasing cumate concentration. Downstream gene expression from $P_{T5\text{-}cmtO}$ is blocked when the cymR gene product binds to cmtO. A single copy of the regulator gene cymR was integrated into the chromosome. To achieve tight repression, cymR was placed under the strong constitutive $lacI^q$ promoter, which is a mutant variant of the lacI promoter with approx. 10-fold enhanced strength (Calos (1978) Nature 274(5673): 762-5 doi.org/10.1038/274762a0). The genes metX and metY encoding the cascade enzymes HSAT and OAHS were arranged in a bicistronic manner. Previously, it was observed that the amount of biosynthesized Met analogs depended on the order of the cascade enzymes metX and metY in the bicistron on the biosynthesis plasmid. The biosynthesis was enhanced when the metX gene was placed upstream to the metY gene. To easily prove the genomic integration of the cascade construct, eGFP was included as a reporter. The coding sequence was flanked by FRT sites (direct inverted repeats) for later excision from the genome using FLP recombinase (Datsenko & Wanner (2000) Proc Natl Acad Sci USA 97(12): 6640-5 doi.org/10.1073/pnas.120163297). The $P_{N25\text{-}cmtO}$-metXY-FRT>eGFP>FRT$_{lacI}{}^q$-cymR expression cassette for integration into the E. coli BL21 genome is depicted in FIG. 14.

The expression cassette was inserted into the pTarget plasmid of the CRISPR/Cas9 system (Jiang, et al. (2015) Appl Environ Microbiol 81(7): 2506-14 doi.org/10.1128/aem.04023-14). A test expression of eGFP was performed from the integration cassette on the pTarget plasmid to prove the cumate-regulatable expression. The eGFP fluorescence served as a readout of the expression level when different cumate concentrations were used for induction. A concentration of 10 μM cumate was suitable for maximal induction, and 20 μM cumate induced nearly the same expression levels of the eGFP (FIG. 15). At higher cumate concentrations, a comparably lower eGFP fluorescence was observed, which was in contrast to the observation of Choi et al. The reason for our contrasting result remains obscure, possibly it depends on different plasmid constructs (metX and metY were co-expressed with eGFP) and/or the expression conditions. Most notably, leaky expression of eGFP in the absence of cumate was observed (FIG. 15).

The cascade enzymes metX and metY were integrated together with the eGFP reporter sequence at the melAB locus of E. coli BL21 by CRISPR/Cas9 combined with λ-Red recombineering. CRISPR/Cas9 system was used that consisted of two plasmids: pTarget contained the integration cassette described above as well as the guide RNA (gRNA) targeted to the me/AB locus in the E. coli genome. The second plasmid pCas encoded the Cas9 protein, which cleaves double stranded DNA guided by the gRNA, as well as the λ-Red recombineering genes gam, exo and bet (Jiang, et al. (2015) Appl Environ Microbiol 81(7): 2506-14 doi.org/10.1128/aem.04023-14). The successful genomic integration was confirmed by colony PCR using primers that annealed in the expression construct and on the flanking genome of E. coli (FIG. 16). The sequence of the inserted expression cassette was verified by sequencing. Subsequently, the pTarget and pCas plasmids were cured. Cells were cured from pTarget first; they were unable to survive on LB$^{kan,\ spec}$ plates, which indicated that they had lost pTarget that carried a spectinomycin resistance marker (FIG. 17). In contrast, the cells grew very well on LB$^{kan}$ plates, except at a dilution of $10^{-3}$, which indicated that they still carried pCas (carries a kanamycin resistance marker).

In addition to the growth test on LB$^{kan,\ spec}$ medium, 18 colonies were analyzed by colony PCR with primers which were targeted to the integrated cassette and the flanking pTarget sequence. None of the colony PCRs showed a band at ~3 kb, which confirmed the successful curing of pTarget. Particularly, clones 1 and 9 did not show any unspecific bands except the primer cloud at the bottom of the lane (FIG. 18). Clone 1 was chosen for all further experiments and cured it from pCas.

The origin of replication pSC101 of the pCas plasmid is heat sensitive, thus the plasmid was lost when the cells were grown at 37° C. overnight. The cells which were grown at 37° C. overnight, were plated on LB$^{kan}$ as well as LB plates to check for plasmid loss. Since the pCas plasmid confers resistance to kanamycin, on the LB$^{kan}$ plate no cell growth was observed while the cells grew well on LB plates. From the LB plates, cells that had been cured from pCas were further analyzed by colony PCR. None of the positive colonies showed a PCR product (FIG. 18), which indicated the loss of pCas, because the primers annealed specifically to the pCas plasmid. This confirmed the successful construction of the E. coli BL21 ΔmelAB::metXY strain.

Production of Met Analogs by Plasmid-Borne and Chromosomal Biosynthesis Pathways Next, the capacity of the newly generated E. coli strain BL21Δ melAB::metXY to biosynthesize non-canonical Met analogs was assessed. Four Met analogs, Oyn, Oen, Saz and Fur were biosynthesized fusing E. coli strain BL21 ΔmelAB::metXY and strain BL21(DE3) {pAlkXY} with a plasmid-borne pathway construct. The latter strain carried plasmid pAlkXY (FIG. 19). a descendant of plasmid pCAS5-Alkylation-12(Bs metY)-Strep-Fdx-His6 (FIG. 12), from which Strep-Fdx-His6 had been excised. The cells were cultivated in synthetic M9 medium supplemented with D-panthenoic acid, L-homoserine and yeast extract. When the cell culture reached a density of $D_{600}$ 0.8-1, the cascade enzymes was induced with 0.2% (w/v) arabinose. At the same time, the medium was supplemented with 5 mM L-homoserine and 5 mM of the corresponding nucleophile that contained the desired reactive group. The biosynthesis was carried out at 37° C. overnight Oyn, Oen and Saz were biosynthesized with BL21 ΔmelAB::metXY and Oyn, Oen and Fur with BL21(DE3) {pAlkXY} (see Table 7). All biosynthesized Met analogs could be detect after 24 h by HPLC-MS (FIG. 20). The amount of biosynthesized Met analogs was calculated using chemically synthesized reference compounds. As shown in Table, the amount of biosynthesized Oyn and Oen was apparently higher with the plasmid-borne pathway than with the chromosomally integrated cascade enzymes. While roughly 1 mM Oen was biosynthesized with BL21(DE3) {pAlkXY}, BL21 ΔmelAB::metXY produced only one tenth. Oyn was biosynthesized efficiently with both constructs, yet, the strain carrying the plasmid biosynthesized approx. 7-fold more Oyn than the strain with the chromosomal integration. BL21 ΔmelAB::metXY biosynthesized 1.36 mM Saz, and BL21(DE3) {pAlkXY} produced 1.87 mM Fur.

TABLE 7

Comparison of Met analogs biosynthesized by Bl21 ΔmelAB::metXY and BL21(DE3) {pAlkXY}.e values were calculated using chemically synthesized reference compounds.

| Met-analogs | $MW_{calc}$ [g/mol] | $t_{R\ ref}$ | $t_{R\ obs}$ plasmid-borne | $t_{R\ obs}$ genomic | Conc [mM] genomic | Conc [MM] plasmid-borne | Conc [g/L] genomic | Conc [g/L] plasmid-borne |
|---|---|---|---|---|---|---|---|---|
| Oyn | 157.18 | 6.590 | 6.540 | 6.510 | 0.59 | 4.10 | 0.09 | 0.64 |
| Oen | 159.18 | 7.866 | 7.839 | 7.784 | 0.13 | 1.10 | 0.02 | 0.17 |
| Saz | 218.28 | 8.673 | — | 8.665 | 1.36 | — | 0.30 | — |
| Fur | 215.27 | 8.658 | 8.656 | — | — | 1.87 | — | 0.4 |

$t_{R\ ref}$, retention time of reference compound; $t_{R\ obs}$, observed retention time; Conc, concentration; $MW_{calc}$, calculated molecular weight.

Clearly, the copy number as well as the promoter affect the biosynthesis of the Met analogs. The pAlkXY plasmid carries the ColE1 origin of replication, which occurs at 25-30 copies per cell (Cantrell (2003) Methods Mol Biol 235: 257-75 doi.org/10.1385/1-59259-409-3:257). In contrast, there is only a single genomically integrated copy of the cascade enzymes. According to the copy numbers, a 25-30 times lower productivity of the BL21 ΔmelAB::metXY strain would have been expected. In the genome of this strain, metXY are expressed under the control of the T5-cmtO cumate-inducible promoter while on the pAlkXY plasmid, the cascade enzymes are expressed from the $P_{araBAD}$. It is assumed that $P_{T5-cmtO}$ is stronger than $P_{araBAD}$, which could counteract the difference in copy number and lead to the decent productivity of the strain with the genomic metXY construct.

In any case, BL21(DE3) {pAlkXY} as well as BL21 ΔmelAB::metXY biosynthesize enough Oyn, Saz and Fur for the incorporation into a target protein.

The main advantage of applying the metXY pathway for the biosynthesis of Met analogs is that the nucleophiles containing reactive alkyne-, alkene-, azide- and furan-groups are inexpensive compared to commercially available reactive ncAAs, such as e.g. L-azidohomoalanine or N-epsilon-((2-azidoethoxy)carbonyl)-L-lysine. The aim is to incorporate the biosynthesized reactive Met analogs into target proteins. Usually, 0.5-5 mM ncAA are supplemented in the medium for the site-specific incorporation. BL21 ΔmelAB::metXY biosynthesized 1.36 mM Saz, which is enough for an incorporation experiment. Likewise, BL21 {pAlkXY} produced 1.8 mM and 1.1 mM of Fur and Oen.

The invention claimed is:

1. A method for preparing a methionine analogue, comprising the following steps:
   (a) contacting a host cell with L-homoserine and one or more nucleophiles, wherein said one or more nucleophiles are selected from the group consisting of allylthiol (allyl mercaptan, 2-propene-1-thiol), S-allyl thioacetate (S-prop-2-en-1-yl ethanethioate), propargyl mercaptan (2-propyne-1-thiol), S-propargyl thioacetate (S-prop-2-yn-1-yl ethanethioate), 3-azidopropane-1-thiol, S-(3-azidopropyl)thioacetate (S-(3-azidopropyl) ethanethioate), 2-propene-1-selenol, Se-allyl selenoacetate, allyl alcohol (2-propen-1-ol), propargyl alcohol (2-propyn-1-ol), furanthiol, 3-furanmethanethiol, 5-norbornene-2-methanol (bicyclo[2.2.1]hept-5-en-2-ylmethanol), 5-norbornen-2-ol (bicyclo[2.2.1]hept-5-en-2-ol), sodium azide, hydroxyacetone (1-hydroxypropan-2-one), 4-hydroxybutan-2-one, norbornene, S-furfuryl-thioacetate, and 1-(1,2,5-dithiazepan-5-yl)-2-hydroxyethanone; and
   (b) cultivating said host cell and said one or more nucleophiles of (a) in a fermentation broth to produce one or more methionine analogues, wherein the one or more methionine analogues are selected from the group consisting of S-allyl-L-homocysteine ((2S)-2-amino-4-(prop-2-en-1-ylsulfanyl)butanoic acid; Sen or Sahc), S-propargyl-L-homocysteine (Syn), S-furyl-L-homocysteine (Fur), S-furfuryl-L-homocysteine (SFur), O-furfuryl-L-homoserine (OFur), O-allyl-L-homoserine (Oen), O-propargyl-L-homoserine (O-propargyloxy-L-homoserine, Oyn), L-azidohomoalanine (Aha), S-azidopropyl-L-homocysteine (Saz or SN$_3$), O-norbornenemethoxy-L-homoserine ((2S)-2-amino-4-(bicyclo[2.2.1]hept-5-en-2-ylmethoxy)butanoic acid; Nom), O-norbornenoxy-L-homoserine ((2S)-2-amino-4-(bicyclo[2.2.1]hept-5-en-2-yloxy)butanoic acid; Nor), O-[2-(1,2,5-dithiazepan-5-yl)-2-oxoethoxy]-L-homoserine ((2S)-2-amino-4-[2-(1,2,5-dithiazepan-5-yl)-2-oxoethoxy]butanoic acid, SEA-Hse), O-(2-oxopropoxy)-L-homoserine ((2S)-2-amino-4-(2-oxopropoxy)butanoic acid; Opo), O-(3-oxobutoxy)-L-homoserine ((2S)-2-amino-4-(3-oxobutoxy)butanoic acid; Obo), and S-allyl-L-cysteine (Sac),
   wherein said host cell encodes and stably expresses a L-homoserine-O-acetyl-transferase (HSAT) and an O-acetyl-L-homoserine sulfhydrylase (OAHS),
   wherein said OAHS comprises SEQ ID NO: 1, or comprises SEQ ID NO: 1 except for up to 15 amino acid modifications in SEQ ID NO: 1 wherein said modifications are substitutions, insertions, and/or deletions in SEQ ID NO: 1, and said OAHS is able to convert O-acetyl-L-homoserine to a methionine analogue, and wherein said HSAT comprises SEQ ID NO: 2 or 3, or comprises SEQ ID NO: 2 or 3 except for up to 15 amino acid modifications in SEQ ID NO: 2 or 3 wherein said modifications are substitutions, insertions, and/or deletions in SEQ ID NO: 2 or 3, and said HSAT is able to convert homoserine to O-acetyl-L-homoserine.

2. The method of claim 1, wherein said host cell is *E. coli*.

3. The method of claim 1, wherein said methionine analogue is selected from the group consisting of O-allyl-L-homoserine (Oen), O-propargyl-L-homoserine (O-propargyloxy-L-homoserine, Oyn), O-norbornenemethoxy-L-homoserine ((2S)-2-amino-4-(bicyclo[2.2.1]hept-5-en-2-ylmethoxy)butanoic acid; Nom), and O-norbornenoxy-L-homoserine ((2S)-2-amino-4-(bicyclo[2.2.1]hept-5-en-2-yloxy)butanoic acid; Nor).

4. The method of claim 1, wherein said one or more nucleophiles are selected from the group consisting of allyl alcohol (2-propen-1-ol), propargyl alcohol (2-propyn-1-ol), 5-norbornene-2-methanol (bicyclo[2.2.1]hept-5-en-2-ylmethanol), and 5-norbornen-2-ol (bicyclo[2.2.1]hept-5-en-2-ol).

5. The method of claim 1, wherein in a further step said methionine analogue is incorporated into a protein during protein biosynthesis.

6. The method of claim 5, wherein said protein comprises one or more methionine analogues, wherein said one or more methionine analogues comprise one or more side chains with an azido, alkyne, alkene, norbornene, keto, aldehyde or furan moiety.

7. The method of claim 5, wherein said protein comprises one or more methionine analogues selected from the group consisting of S-allyl-L-homocysteine (Sen or Sahc), S-propargyl-L-homocysteine (Syn), S-furyl-L-homocysteine (Fur), S-furfuryl-L-homocysteine (SFur), O-furfuryl-L-homoserine (OFur), O-allyl-L-homoserine (Oen), O-propargyl-L-homoserine (O-propargyloxy-L-homoserine, Oyn), L-azidohomoalanine (Aha), S-azidopropyl-L-homocysteine (Saz or SN$_3$), O-norbornenemethoxy-L-homoserine ((2S)-2-amino-4-(bicyclo[2.2.1]hept-5-en-2-ylmethoxy)butanoic acid, Nom), and O-norbornenoxy-L-homoserine ((2S)-2-amino-4-(bicyclo[2.2.1]hept-5-en-2-yloxy)butanoic acid, Nor).

8. The method of claim 5, wherein said protein comprises one or more methionine analogues selected from the group consisting of S-furyl-L-homocysteine (Fur), S-furfuryl-L-homocysteine (SFur), O-furfuryl-L-homoserine (OFur), O-allyl-L-homoserine (Oen), O-propargyl-L-homoserine (O-propargyloxy-L-homoserine, Oyn), L-azidohomoalanine (Aha), S-azidopropyl-L-homocysteine (Saz or SN$_3$), O-norbornenemethoxy-L-homoserine ((2S)-2-amino-4-(bicyclo[2.2.1]hept-5-en-2-ylmethoxy)butanoic acid, Nom), O-norbornenoxy-L-homoserine ((2S)-2-amino-4-(bicyclo[2.2.1]hept-5-en-2-yloxy)butanoic acid, Nor), O-(2-oxopropoxy)-L-homoserine (Opo), O-(3-oxobutoxy)-L-homoserine (Obo), O-[2-(1,2,5-dithiazepan-5-yl)-2-oxoethoxy]-L-homoserine ((2S)-2-amino-4-[2-(1,2,5-dithiazepan-5-yl)-2-oxoethoxy]butanoic acid, SEA-Hse) and S-allyl-L-cysteine (Sac).

9. The method of claim 1, wherein said HSAT comprises SEQ ID NO: 2 or 3 except for up to 1, 2, 3, 4, or 5 amino acid modifications in SEQ ID NO: 2 or 3.

10. The method of claim 1, wherein said OAHS comprises SEQ ID NO: 1 except for up to 10 amino acid modifications in SEQ ID NO: 1.

11. The method of claim 10, wherein said OAHS comprises SEQ ID NO: 1 except for up to 1, 2, 3, 4, or 5 amino acid modifications in SEQ ID NO: 1.

12. The method of claim 1, wherein said OAHS comprises SEQ ID NO: 1 except for up to 15 amino acid substitutions that are conservative amino acid substitutions.

* * * * *

```
                        SEQUENCE LISTING

<160> NUMBER OF SEQ ID NOS: 6

<210> SEQ ID NO 1
<211> LENGTH: 434
<212> TYPE: PRT
<213> ORGANISM: Geobacillus stearothermophilus

<400> SEQUENCE: 1

Met Ser Asn Glu Gln Thr Phe Arg Pro Glu Thr Leu Ala Ile His Ala
1               5                   10                  15

Gly Gln Lys Pro Asp Ala Glu Thr Gly Ala Arg Ala Val Pro Ile Tyr
            20                  25                  30

Gln Thr Ser Ser Tyr Val Phe Arg Asp Ser Glu His Ala Ala Asn Leu
        35                  40                  45

Phe Gly Leu Lys Glu Glu Gly Phe Ile Tyr Thr Arg Ile Met Asn Pro
    50                  55                  60

Thr Asn Asp Val Leu Glu Lys Arg Ile Ala Ala Leu Glu Gly Gly Ile
65                  70                  75                  80

Gly Ala Leu Ala Leu Ser Ser Gly Gln Ala Ala Val Phe Tyr Ser Ile
                85                  90                  95

Ile Asn Ile Ala Ser Ala Gly Asp Glu Ile Val Ser Ser Ser Ser Ile
            100                 105                 110

Tyr Gly Gly Thr Tyr Asn Leu Phe Ala His Thr Leu Arg Lys Phe Gly
        115                 120                 125

Ile Thr Val Lys Phe Val Asp Pro Ser Asp Pro Glu Asn Phe Glu Arg
    130                 135                 140

Ala Ile Thr Asp Lys Thr Lys Ala Leu Phe Ala Glu Thr Ile Gly Asn
145                 150                 155                 160
```

```
Pro Lys Asn Asp Val Leu Asp Ile Glu Ala Val Ala Asp Ile Ala His
            165                 170                 175

Arg His Ala Ile Pro Leu Ile Val Asp Asn Thr Val Ala Ser Pro Tyr
        180                 185                 190

Leu Leu Arg Pro Ile Glu Phe Gly Ala Asp Ile Val His Ser Ala
    195                 200                 205

Thr Lys Phe Ile Gly Gly His Gly Asn Ser Ile Gly Gly Val Ile Val
    210                 215                 220

Asp Ser Gly Lys Phe Asp Trp Lys Gly Ser Gly Lys Phe Pro Glu Phe
225                 230                 235                 240

Thr Glu Pro Asp Pro Ser Tyr His Gly Leu Val Tyr Val Asp Ala Val
                245                 250                 255

Gly Glu Ala Ala Tyr Ile Thr Lys Ala Arg Ile Gln Leu Leu Arg Asp
            260                 265                 270

Leu Gly Ala Ala Leu Ser Pro Phe Asn Ala Phe Leu Leu Gln Gly
        275                 280                 285

Leu Glu Thr Leu His Leu Arg Met Gln Arg His Ser Glu Asn Ala Leu
    290                 295                 300

Ala Val Ala Lys Phe Leu Glu Glu Glu Ala Val Glu Ser Val Asn
305                 310                 315                 320

Tyr Pro Gly Leu Pro Ser His Pro Ser His Glu Leu Ala Lys Lys Tyr
                325                 330                 335

Leu Pro Asn Gly Gln Gly Ala Ile Val Thr Phe Glu Ile Lys Gly Gly
            340                 345                 350

Val Glu Ala Gly Lys Lys Leu Ile Asp Ser Val Lys Leu Phe Ser His
        355                 360                 365

Leu Ala Asn Ile Gly Asp Ser Lys Ser Leu Ile Ile His Pro Ala Ser
    370                 375                 380

Thr Thr His Glu Gln Leu Thr Pro Glu Gln Leu Ser Ala Gly Val
385                 390                 395                 400

Thr Pro Gly Leu Val Arg Leu Ser Val Gly Thr Glu Ala Ile Asp Asp
                405                 410                 415

Ile Leu Asp Asp Leu Arg Gln Ala Ile Arg Gln Ser Gly Thr Val Gly
            420                 425                 430

Val Lys

<210> SEQ ID NO 2
<211> LENGTH: 334
<212> TYPE: PRT
<213> ORGANISM: Deinococcus radiodurans

<400> SEQUENCE: 2

Met Thr Ala Val Leu Ala Gly His Ala Ser Ala Leu Leu Leu Thr Glu
1               5                   10                  15

Glu Pro Asp Cys Ser Gly Pro Gln Thr Val Val Leu Phe Arg Arg Glu
            20                  25                  30

Pro Leu Leu Leu Asp Cys Gly Arg Ala Leu Ser Asp Val Arg Val Ala
        35                  40                  45

Phe His Thr Tyr Gly Thr Pro Arg Ala Asp Ala Thr Leu Val Leu His
    50                  55                  60

Ala Leu Thr Gly Asp Ser Ala Val His Glu Trp Trp Pro Asp Phe Leu
65                  70                  75                  80

Gly Ala Gly Arg Pro Leu Asp Pro Ala Asp Asp Tyr Val Val Cys Ala
                85                  90                  95
```

Asn Val Leu Gly Gly Cys Ala Gly Thr Thr Ser Ala Ala Glu Leu Ala
            100                 105                 110

Ala Thr Cys Ser Gly Pro Val Pro Leu Ser Leu Arg Asp Met Ala Arg
            115                 120                 125

Val Gly Arg Ala Leu Leu Asp Ser Leu Gly Val Arg Arg Val Arg Val
            130                 135                 140

Ile Gly Ala Ser Met Gly Gly Met Leu Ala Tyr Ala Trp Leu Leu Glu
145                 150                 155                 160

Cys Pro Asp Leu Val Glu Lys Ala Val Ile Ile Gly Ala Pro Ala Arg
                    165                 170                 175

His Ser Pro Trp Ala Ile Gly Leu Asn Thr Ala Ala Arg Ser Ala Ile
            180                 185                 190

Ala Leu Ala Pro Gly Gly Glu Gly Leu Lys Val Ala Arg Gln Ile Ala
            195                 200                 205

Met Leu Ser Tyr Arg Ser Pro Glu Ser Leu Ser Arg Thr Gln Ala Gly
210                 215                 220

Gln Arg Val Pro Gly Val Pro Ala Val Thr Ser Tyr Leu His Tyr Gln
225                 230                 235                 240

Gly Glu Lys Leu Ala Ala Arg Phe Asp Glu Gln Thr Tyr Cys Ala Leu
                    245                 250                 255

Thr Trp Ala Met Asp Ala Phe Gln Pro Ser Ser Ala Asp Leu Lys Ala
            260                 265                 270

Val Arg Ala Pro Val Leu Val Val Gly Ile Ser Ser Asp Leu Leu Tyr
            275                 280                 285

Pro Ala Ala Glu Val Arg Ala Cys Ala Ala Glu Leu Pro His Ala Asp
            290                 295                 300

Tyr Trp Glu Leu Gly Ser Ile His Gly His Asp Ala Phe Leu Met Asp
305                 310                 315                 320

Pro Gln Asp Leu Pro Glu Arg Val Gly Ala Phe Leu Arg Ser
                    325                 330

<210> SEQ ID NO 3
<211> LENGTH: 380
<212> TYPE: PRT
<213> ORGANISM: Mycobacterium smegmatis

<400> SEQUENCE: 3

Met Thr Ile Ile Glu Glu Arg Ala Thr Asp Thr Gly Met Ala Thr Val
1               5                   10                  15

Pro Leu Pro Ala Glu Gly Glu Ile Gly Leu Val His Ile Gly Ala Leu
            20                  25                  30

Thr Leu Glu Asn Gly Thr Val Leu Pro Asp Val Thr Ile Ala Val Gln
            35                  40                  45

Arg Trp Gly Glu Leu Ala Pro Asp Arg Gly Asn Val Val Met Val Leu
50                  55                  60

His Ala Leu Thr Gly Asp Ser His Val Thr Gly Pro Ala Gly Asp Gly
65                  70                  75                  80

His Pro Thr Ala Gly Trp Trp Asp Gly Val Ala Gly Pro Gly Ala Pro
                    85                  90                  95

Ile Asp Thr Asp His Trp Cys Ala Ile Ala Thr Asn Val Leu Gly Gly
            100                 105                 110

Cys Arg Gly Ser Thr Gly Pro Gly Ser Leu Ala Pro Asp Gly Lys Pro
            115                 120                 125

Trp Gly Ser Arg Phe Pro Gln Ile Thr Ile Arg Asp Gln Val Ala Ala

```
            130                 135                 140
Asp Arg Ala Ala Leu Ala Ala Leu Gly Ile Thr Glu Val Ala Ala Val
145                 150                 155                 160

Val Gly Gly Ser Met Gly Gly Ala Arg Ala Leu Glu Trp Leu Val Thr
                165                 170                 175

His Pro Asp Asp Val Arg Ala Gly Leu Val Leu Ala Val Gly Ala Arg
            180                 185                 190

Ala Thr Ala Asp Gln Ile Gly Thr Gln Ser Thr Gln Val Ala Ala Ile
            195                 200                 205

Lys Ala Asp Pro Asp Trp Gln Gly Gly Asp Tyr His Gly Thr Gly Arg
    210                 215                 220

Ala Pro Thr Glu Gly Met Glu Ile Ala Arg Arg Phe Ala His Leu Thr
225                 230                 235                 240

Tyr Arg Gly Glu Glu Glu Leu Asp Asp Arg Phe Ala Asn Thr Pro Gln
                245                 250                 255

Asp Asp Glu Asp Pro Leu Thr Gly Gly Arg Tyr Ala Val Gln Ser Tyr
            260                 265                 270

Leu Glu Tyr Gln Gly Gly Lys Leu Ala Arg Arg Phe Asp Pro Gly Thr
    275                 280                 285

Tyr Val Val Leu Ser Asp Ala Leu Ser Ser His Asp Val Gly Arg Gly
290                 295                 300

Arg Gly Gly Val Glu Ala Ala Leu Arg Ser Cys Pro Val Pro Val Val
305                 310                 315                 320

Val Gly Gly Ile Thr Ser Asp Arg Leu Tyr Pro Ile Arg Leu Gln Gln
                325                 330                 335

Glu Leu Ala Glu Leu Leu Pro Gly Cys Gln Gly Leu Asp Val Val Asp
            340                 345                 350

Ser Ile Tyr Gly His Asp Gly Phe Leu Val Glu Thr Glu Leu Val Gly
            355                 360                 365

Lys Leu Ile Arg Arg Thr Leu Glu Leu Ala Gln Arg
    370                 375                 380

<210> SEQ ID NO 4
<211> LENGTH: 59
<212> TYPE: DNA
<213> ORGANISM: artificial
<220> FEATURE:
<223> OTHER INFORMATION: oligonucleotide primer pBP1471

<400> SEQUENCE: 4
ctgagtagga caaatccgcc gtcgacaaat cataaaaaat ttatttgctt tgtgagcgg      59

<210> SEQ ID NO 5
<211> LENGTH: 59
<212> TYPE: DNA
<213> ORGANISM: artificial
<220> FEATURE:
<223> OTHER INFORMATION: oligonucleotide primer pBP1472

<400> SEQUENCE: 5
agaggcccca aggggttatg ctagcattta aatctatcag tgatggtgat ggtgatggg      59

<210> SEQ ID NO 6
<211> LENGTH: 477
<212> TYPE: DNA
<213> ORGANISM: Clostridium beijerinckii

<400> SEQUENCE: 6
```

-continued

```
atgtggagcc acccgcagtt cgaaaaagga tccatgaaaa tcgtatattg gtctggtacc      60
ggcaacactg agaaaatggc agagctcatc gctaaaggta tcatcgaatc tggtaaagac     120
gtcaacacca tcaacgtgtc tgacgttaac atcgatgaac tgctgaacga agatatcctg     180
atcctgggtt gctctgccat gggcgatgaa gttctcgagg aaagcgaatt tgaaccgttc     240
atcgaagaga tctctaccaa aatctctggt aagaaggttg cgctgttcgg ttcttatggt     300 tgggcgacg gtaagtggat gcgtgacttc gaagaacgta tgaacggcta tggttgcgtt     360
gttgttgaga ccccgctgat cgttcagaac gagccggacg aagctgagca ggactgcatc     420
gaatttggta agaagatcgc gaacatcgga tcccatcacc atcaccatca ctgatag        477
```